(12) United States Patent
Sacca et al.

(10) Patent No.: US 12,635,744 B2
(45) Date of Patent: May 26, 2026

(54) BIOMETRIC SENSOR OF A TACTICAL GEAR TO MONITOR HEALTH AND STRESS OF A WEARER

(71) Applicant: GovernmentGPT Inc., Mountain View, CA (US)

(72) Inventors: Giacomo Sacca, Allentown, NJ (US); Cameron Christensen, Mountain View, CA (US); Nelson So, Dawsonville, GA (US); Patrick M. Gibbons, Columbia, MD (US); Gary Berg, Campbell, CA (US); John Bridge, Hillsborough, NC (US); Frank L. Hammond, III, Atlanta, GA (US); Raj Abhyanker, Mountain View, CA (US)

( * ) Notice: Subject to any disclaimer, the term of this patent is extended or adjusted under 35 U.S.C. 154(b) by 111 days.

(21) Appl. No.: 18/634,891

(22) Filed: Apr. 13, 2024

(65) Prior Publication Data

US 2025/0318590 A1     Oct. 16, 2025

(51) Int. Cl.
*A41D 13/00*      (2006.01)
*A61B 5/00*      (2006.01)
(Continued)

(52) U.S. Cl.
CPC .......... *A41D 13/0002* (2013.01); *A61B 5/021* (2013.01); *A61B 5/02405* (2013.01);
(Continued)

(58) Field of Classification Search
CPC ................ A41D 13/0002; A61B 5/021; A61B 5/02405; A61B 5/0533; A61B 5/4088; A61B 2562/043
(Continued)

(56) References Cited

U.S. PATENT DOCUMENTS

| | | |
|---|---|---|
| 1,337,920 A | 4/1920 | Ernest |
| 4,008,456 A | 2/1977 | Ewart |

(Continued)

FOREIGN PATENT DOCUMENTS

| | | |
|---|---|---|
| AU | 2012201637 B2 | 9/2013 |
| CA | 2903640 A1 | 3/2017 |

(Continued)

OTHER PUBLICATIONS

"Body-Worn Camera Activation In Prisons: Understanding Correctional Officers' Decision-Making and Use of Discretion", Published at Security Journal, Published by Shannon Dodd et al., Published Online On [May 26, 2023] https://link.springer.com/article/10.1057/s41284-023-00380-7.

(Continued)

*Primary Examiner* — Naomi J Small
(74) *Attorney, Agent, or Firm* — LegalForce RAPC Worldwide

(57) ABSTRACT

Disclosed are a method, system, and apparatus of a biometric sensor of a tactical gear to monitor health and stress of a wearer. In one embodiment, personal protective equipment includes a language translator module integrated in a tactical gear, a biometric sensor, and a responsive device integrated in the tactical gear. A wearer bi-directionally communicates with an individual in an ambient environment using any language other than a primary language spoken by the wearer when the language translator module is activated. The biometric sensor detects the health condition of the wearer. The responsive device vibrates to notify the wearer when the biometric sensor detects an elevated stress level of the wearer of the tactical gear. The biometric sensor is detachable from the tactical gear and placeable on an injured person nearby to the wearer through an armband extendable (Continued)

EXPLOSION GUN SHOT
FIRE 132J 132I 132H ILLEGAL SUBSTANCE 132G
AMBIENT THREAT 132
FIST 132A
BAT 132B
GUN 132D
KNIFE 132E
RUNNING 132C
FURTIVE MOVEMENTS 132F
VISUAL SENSOR 102
INFERENCE MODULE 1724
OBJECT RECOGNITION MODULE 122
THREAT DETECTION MODEL 108
IDENTITY ARTIFICIAL INTELLIGENCE MODEL 1722
NETWORK 140
COMPUTE MODULE 118
COMBINED MEMORY AND POWER MODULE 110
UAV 136A
UAV 136N
CAMERA 142
ARMORED CARRIER 134
DRONE SYSTEM 150
BIOMETRIC SENSOR(S) 160
WEARER 114
GPS MODULE 116
USER AUTHENTICATION MEANS 120
LANGUAGE TRANSLATOR MODULE 144
TACTICAL GEAR 104
DRONE CONTROL APPARATUS 124
RESPONSIVE DEVICE 106
VALUABLES-IN-TRANSIT 138
PERSONAL PROTECTIVE EQUIPMENT 100 from the biometric sensor when it is removed from the tactical gear.

16 Claims, 28 Drawing Sheets

(51) Int. Cl.
  *A61B 5/021*     (2006.01)
  *A61B 5/024*     (2006.01)
  *A61B 5/0533*    (2021.01)
(52) U.S. Cl.
  CPC .......... *A61B 5/0533* (2013.01); *A61B 5/4088* (2013.01); *A61B 2562/043* (2013.01)
(58) Field of Classification Search
  USPC .................................................... 340/573.1
  See application file for complete search history.

(56) References Cited

U.S. PATENT DOCUMENTS

| | | | |
|---|---|---|---|
| 4,231,311 A | 11/1980 | Longerich | |
| 4,358,984 A | 11/1982 | Winblad | |
| 4,367,752 A | 1/1983 | Jimenez et al. | |
| 5,005,213 A | 4/1991 | Hanson et al. | |
| 5,219,290 A | 6/1993 | Lapp et al. | |
| 5,416,903 A | 5/1995 | Malcolm | |
| 5,594,498 A | 1/1997 | Fraley | |
| 5,677,979 A | 10/1997 | Squicciarini et al. | |
| 5,815,093 A | 9/1998 | Kikinis | |
| 5,864,481 A | 1/1999 | Gross et al. | |
| 5,942,716 A | 8/1999 | Miller | |
| 6,029,558 A | 2/2000 | Stevens et al. | |
| 6,128,999 A | 10/2000 | Sepp et al. | |
| 6,198,394 B1 | 3/2001 | Jacobsen et al. | |
| 6,215,498 B1 | 4/2001 | Filo et al. | |
| 6,219,646 B1 | 4/2001 | Cherny | |
| 6,349,201 B1 | 2/2002 | Ford | |
| 6,388,422 B1 | 5/2002 | Lew | |
| 6,481,782 B2 | 11/2002 | Bond | |
| 6,513,003 B1 | 1/2003 | Angell et al. | |
| 6,522,531 B1 | 2/2003 | Quintana et al. | |
| 6,567,503 B2 | 5/2003 | Engelke et al. | |
| 6,595,102 B2 | 7/2003 | Stevens et al. | |
| 6,613,001 B1 | 9/2003 | Dworkin | |
| 6,690,932 B1 | 2/2004 | Barnier et al. | |
| 6,784,833 B1 | 8/2004 | Evans | |
| 6,820,055 B2 | 11/2004 | Saindon et al. | |
| 6,831,556 B1 | 12/2004 | Boykin | |
| 6,980,953 B1 | 12/2005 | Kanevsky et al. | |
| 7,035,804 B2 | 4/2006 | Saindon et al. | |
| 7,046,214 B2 | 5/2006 | Ebersole, Jr et al. | |
| 7,058,710 B2 | 6/2006 | McCall et al. | |
| 7,091,852 B2 | 8/2006 | Mason et al. | |
| 7,132,928 B2 | 11/2006 | Perricone | |
| 7,173,437 B2 | 2/2007 | Hervieux et al. | |
| 7,245,216 B2 | 7/2007 | Burkley et al. | |
| 7,342,648 B2 | 3/2008 | Solomon et al. | |
| 7,389,221 B1 | 6/2008 | Pearson et al. | |
| 7,456,875 B2 | 11/2008 | Kashiwa | |
| 7,538,666 B2 | 5/2009 | Campman | |
| 7,539,086 B2 | 5/2009 | Jaroker | |
| 7,570,301 B2 | 8/2009 | Gilor | |
| 7,696,919 B2 | 4/2010 | Moraites | |
| 7,719,428 B2 | 5/2010 | Fisher et al. | |
| 7,747,434 B2 | 6/2010 | Flanagan et al. | |
| 7,768,548 B2 | 8/2010 | Silvernail et al. | |
| 7,827,900 B2 | 11/2010 | Beach et al. | |
| 7,845,018 B1 | 12/2010 | Greer | |
| 7,898,410 B2 | 3/2011 | Schurter | |
| 7,900,548 B2 | 3/2011 | Hoadley et al. | |
| 7,930,181 B1 | 4/2011 | Goffin et al. | |
| 7,996,465 B2 | 8/2011 | Cromp et al. | |
| 7,999,741 B2 | 8/2011 | Graves et al. | |
| 8,018,320 B2 | 9/2011 | Najanguaq SøVsø Andreasen Struijk | |
| 8,051,762 B2 | 11/2011 | Beach et al. | |
| 8,078,551 B2 | 12/2011 | Bar | |
| 8,141,470 B1 | 3/2012 | Farinella et al. | |
| 8,154,844 B2 | 4/2012 | Brown | |
| 8,205,537 B1 | 6/2012 | Dupont | |
| 8,239,207 B2 | 8/2012 | Seligman et al. | |
| 8,242,880 B2 | 8/2012 | Ghovanloo et al. | |
| 8,274,377 B2 | 9/2012 | Smith et al. | |
| 8,281,702 B2 | 10/2012 | Hoadley et al. | |
| 8,316,753 B2 | 11/2012 | Beach et al. | |
| 8,362,945 B2 | 1/2013 | Wootan et al. | |
| 8,370,142 B2 | 2/2013 | Frankel et al. | |
| 8,386,233 B2 | 2/2013 | Khuda | |
| 8,464,949 B2 | 6/2013 | Namey et al. | |
| 8,487,755 B2 | 7/2013 | Gudgel et al. | |
| 8,526,934 B2 | 9/2013 | Sennett et al. | |
| 8,552,847 B1 * | 10/2013 | Hill ......................... G07C 5/02 |
| | | | 340/407.1 |
| 8,593,286 B2 | 11/2013 | Razoumov et al. | |
| 8,599,010 B2 | 12/2013 | Bose et al. | |
| 8,639,396 B1 | 1/2014 | Hirsch et al. | |
| 8,674,806 B1 | 3/2014 | Malik et al. | |
| 8,676,234 B2 | 3/2014 | Conner et al. | |
| 8,698,634 B2 | 4/2014 | Guedes Lopes Da Fonseca et al. | |
| 8,755,839 B2 | 6/2014 | Parkulo et al. | |
| 8,776,662 B1 | 7/2014 | Hoenes | |
| 8,791,836 B2 | 7/2014 | Herman | |
| 8,812,096 B2 | 8/2014 | Flaherty et al. | |
| 8,838,459 B2 | 9/2014 | Uszkoreit et al. | |
| 8,853,891 B2 | 10/2014 | Soar | |
| 8,857,309 B2 | 10/2014 | Wentzel | |
| 8,872,655 B2 | 10/2014 | Buller et al. | |
| 8,896,696 B2 | 11/2014 | Ellsworth et al. | |
| 8,945,328 B2 | 2/2015 | Longinotti-Buitoni et al. | |
| 8,949,289 B2 | 2/2015 | Lasensky et al. | |
| 8,965,129 B2 | 2/2015 | Rogowski et al. | |
| 9,042,971 B2 | 5/2015 | Brumback et al. | |
| 9,063,931 B2 | 6/2015 | Wu | |
| 9,076,448 B2 | 7/2015 | Bennett et al. | |
| 9,085,362 B1 | 7/2015 | Kilian et al. | |
| 9,195,652 B2 | 11/2015 | Custer et al. | |
| 9,229,535 B2 | 1/2016 | Skinner et al. | |
| 9,245,278 B2 | 1/2016 | Orsini et al. | |
| 9,246,898 B2 | 1/2016 | McKeeman et al. | |
| 9,282,893 B2 | 3/2016 | Aliverti et al. | |
| 9,338,622 B2 | 5/2016 | Bjontegard | |
| 9,342,976 B2 | 5/2016 | Pfeffer | |
| 9,354,703 B2 | 5/2016 | Maggiali et al. | |
| 9,466,187 B2 | 10/2016 | Grant et al. | |
| 9,501,472 B2 | 11/2016 | Manuselis et al. | |
| 9,507,772 B2 | 11/2016 | Parkinson et al. | |
| 9,560,324 B2 | 1/2017 | Monaghan, Sr. et al. | |
| 9,569,431 B2 | 2/2017 | Uszkoreit et al. | |
| 9,582,035 B2 | 2/2017 | Connor | |
| 9,589,448 B1 | 3/2017 | Schneider et al. | |
| 9,602,993 B2 | 3/2017 | Vilrokx et al. | |
| 9,614,969 B2 | 4/2017 | Aue et al. | |
| 9,619,996 B1 | 4/2017 | Smith | |
| 9,695,981 B2 | 7/2017 | Au et al. | |
| 9,697,720 B1 | 7/2017 | Lassiter | |
| 9,704,209 B2 | 7/2017 | Proud et al. | |
| 9,710,819 B2 | 7/2017 | Cloran et al. | |
| 9,712,730 B2 | 7/2017 | Phillips et al. | |
| 9,720,737 B2 | 8/2017 | Ashtiani et al. | |
| 9,734,820 B2 | 8/2017 | Rangarajan Sridhar et al. | |
| 9,737,261 B2 | 8/2017 | Coza et al. | |
| 9,740,686 B2 | 8/2017 | Johansson | |
| 9,741,215 B2 | 8/2017 | Brav et al. | |
| 9,804,946 B2 | 10/2017 | Conlon et al. | |
| 9,805,273 B1 | 10/2017 | Seeber et al. | |
| 9,826,557 B2 | 11/2017 | Smith | |
| 9,881,477 B2 | 1/2018 | Hyde et al. | |
| 9,886,833 B2 | 2/2018 | Noland et al. | |
| 9,922,518 B2 | 3/2018 | Hannigan et al. | |
| 9,922,537 B2 | 3/2018 | Shah et al. | |
| 9,980,102 B2 | 5/2018 | Bohlander et al. | |
| 9,996,168 B2 | 6/2018 | Menon et al. | |

(56) References Cited

U.S. PATENT DOCUMENTS

| | | | |
|---|---|---|---|
| 10,013,858 B2 | 7/2018 | Zerick et al. |
| 10,020,909 B2 | 7/2018 | Stamm et al. |
| 10,021,672 B2 | 7/2018 | Cole et al. |
| 10,025,991 B2 | 7/2018 | Seeber et al. |
| 10,025,993 B2 | 7/2018 | Seeber et al. |
| 10,043,033 B1 | 8/2018 | Hadsall |
| 10,043,354 B2 | 8/2018 | Man et al. |
| 10,070,260 B1 | 9/2018 | Miyazawa et al. |
| 10,084,500 B2 | 9/2018 | Davis et al. |
| 10,102,732 B2 | 10/2018 | Gersten |
| 10,103,835 B2 | 10/2018 | Morrow et al. |
| 10,105,101 B2 | 10/2018 | Fougere et al. |
| 10,108,306 B2 | 10/2018 | Khoo et al. |
| 10,129,704 B1 | 11/2018 | Huseth et al. |
| 10,137,363 B2 | 11/2018 | Parshionikar |
| 10,154,391 B2 | 12/2018 | Yoakum et al. |
| 10,178,973 B2 | 1/2019 | Venkatraman et al. |
| 10,204,520 B2 | 2/2019 | Demetriades et al. |
| 10,209,365 B2 | 2/2019 | Venkatraman et al. |
| 10,229,329 B2 | 3/2019 | Seeber et al. |
| 10,230,919 B2 | 3/2019 | Davis et al. |
| 10,234,938 B2 | 3/2019 | Moffat et al. |
| 10,237,012 B2 | 3/2019 | Morrow et al. |
| 10,257,434 B2 | 4/2019 | Arnold |
| 10,258,534 B1 | 4/2019 | Sills et al. |
| 10,271,591 B2 | 4/2019 | Bangera et al. |
| 10,306,094 B2 | 5/2019 | Miklautsch et al. |
| 10,317,506 B2 | 6/2019 | Seeber et al. |
| 10,327,674 B2 | 6/2019 | Hong et al. |
| 10,349,227 B2 | 7/2019 | Saxena et al. |
| 10,351,237 B2 | 7/2019 | Baruch |
| 10,370,102 B2 | 8/2019 | Boykin et al. |
| 10,370,122 B2 | 8/2019 | Fisher et al. |
| 10,455,187 B2 | 10/2019 | Callis, Jr. et al. |
| 10,539,787 B2 | 1/2020 | Haddick et al. |
| 10,542,222 B2 | 1/2020 | Arnold |
| 10,542,929 B2 | 1/2020 | Kimmel |
| 10,560,668 B2 | 2/2020 | Araya et al. |
| 10,567,107 B2 | 2/2020 | Morrow et al. |
| 10,573,164 B2 | 2/2020 | Singh et al. |
| 10,574,384 B2 | 2/2020 | Morrow et al. |
| 10,599,106 B2 | 3/2020 | Zeier |
| 10,599,929 B2 | 3/2020 | Cuban et al. |
| 10,600,295 B2 | 3/2020 | Asher et al. |
| 10,600,417 B2 | 3/2020 | Tormasov et al. |
| 10,613,248 B2 | 4/2020 | Benke et al. |
| 10,614,171 B2 | 4/2020 | Orsini et al. |
| 10,621,443 B2 | 4/2020 | Seeber et al. |
| 10,653,202 B2 | 5/2020 | Destrian et al. |
| 10,657,362 B2 | 5/2020 | Ranganath et al. |
| 10,668,356 B2 | 6/2020 | Bangera et al. |
| 10,701,520 B2 | 6/2020 | Singh et al. |
| 10,805,576 B2 | 10/2020 | Hanchett et al. |
| 10,812,755 B2 | 10/2020 | Davis et al. |
| 10,814,894 B2 | 10/2020 | Preston et al. |
| 10,854,098 B1 | 12/2020 | Welch et al. |
| 10,861,308 B1 | 12/2020 | Simpson et al. |
| 10,861,317 B2 | 12/2020 | Wengrovitz et al. |
| 10,861,320 B2 | 12/2020 | Martin et al. |
| 10,866,597 B1 | 12/2020 | Reinhold et al. |
| 10,896,598 B1 | 1/2021 | Boss et al. |
| 10,901,373 B2 | 1/2021 | Locke et al. |
| 10,970,934 B2 | 4/2021 | Rogers et al. |
| 10,977,452 B2 | 4/2021 | Wang et al. |
| 11,025,723 B2 | 6/2021 | Fortna et al. |
| 11,032,515 B2 | 6/2021 | Mazzarella et al. |
| 11,057,584 B2 | 7/2021 | Davis et al. |
| 11,062,584 B1 | 7/2021 | Magaletta |
| 11,076,134 B2 | 7/2021 | Govezensky et al. |
| 11,087,613 B2 | 8/2021 | Barber |
| 11,096,590 B2 | 8/2021 | Tang et al. |
| 11,122,237 B2 | 9/2021 | Nguyen et al. |
| 11,126,204 B2 | 9/2021 | Abramov et al. |
| 11,158,343 B2 | 10/2021 | Hershfield et al. |
| 11,160,504 B2 | 11/2021 | Yun et al. |
| 11,170,782 B2 | 11/2021 | Stoker et al. |
| 11,188,854 B2 | 11/2021 | Dimino et al. |
| 11,197,773 B2 | 12/2021 | Sakuma et al. |
| 11,216,954 B2 | 1/2022 | Peled et al. |
| 11,232,702 B2 | 1/2022 | Huseth et al. |
| 11,272,779 B2 | 3/2022 | Grinnell |
| 11,288,973 B2 | 3/2022 | Vacek |
| 11,297,164 B2 | 4/2022 | McCormack et al. |
| 11,304,778 B2 | 4/2022 | Shanjani et al. |
| 11,308,792 B2 | 4/2022 | Rao |
| 11,315,396 B2 | 4/2022 | Kaindl |
| 11,375,161 B2 | 6/2022 | Shimada et al. |
| 11,385,022 B2 | 7/2022 | Hatcher et al. |
| 11,388,546 B2 | 7/2022 | Williams |
| 11,425,653 B2 | 8/2022 | Hanchett et al. |
| 11,436,900 B2 | 9/2022 | Baron et al. |
| 11,521,128 B2 | 12/2022 | Moro et al. |
| 11,521,285 B2 | 12/2022 | Schuler et al. |
| 11,622,138 B2 | 4/2023 | MacDonald |
| 11,632,539 B2 | 4/2023 | Smith et al. |
| 11,645,904 B2 | 5/2023 | Trundle et al. |
| 11,706,391 B1 | 7/2023 | Heywood et al. |
| 11,717,185 B2 | 8/2023 | Cusey et al. |
| 11,741,820 B1 | 8/2023 | Bacco et al. |
| 11,749,074 B2 | 9/2023 | Attariani et al. |
| 11,790,741 B2 | 10/2023 | Williams |
| 11,819,324 B2 | 11/2023 | Cusey et al. |
| 11,877,614 B2 | 1/2024 | Berzowska et al. |
| 11,879,705 B2 | 1/2024 | Taveniku |
| 11,893,101 B2 | 2/2024 | Haraguchi et al. |
| 11,900,915 B2 | 2/2024 | Chen et al. |
| 11,902,871 B2 | 2/2024 | Pellegrini et al. |
| 11,920,901 B2 | 3/2024 | Basche et al. |
| 11,942,093 B2 | 3/2024 | Dubinsky et al. |
| 12,392,583 B2 * | 8/2025 | Bridge ..................... F41H 1/00 |
| 2001/0029455 A1 | 10/2001 | Chin et al. |
| 2002/0026431 A1 | 2/2002 | Pedersen et al. |
| 2002/0145849 A1 | 10/2002 | Peterson |
| 2002/0149510 A1 | 10/2002 | Salzeder |
| 2002/0196202 A1 | 12/2002 | Bastian et al. |
| 2003/0065503 A1 | 4/2003 | Agnihotri et al. |
| 2003/0115059 A1 | 6/2003 | Jayaratne |
| 2003/0125998 A1 | 7/2003 | McKenney et al. |
| 2004/0219491 A1 | 11/2004 | Shlomo |
| 2005/0054940 A1 | 3/2005 | Almen |
| 2005/0264412 A1 | 12/2005 | Levesque et al. |
| 2006/0028556 A1 | 2/2006 | Bunn et al. |
| 2006/0077253 A1 | 4/2006 | VanRiper et al. |
| 2006/0107829 A1 | 5/2006 | Shumov et al. |
| 2006/0190250 A1 | 8/2006 | Saindon et al. |
| 2006/0211404 A1 | 9/2006 | Cromp et al. |
| 2006/0225566 A1 | 10/2006 | Lloyd |
| 2007/0213088 A1 | 9/2007 | Sink |
| 2007/0229356 A1 | 10/2007 | Kodrin |
| 2007/0268368 A1 | 11/2007 | Bradford |
| 2008/0001764 A1 | 1/2008 | Douglas et al. |
| 2008/0114220 A1 | 5/2008 | Banet et al. |
| 2008/0133299 A1 | 6/2008 | Sitarski |
| 2008/0165047 A1 | 7/2008 | Fisher et al. |
| 2008/0219100 A1 | 9/2008 | Fisher et al. |
| 2008/0258063 A1 | 10/2008 | Rapanotti |
| 2008/0291075 A1 | 11/2008 | Rapanotti |
| 2009/0031467 A1 | 2/2009 | Swindells et al. |
| 2009/0055347 A1 | 2/2009 | Hollman et al. |
| 2009/0174547 A1 | 7/2009 | Greene et al. |
| 2009/0257603 A1 | 10/2009 | Chan et al. |
| 2009/0311928 A1 | 12/2009 | McClintock et al. |
| 2010/0057435 A1 | 3/2010 | Kent et al. |
| 2010/0246328 A1 | 9/2010 | Gudgel et al. |
| 2010/0315228 A1 | 12/2010 | Grilliot et al. |
| 2010/0319524 A1 | 12/2010 | Farinella et al. |
| 2011/0077933 A1 | 3/2011 | Miyamoto et al. |
| 2011/0113952 A1 | 5/2011 | Rosenwasser et al. |
| 2011/0187524 A1 | 8/2011 | Cochran, III |
| 2011/0279270 A1 | 11/2011 | Marckwald et al. |
| 2012/0011994 A1 | 1/2012 | Hoadley et al. |
| 2012/0126960 A1 | 5/2012 | Steger et al. |
| 2012/0174299 A1 | 7/2012 | Balzano |
| 2012/0198593 A1 | 8/2012 | Beck et al. |

(56) References Cited

U.S. PATENT DOCUMENTS

| | | |
|---|---|---|
| 2012/0259554 A1 | 10/2012 | Chen et al. |
| 2012/0271121 A1 | 10/2012 | Della Torre et al. |
| 2012/0275272 A1 | 11/2012 | Mullen et al. |
| 2012/0286933 A1 | 11/2012 | Hsiao |
| 2012/0299751 A1 | 11/2012 | Verna et al. |
| 2012/0299826 A1 | 11/2012 | Moeller |
| 2012/0330643 A1 | 12/2012 | Frei et al. |
| 2013/0057693 A1 | 3/2013 | Baranek |
| 2013/0090931 A1 | 4/2013 | Ghovanloo et al. |
| 2013/0200118 A1 | 8/2013 | Johnson |
| 2013/0300535 A1 | 11/2013 | Gorman |
| 2014/0030982 A1 | 1/2014 | Cardona |
| 2014/0081091 A1 | 3/2014 | Abolfathi et al. |
| 2014/0102288 A1 | 4/2014 | Yeshurun et al. |
| 2014/0118554 A1 | 5/2014 | Bucknor |
| 2014/0135593 A1 | 5/2014 | Jayalth et al. |
| 2014/0266705 A1 | 9/2014 | McKinley et al. |
| 2014/0349597 A1 | 11/2014 | Abolfathi et al. |
| 2014/0358516 A1 | 12/2014 | Lin et al. |
| 2014/0368814 A1 | 12/2014 | Krupkin et al. |
| 2015/0172520 A1 | 6/2015 | Lindman et al. |
| 2015/0189133 A1 | 7/2015 | Sandy |
| 2015/0241153 A1 | 8/2015 | Mardirossian |
| 2015/0290453 A1 | 10/2015 | Tyler et al. |
| 2015/0301619 A1 | 10/2015 | Menon |
| 2015/0346840 A1 | 12/2015 | Alonaizi |
| 2016/0000548 A1 | 1/2016 | Aiden et al. |
| 2016/0038083 A1 | 2/2016 | Ding et al. |
| 2016/0073025 A1 | 3/2016 | Cilia |
| 2016/0078020 A1 | 3/2016 | Sumita et al. |
| 2016/0088498 A1 | 3/2016 | Sharawi |
| 2016/0117940 A1 | 4/2016 | Gomory et al. |
| 2016/0125705 A1 | 5/2016 | Hurtig et al. |
| 2016/0154468 A1 | 6/2016 | Kimmel |
| 2016/0178326 A1 | 6/2016 | Strauss et al. |
| 2016/0182850 A1 | 6/2016 | Thompson |
| 2016/0310022 A1 | 10/2016 | Stivoric et al. |
| 2016/0338640 A1* | 11/2016 | Chan ..................... A61B 5/352 |
| 2016/0360146 A1 | 12/2016 | Smith |
| 2016/0367188 A1 | 12/2016 | Malik et al. |
| 2017/0049164 A1* | 2/2017 | Gruentzig ................ A41D 3/00 |
| 2017/0061784 A1 | 3/2017 | Clough |
| 2017/0071551 A1* | 3/2017 | Jain ...................... A61B 5/4884 |
| 2017/0092138 A1 | 3/2017 | Trundle et al. |
| 2017/0102460 A1 | 4/2017 | Harris |
| 2017/0127257 A1 | 5/2017 | Saxena et al. |
| 2017/0135633 A1 | 5/2017 | Connor |
| 2017/0154521 A1 | 6/2017 | Zamorano-Larrate |
| 2017/0163956 A1 | 6/2017 | Lorenzetti |
| 2017/0187876 A1 | 6/2017 | Hayes et al. |
| 2017/0193308 A1 | 7/2017 | Buyse et al. |
| 2017/0232300 A1* | 8/2017 | Tran ...................... G06F 1/163 |
| | | 434/247 |
| 2017/0238129 A1 | 8/2017 | Maier et al. |
| 2017/0253330 A1 | 9/2017 | Saigh et al. |
| 2017/0272707 A1 | 9/2017 | Davis et al. |
| 2017/0277700 A1 | 9/2017 | Davis et al. |
| 2017/0337791 A1 | 11/2017 | Gordon-Carroll |
| 2017/0339741 A1 | 11/2017 | K et al. |
| 2017/0364349 A1 | 12/2017 | Conant et al. |
| 2018/0047387 A1 | 2/2018 | Nir |
| 2018/0050800 A1 | 2/2018 | Boykin et al. |
| 2018/0059660 A1 | 3/2018 | Heatzig et al. |
| 2018/0078843 A1* | 3/2018 | Tran ................... G09B 19/0038 |
| 2018/0122205 A1 | 5/2018 | Mujeeb |
| 2018/0142924 A1* | 5/2018 | Limon .................... F25B 21/02 |
| 2018/0233019 A1 | 8/2018 | Werronen et al. |
| 2018/0292542 A1 | 10/2018 | Anand |
| 2018/0300008 A1 | 10/2018 | Rasanen |
| 2018/0325187 A1 | 11/2018 | Coalson, Jr. |
| 2018/0327091 A1 | 11/2018 | Burks et al. |
| 2018/0341262 A1 | 11/2018 | Yeshurun |
| 2018/0367237 A1 | 12/2018 | Morrow et al. |
| 2019/0004596 A1 | 1/2019 | Postcard et al. |
| 2019/0037934 A1 | 2/2019 | Swank et al. |
| 2019/0041975 A1 | 2/2019 | Anderson et al. |
| 2019/0045020 A1* | 2/2019 | Ein-Gil .................. A61B 5/165 |
| 2019/0122516 A1 | 4/2019 | Lorenzetti et al. |
| 2019/0130913 A1 | 5/2019 | Li |
| 2019/0248391 A1 | 8/2019 | Preston et al. |
| 2019/0283247 A1 | 9/2019 | Chang et al. |
| 2019/0302894 A1 | 10/2019 | Alvarado et al. |
| 2019/0369939 A1 | 12/2019 | Levesque et al. |
| 2020/0020356 A1 | 1/2020 | Smith et al. |
| 2020/0106818 A1 | 4/2020 | Luong |
| 2020/0170566 A1* | 6/2020 | Radivojevic ....... A61B 5/02444 |
| 2020/0225684 A1 | 7/2020 | Anderson et al. |
| 2020/0229739 A1 | 7/2020 | Reddy |
| 2020/0288089 A1 | 9/2020 | Thiel et al. |
| 2020/0371227 A1 | 11/2020 | Malhi |
| 2020/0375528 A1 | 12/2020 | Flanagan |
| 2020/0380959 A1 | 12/2020 | Chen |
| 2021/0071972 A1 | 3/2021 | Deng et al. |
| 2021/0085247 A1 | 3/2021 | Meirav |
| 2021/0137382 A1 | 5/2021 | Koster |
| 2021/0145450 A1 | 5/2021 | Gruentzig |
| 2021/0148679 A1 | 5/2021 | Basche et al. |
| 2021/0152788 A1 | 5/2021 | Ross |
| 2021/0192918 A1 | 6/2021 | Samadani et al. |
| 2021/0256246 A1 | 8/2021 | Dagdeviren et al. |
| 2021/0312143 A1 | 10/2021 | Trehan |
| 2021/0326563 A1 | 10/2021 | Kossor |
| 2021/0345118 A1 | 11/2021 | Guzik |
| 2021/0346738 A1 | 11/2021 | Howland |
| 2021/0364256 A1 | 11/2021 | Pirc et al. |
| 2021/0401075 A1 | 12/2021 | Gruentzig |
| 2022/0004251 A1 | 1/2022 | Vega Gálvez et al. |
| 2022/0067394 A1 | 3/2022 | Suksi et al. |
| 2022/0096207 A1 | 3/2022 | Shanjani et al. |
| 2022/0148320 A1 | 5/2022 | Alakarhu et al. |
| 2022/0172585 A1 | 6/2022 | Wedig et al. |
| 2022/0198597 A1 | 6/2022 | Hanchett et al. |
| 2022/0223247 A1 | 7/2022 | Davidson et al. |
| 2022/0231873 A1 | 7/2022 | Werfelli et al. |
| 2022/0270610 A1 | 8/2022 | Spitzer-Williams et al. |
| 2022/0288390 A1 | 9/2022 | Papay et al. |
| 2022/0300719 A1 | 9/2022 | Raina |
| 2022/0303449 A1 | 9/2022 | Bohlander et al. |
| 2022/0311979 A1 | 9/2022 | Wexler et al. |
| 2022/0353478 A1 | 11/2022 | Alakarhu et al. |
| 2022/0364829 A1 | 11/2022 | Wallack et al. |
| 2023/0009588 A1 | 1/2023 | Alphonse et al. |
| 2023/0021300 A9 | 1/2023 | Rathnam et al. |
| 2023/0047787 A1* | 2/2023 | Chappell, III .......... G06F 3/015 |
| 2023/0049184 A1 | 2/2023 | Alakarhu |
| 2023/0073359 A1 | 3/2023 | Kukuk |
| 2023/0073517 A1 | 3/2023 | Jones et al. |
| 2023/0074279 A1 | 3/2023 | Spitzer-Williams et al. |
| 2023/0097676 A1 | 3/2023 | Liew et al. |
| 2023/0102363 A1 | 3/2023 | Mehring |
| 2023/0149143 A1 | 5/2023 | Shanjani et al. |
| 2023/0157564 A1 | 5/2023 | Zuckerman-Stark et al. |
| 2023/0169881 A1 | 6/2023 | Evans et al. |
| 2023/0188243 A1 | 6/2023 | Reynolds et al. |
| 2023/0209156 A1 | 6/2023 | Lambert et al. |
| 2023/0209440 A1 | 6/2023 | Frusina et al. |
| 2023/0223038 A1 | 7/2023 | Shastry et al. |
| 2023/0260070 A1 | 8/2023 | Smith et al. |
| 2023/0262426 A1 | 8/2023 | Bohlander et al. |
| 2023/0280125 A1 | 9/2023 | Prodzenko |
| 2023/0284004 A1 | 9/2023 | Pellegrini et al. |
| 2023/0300591 A1 | 9/2023 | Hamre et al. |
| 2023/0336958 A1 | 10/2023 | Mehta et al. |
| 2023/0349667 A1 | 11/2023 | Wagner et al. |
| 2023/0388416 A1 | 11/2023 | Srivastava et al. |
| 2023/0400551 A1 | 12/2023 | Parker et al. |
| 2023/0417919 A1 | 12/2023 | Goldstein et al. |
| 2024/0031522 A1 | 1/2024 | Davis et al. |
| 2024/0046952 A1 | 2/2024 | Davis et al. |
| 2024/0048673 A1 | 2/2024 | Thiel |
| 2024/0053819 A1 | 2/2024 | Browy |
| 2024/0096467 A1* | 3/2024 | Jackson ................. G16H 20/60 |

(56) References Cited

U.S. PATENT DOCUMENTS

| | | | |
|---|---|---|---|
| 2024/0099934 A1* | 3/2024 | Stanfield | A41D 13/12 |
| 2025/0265604 A1* | 8/2025 | Ackland | A63B 24/00 |

FOREIGN PATENT DOCUMENTS

| | | |
|---|---|---|
| CA | 2997443 C | 2/2021 |
| CN | 100577095 C | 1/2010 |
| CN | 101849713 A | 10/2010 |
| CN | 102120070 A | 7/2011 |
| CN | 102783193 A | 11/2012 |
| CN | 102903361 A | 1/2013 |
| CN | 103576691 A | 2/2014 |
| CN | 104635243 A | 5/2015 |
| CN | 104207761 B | 5/2016 |
| CN | 106127123 A | 11/2016 |
| CN | 206026321 U | 3/2017 |
| CN | 106652625 A | 5/2017 |
| CN | 103533129 B | 6/2017 |
| CN | 207039772 U | 2/2018 |
| CN | 105741514 B | 3/2018 |
| CN | 108806356 A | 11/2018 |
| CN | 105632049 A | 6/2019 |
| CN | 110177334 A | 8/2019 |
| CN | 111199668 A | 5/2020 |
| CN | 112419661 A | 2/2021 |
| CN | 213238622 U | 5/2021 |
| CN | 214906815 U | 11/2021 |
| CN | 114580980 A | 6/2022 |
| CN | 111124125 B | 6/2023 |
| CN | 116308944 B | 9/2023 |
| CN | 116943088 A | 10/2023 |
| DE | 102015003323 B4 | 2/2020 |
| EP | 3789966 A1 | 3/2021 |
| ES | 2343398 B1 | 6/2011 |
| IT | 202100017246 A1 | 12/2022 |
| JP | 2002230238 A | 8/2002 |
| JP | 2008529354 A | 7/2008 |
| JP | 2013171476 A | 9/2013 |
| JP | 2016131604 A | 7/2016 |
| JP | 2021027408 A | 2/2021 |
| JP | 7369507 B2 | 10/2023 |
| KR | 200453024 Y1 | 3/2011 |
| KR | 101197435 B1 | 11/2012 |
| KR | 101245165 B1 | 3/2013 |
| KR | 101440362 B1 | 9/2014 |
| KR | 101480302 B1 | 1/2015 |
| KR | 101613022 B1 | 4/2016 |
| KR | 20200104759 A | 9/2020 |
| KR | 102298763 B1 | 9/2021 |
| KR | 102442179 B1 | 9/2022 |
| KR | 102495287 81 | 2/2023 |
| KR | 20230128744 A | 9/2023 |
| TW | 201545132 A | 12/2015 |
| TW | I825793 B | 12/2023 |
| WO | 2001035044 A1 | 5/2001 |
| WO | 2006090371 A2 | 8/2006 |
| WO | 2008018947 A2 | 2/2008 |
| WO | 2011092553 A1 | 8/2011 |
| WO | 2011119673 A2 | 9/2011 |
| WO | 2012075292 A2 | 6/2012 |
| WO | 2012079791 A1 | 6/2012 |
| WO | 2014176485 A1 | 10/2014 |
| WO | 2014197463 A2 | 12/2014 |
| WO | 2015019360 A1 | 2/2015 |
| WO | 2015034149 A1 | 3/2015 |
| WO | 2016069052 A1 | 5/2016 |
| WO | 2017053693 A1 | 3/2017 |
| WO | 2018190748 A1 | 10/2018 |
| WO | 2018195704 A1 | 11/2018 |
| WO | 2020036643 A2 | 2/2020 |
| WO | 2020069512 A1 | 4/2020 |
| WO | 2020112245 A2 | 6/2020 |
| WO | 2020256906 A1 | 12/2020 |
| WO | 2021064490 A1 | 4/2021 |
| WO | 2022251371 A2 | 12/2022 |
| WO | 2022256698 A1 | 12/2022 |
| WO | 2023043965 A1 | 3/2023 |
| WO | 2023086851 A1 | 5/2023 |
| WO | 2023247811 A1 | 12/2023 |

OTHER PUBLICATIONS

"Airfence", by Sensofusion, Found Online On [Jul. 19, 2024] https://sensofusion.com/airfence/.

"A Real-Time End-to-End Multilingual Speech Recognition Architecture", Published at IEEE Journal of Selected Topics in Signal Processing, Published by Javier Gonzalez-Dominguez et al., Published Online On [Oct. 23, 2014] https://ieeexplore.ieee.org/stamp/stamp.jsp?tp=&arnumber=6935076.

"Real-Time Multilingual Speech Recognition and Speaker Diarization System Based On Whisper Segmentation", Published at PeerJ Computer Science, Published by Ke-Ming Lyu et al., Published Online On [Mar. 29, 2024] https://peerj.com/articles/cs-1973.pdf.

"Simultaneous Speech-To-Speech Translation System With Neural Incremental ASR, MT, And TTS", Published at Nara Institute of Science and Technology, Published by Katsuhito Sudoh et al., Published Online On [Nov. 10, 2020] https://arxiv.org/pdf/2011.04845.

"Simple, Lexicalized Choice of Translation Timing for Simultaneous Speech Translation", Published at Nara Institute of Science and Technology, Published by Tomoki Fujita, Published Online in [Jan. 2013] https://www.isca-archive.org/interspeech_2013/fujita13_interspeech.pdf.

"Real Time Speech Translator", Published at Czech Technical University (CTU), Published by Xavier Garcia Cabrera, Published Online On [Jun. 25, 2008] https://upcommons.upc.edu/bitstream/handle/2099.1/6128/memoria.pdf?sequence=1&isAllowed=y.

"An Empirical Simulation-based Study of Real-Time Speech Translation for Multilingual Global Project Teams", Published at International Symposium on Empirical Software Engineering and Measurement, Published by Fabio Calefato et al., Published Online On [Sep. 18, 2014] https://collab.di.uniba.it/fabio/wp-content/uploads/sites/5/2014/05/ESEM2014_camera-ready.pdf.

"Turning Whisper into Real-Time Transcription System", Published at International Joint Conference on Natural Language Processsing (IJCNLP) and the 3rd Conference of the Asia-Pacific Chapter of the Association for Computational Linguistics (AACL), Published by Dominik Macháček et al., Published Online in [Nov. 2023] https://aclanthology.org/2023.ijcnlp-demo.3.pdf.

"Precision Payload Delivery System", by Corvo, Found Online On [Jul. 19, 2024] https://corvouas.com.au/wp-content/uploads/CORVO-PPDS-web-version-23082023-compressed.pdf.

"RQ-20 Puma", by AeroVironment, Inc., Published Online On [Aug. 4, 2020] https://english.iswnews.com/14555/military-knowledge-rq-20-puma-drone/.

"Counter Drone Systems", by Adani Defence and Aerospace, Found Online On [Jul. 19, 2024] https://www.adanidefence.com/en/counter-drone-systems.

"Dragon Eye Miniature UAV", by Defence Update, Published Online On [Aug. 23, 2005] https://defense-update.com/20050823_dragon-eye.html#google_vignette.

"Countering the UAS Threat", by Defence Update, Published by Tamir Eshel, Published Online On [Jun. 27, 2024] https://defense-update.com/20240627_c-uas-2.html#google_vignette.

"Multilingual Speech Transcription and Translation System", Published at International Journal of Advanced Research in Science, Communication and Technology (IJARSCT), Published by Dheeraj K N et al., Published Online in [Jun. 2024] https://ijarsct.co.in/Paper18843.pdf.

"Real Time Direct Speech-to-Speech Translation", Published at International Research Journal of Engineering and Technology (IRJET), Published by Sanchit Chaudhari et al., Published Online in [Jan. 2022] https://www.irjet.net/archives/V9/i1/IRJET-V9I1104.pdf.

"Methods and algorithms of correction of propagation factor influence on errors of measurement coordinates receivers GNSS", Published at International Crimean Conference Microwave & Telecom-

(56) References Cited

OTHER PUBLICATIONS munication Technology, Published by V. I. Lutsenko et al., Published Online On [Oct. 22, 2012] https://ieeexplore.ieee.org/document/6335995/authors#authors.

"Elimination of abnormally high errors of determining the coordinates of global navigation satellite system receivers", Published at International Crimean Conference Microwave & Telecommunication Technology, Published by V.I. Lutsenko et al., Published Online On [Nov. 4, 2013] https://ieeexplore.ieee.org/document/6652840/authors#authors.

"Interpolation method of introducing differential corrections into measurements of coordinate and pseudoranges in global navigation systems", Published at International Crimean Conference Microwave & Telecommunication Technology, Published by V.I. Lutsenko et al., Published Online On [Nov. 4, 2013] https://ieeexplore.ieee.org/document/6652837/authors#authors.

"Fixed-Wing UAV Systems: Modular VTOL, Long-Range Maritime UAV, Tactical ISR UAS", by Tekever, Found Online On [Jul. 19, 2024] https://www.unmannedsystemstechnology.com/company/tekever/.

"Introducing Generative AI for Law Enforcement", by C3 AI, Published at Youtube, Published Online On [Aug. 10, 2023] https://www.youtube.com/watch?v=eO4cQjnwqgo.

"Vanderbilt Engineering Students Create "Smart Vest" to Save Police Officers", by Vanderbilt University, Published at Youtube, Published Online On [Apr. 27, 2017] https://www.youtube.com/watch?v=jq5DO3717E8.

"Smart Vest", by Harley-Davidson, Published at Youtube, Published Online On [Apr. 9, 2024] https://www.youtube.com/watch?v=C42bk5h4y-E.

"This Vest Can Save Lives", by Virginia Tech, Published at Youtube, Published online on [Sep. 1, 2015] https://www.youtube.com/watch?v=79x7_N6mTYo&t=6s.

"Vanderbilt Students Create Smart Police Vest", by Sarah McCarthy, Published at Newschannel 5, Published online On [Apr. 27, 2017] https://www.newschannel5.com/news/vanderbilt-students-create-smart-police-vest.

"Vanderbilt Students Develop Smart Police Vest That Calls For Backup", by Ariana Maia Sawyer, Published at The Tennessee, Published Online On [Apr. 25, 2017] https://www.tennessean.com/story/news/crime/2017/04/24/vanderbilt-students-develop-smart-police-vest-calls-backup/100854078/.

"Prototype "Smart Vest" Could Greatly Reduce Highway Worker Deaths and Injuries By Talking to Traffic", by Tom Jackson, Published at EquipmentWorld, Published Online on [Sep. 22, 2015] https://www.equipmentworld.com/roadbuilding/video/14963694/prototype-smart-vest-could-greatly-reduce-highway-worker-deaths-and-injuries-by-talking-to-traffic.

"Smart Vest: Wearable Multi-Parameter Remote Physiological Monitoring System", by P.S. Pandian, Published at Medical Engineering & Physics, Published Online On [Sep. 14, 2007] https://www.sciencedirect.com/science/article/abs/pil/S1350453307000975?via%3Dihub.

"Robust Speech Recognition via Large-Scale Weak Supervision", by Alec Radford et al., Published at Cornell University, Published Online On [Dec. 6, 2022] https://arxiv.org/pdf/2212.04356.

"Faster-whisper", Published at Github, Found Online On [May 1, 2024] https://github.com/SYSTRAN/faster-whisper.

"Insanely Fast Whisper", Published at Github, Found Online On [May 1, 2024] https://github.com/Vaibhavs10/insanely-fast-whisper.

"WhisperLive", Published at Github, Found Online On [May 1, 2024] https://github.com/collabora/WhisperLive.

"Whisper.cpp", Published at Github, Found Online On [May 1, 2024] https://github.com/ggerganov/whisper.cpp/tree/master.

"Exploration of Alerting Methods on Vest-Worn System", by Kristen P. Hines, Published at Virginia Polytechnic Institute and State University, Published online On [May 4, 2016] https://vtechworks.lib.vt.edu/server/api/core/bitstreams/af47ee5d-2b50-462d-9da7-bd7982a1ecf3/content.

"Artificial Intelligence and Face Recognition for Body Cams", by Hernan Cafiel, Published at Ebenezer Technologies, Published Online on [Dec. 9, 2022] https://ebenezertechs.com/face-recognition-body-cams/.

"Integrating Body-Worn Cameras, Drones, And AI: A Framework Or Enhancing Police Readiness And Response", by Amanda Davies et al., Published at Oxford University Press, Published Online On [Dec. 13, 2023] https://academic.oup.com/policing/article/doi/10.1093/police/paad083/7471863.

"Security Analysis of First Responder Mobile and Wearable Devices", by Joshua M. Franklin, Published at National Institute of Standards and Technology Interagency, Published Online In [May 2020] https://nvlpubs.nist.gov/nistpubs/ir/2020/NIST.IR.8196.pdf.

"Body Worn Cameras With Facial Recognition Technology: When It Constitutes a Search", by Kelly Blount, Published at American University Washington College of Law, Published Online In [2017] https://core.ac.uk/download/pdf/327253044.pdf.

"Towards On-Device Face Recognition in Body-worn Cameras", by Ali Almadan, Published at IEEE International Workshop on Biometrics and Forensics, Published Online On [Apr. 7, 2021] https://arxiv.org/pdf/2104.03419.

"Law Enforcement's Pairing of Facial Recognition Technology with Body-Worn Cameras Escalates Privacy Concerns", by Katelyn Ringrose, Published at Virginia Law Review, Published Online On [Feb. 18, 2019] https://virginialawreview.org/wp-content/uploads/2020/12/04.%20Final%20Ringrose.pdf.

"Police use of facial recognition technology: The potential for engaging the public through co-constructed policy-making", by Dallas Hill, Published at International Journal of Police Science & Management, Published Online On [Apr. 4, 2022] https://journals.sagepub.com/doi/epub/10.1177/14613557221089558.

"Information Technology on the Beat: The Impacts of Body-Worn Camera and Facial Recognition Technology on Public Safety", by Jiyong Park, Published at University of North Carolina, Published Online On [Jul. 24, 2019] https://shorturl.at/bfqL.4.

"Chilling: The Constitutional Implications of Body-Worn Cameras and Facial Recognition Technology at Public Protests", by Julian R. Murphy, Published at Washington and Lee University, Published Online on [Aug. 30, 2018] https://scholarlycommons.law.wlu.edu/cgi/viewcontent.cgi?article=1104&context=wluir-online.

"Recent Advances in Wearable Sensors for Health Monitoring", by Mary M. Rodgers, Published at IEEE Sensors Journal, Published online On [Sep. 16, 2014] https://shorturl.at/nwxY2.

"Dress for Success: Embedded Health Sensors In The Future Soldier", by Paul Dhillon, Published at Journal of Military, Veteran and Family Health, Published Online In [2022] https://jmvfh.utpjournals.press/doi/pdf/10.3138/jmvfh-2021-0095.

"How Biometric Monitoring Will Save Law Enforcement Lives", by Lt. Grant Bedford, Published at Police1, Published Online On [Dec. 18, 2019] https://www.police1.com/health-fitness/articles/how-biometric-monitoring-will-save-law-enforcement-lives-91PHTP83yHZNAOdw/#:~:text=These%20devices%20could%20be%20placed,monitoring%20program%20to%20other%20departments.

"Biometrics and Policing: A Protocol for Multichannel Sensor Data Collection and Exploratory Analysis of Contextualized Psychophysiological Response During Law Enforcement Operations", by Robert D Furberg et al., Published at JMIR Research Protocols, Published Online on [Mar. 17, 2017] https://pdfs.semanticscholar.org/e725/3d89aa98ffc8036163acdea18137db13464d.pdf.

"Real-Time Remote Health Monitoring Systems Using Body Sensor Information and Finger Vein Biometric Verification: A Multi-Layer Systematic Review", by A. H. Mohsin et al., Published at Journal of Medical Systems, Published Online On [Oct. 16, 2018] https://shorturl.at/IJPQ5.

"Warfighter Physiological and Environmental Monitoring", by G.A. Shaw et al., Published at Massachusetts Institute of Technology, Published Online On [Nov. 1, 2024] https://apps.dtic.mil/sti/tr/pdf/ADA428022.pdf.

"Wearable Health Devices—Vital Sign Monitoring, Systems and Technologies", by Duarte Dias et al., Published at Wearable Smart Devices, Published Online On [Jul. 25, 2018] https://www.mdpi.com/1424-8220/18/8/2414.

(56) References Cited

OTHER PUBLICATIONS

"On The Real-Time Prevention and Monitoring of Exertional Heat Illness in Military Personnel", by M.J. Buller, Published at Journal of Science and Medicine in Sport, Published Online On [Apr. 26, 2021] https://www.jsams.org/action/showPdf?pii=S1440-2440%2821%2900104-3.

"The Power of Biometrics: A Game-Changer for Officer Wellness", by Deputy Chief Aaron Johnson, Published at Police1, Published online on [Mar. 2, 2024] https://www.police1.com/wellness-week/the-power-of-biometrics-a-game-changer-for-officer-wellness.

"Wearable Tech for Law Enforcement", Published at inTime, Found Online on [May 3, 2024] https://intime.com/industries/police/wearable-tech-for-law-enforcement/.

"Can Body Cameras Reduce Altercations in a Correctional Facility?", by Dawn Lenzmeier, published at NEWCOM, Published Online On [Nov. 30, 2022] https://newcomglobal.com/wp-content/uploads/2022/11/NEWCOM-Body-Cameras-Reduce-Altercations-in-a-Correctional-Facility.pdf.

"Body Cameras in Corrections? Get ready For Game-Changing Benefits", Published at Utility, Published online on [Feb. 29, 2024] https://www.utility.com/blog/body-cameras-in-corrections-get-ready-for-game-changing-benefits/.

"Body-Worn Camera Activation in Prisons: Understanding Correctional Officers' Decision-Making and Use of Discretion", by Dodd, Published at Security Journal, Published Online on [May 26, 2023] https://research-repository.griffith.edu.au/server/api/core/bitstreams/b534906f-5064-4e5e-94a7-e0f8cf1c99a8/content.

"A Randomized Controlled Trial of the Impact of Body-Worn Cameras in the Loudoun County, VA, Adult Detention Center", by Brittany C. Cunningham et al., Published at CNA, Published Online In [Jun. 2023] https://www.ojp.gov/pdffiles1/nij/grants/307338.pdf.

"Body-Worn Camera Activation In Prisons: Understanding Correctional Officers' Decision-Making And Use Of Discretion", by Shanon Dodd et al., Published at Security Journal, Published On https://hizligecisodemesi.net/body-worn-camera-scholarly-articles-7cf3.

"Policing Universities: Exploring the use of body-worn cameras (BWCs) by private campus security officers", by Francesca Menichelli, Published at Policing and Society, Published Online on [Feb. 17, 2024] https://www.tandfonline.com/doi/epdf/10.1080/10439463.2024.2315583?needAccess=true.

"Transition of Body-Worn Cameras from Policing to Corrections", by Jasmine Kaur, Published at EBP Society, Published online On [Mar. 24, 2023] https://www.ebpsociety.org/blog/education/547-transition-of-body-worn-cameras-from-policing-to-corrections.

"Life-Saving Suits for Law Enforcement: Looking Ahead at Wearable Technology", by Thomas B. Cashion et al., Published at International Association of Chiefs of Police, Published Online on [Jun. 27, 2018] https://www.policechiefmagazine.org/life-saving-wearable-technology/.

"Policing Faces: The Present And Future of Intelligent Facial Surveillance", by Lachlan Urquhart et al., Published at Information & Communication Technology Law, Published online On [Oct. 28, 2021] https://www.pure.ed.ac.uk/ws/portalfiles/portal/239314767/UrquhartLMirandaD2021ICTLPolicingFaces.pdf.

"Hardware to Protect Against Drones", by Dedrone, Found Online On [May 3, 2024] https://www.dedrone.com/products/counter-drone-technology.

"Counter-Drone Solutions", ARDRONIS, Found Online On [May 3, 2024] https://www.rohde-schwarz.com/hk/products/aerospace-defense-security/counter-drone-systems_250881.html.

"Protectors of Critical Infrastructure are Enabled by Spotter Radars to Prevent Harm", by Spotter Global, Found Online On [May 3, 2024] https://www.spotterglobal.com/.

"Development of Equipment for Satellite Navigation Systems GLONASS, GPS, GALILEO", by KB Center, Found Online On [May 3, 2024] http://www.kbcentr.com.ua/.

"Design Smart Antenna for GPS/GLONASS Using Adaptive Beamforming", Herasymenko K.V. et al., Lviv Polytechnic National University Institutional Repository, Published Online In [Jan. 2012] https://shorturl.at/oslS5.

"Equipment Optimization For Weather Balloon and Ground-Based Weather Stations Using GNSS", by A. G. Laush, Published at International Conference on Antenna Theory and Techniques (ICATT), Published Online In [2017] https://sci-hub.yncjkj.com/10.1109/icatt.2017.7972662.

"A Novel Dual Band Microstrip Antenna Array for Receiving of Satellite Navigational Signals GPS/GLONASS/GALILEO", by Sergiy Y. Martynyuk et al., Published at International Conference on Antenna Theory and Techniques Published Online In [2015] https://sci-hub.yncjkj.com/10.1109/icatt.2015.7136781.

"Model of Mapping Function for The Calculation of Zenith Tropospheric Delay", by V.I. Lutsenko et al., Published at International Kharkov Symposium on Physics and Engineering of Microwaves, Millimeter and Submillimeter Waves, Published Online In [2013] https://sci-hub.53yu.com/10.1109/msmw.2013.6622052.

"IAP Software", by The Response Group, Published in [2003] https://www.responsegroupinc.com/iap.

"Next-Generation Incident Command System (NICS)", by Kontur, Found Online On [Mar. 12, 2024] https://www.kontur.io/portfolio/nics/.

"Next-Generation Incident Command System", by MIT Lincoln Laboratory, Found Online On [Mar. 12, 2024] https://www.ll.mit.edu/r-d/projects/next-generation-incident-command-system.

"Next-Generation Incident Command System Fact Sheet", by U.S. Department of Homeland Security, Published Online On [Jun. 5, 2024] https://www.dhs.gov/sites/default/files/publications/Next%20Generation%20Incident%20Command%20System-NICS_0.pdf.

"Response Tools", by NJ Resources, Found Online On [Mar. 12, 2024] https://njr.net/response-tools/.

"Axon Body 4", by Patrick W. Smith et al., Published In [1993] https://www.axon.com/products/axon-body-4.

"Digital Evidence Management, In-Car Video, and Advanced Body Cameras.", by Utility, Found Online On [Mar. 12, 2024] https://www.utility.com/.

"DisasterTech", by Roger Coleman et al., Published in [2019] https://www.disastertech.com/.

"Using Unmanned Aerial Vehicles (UAVs) as Mobile Sensing Platforms (MSPs) for Disaster Response, Civil Security and Public Safety", Published at Fundamental and Applied Research in Unmanned Aircraft Systems Technology, by Hanno Hildmann et al., Published Online On [Jul. 29, 2019] https://www.mdpi.com/2504-446X/3/3/59.

"Toward UAV-Based Airborne Computing", Published at IEEE Wireless Communications, by Kejie Lu et al., Published Online on [Aug. 5, 2019] https://par.nsf.gov/servlets/purl/10110848.

"Unmanned Aerial Vehicles for Wildland Fires: Sensing, Perception, Cooperation and Assistance", Published at Feature Papers of Drones, by Moulay A. Akhloufi et al., Published Online On [Feb. 22, 2021] https://www.mdpi.com/2504-446X/5/1/15.

"UAV-Enabled Disaster Management: Applications, Open Issues, And Challenges", Published at Journal of Field Robotics, by Amina Khan et al., Published Online On [Nov. 15, 2022] https://gmsarnjournal.com/home/wp-content/uploads/2023/06/vol18no1-6.pdf.

"Drone Swarms in Fire Suppression Activities: A Conceptual Framework", Published at UAV Application for Wildfire Detection, Prevention and Management, by Elena Ausonio et al., Published Online On [Mar. 7, 2021] https://www.mdpi.com/2504-446X/5/1/17.

"An Exploratory Study of the Use of Drones for Assisting Firefighters During Emergency Situations", Published at Conference on Human Factors in Computing Systems Proceedings, by Md. Nafiz Hasan Khan et al., Published Online On [May 2, 2019] http://clab.iat.sfu.ca/pubs/Khan-DronesFirefighters-CHI2019.pdf.

"The Good, the Bad and the Indispensable—Insights into the Practical Potential of Emergency Response Information Systems and Drones for Firefighters", Published at Hawaii International Conference on System Sciences, by Julian Weidinger, Published Online In [2018] https://core.ac.uk/download/pdf/143480849.pdf.

"Autonomous First Response Drone-Based Smart Rescue System for Critical Situation Management in Future Wireless Networks",

(56) References Cited

OTHER PUBLICATIONS

Published at Journal on Innovative Communication Technologies, by Joel P. Lemayian et al., Published Online On [May 23, 2020] https://assets.pubpub.org/ybmy2nbl/71604609477880.pdf.

"Tactile Feedback in Defence & Security: The Next Frontier", by Haptic, Published Online on [May 13, 2023] https://www.haptic.ro/tactile-feedback-in-defence-security-the-next-frontier/.

"Wearable Technologies for Law Enforcement", Published at National Istitute of Justice, by Richard Silberglitt et al., Published Online on [Sep. 8, 2017] https://www.rand.org/content/dam/rand/pubs/research_reports/RR2000/RR2012/RAND_RR2012.pdf.

"IoT based Smart Vest and Helmet for Defence Sector", Published at IEEE International Conference on Communication Information and Computing Technology, by Ninad V. Joshi, Published Online On [Jun. 25, 2021] https://shorturl.at/inKQ8.

Utilizing Glove-Based Gestures and a Tactile Vest Display for Covert Communications and Robot Control, Published at Army Research Laboratory, by Linda R. Elliott et al., Published Online in [2014] https://apps.dtic.mil/sti/pdfs/ADA607637.pdf.

"Wearable Technologies Can Help Soldiers Survive in Adverse Environment", Published at Chakraview, by Dr. Jayakrishnan N. Nair, Published Online On [Dec. 18, 2020] https://defence.capital/2020/12/18/wearable-technologies-can-help-soldiers-survive-in-adverse-environment/.

"IOT Based Soldier E-Jacket Using GPS", Published at Journal of Interdisciplinary Cycle Research, by Prof. Swapnil Chaudhari et al., Published Online In [Mar. 2020] https://shorturl.at/euRZ7.

"Police Body-Worn Cameras and Privacy: Views and Concerns of Officers and Citizens", Published at International Journal of Police Science & Management, by Brigitte Poirier et al., Published Online On [Nov. 21, 2023] https://journals.sagepub.com/doi/pdf/10.1177/14613557231214383.

"LORA Based Soldier Tracking and Health Monitoring Device", Published at International Research Journal of Engineering and Technology, by Kruthikaran et al., Published Online in [Mar. 2023] https://www.irjet.net/archives/V10/13/IRJET-V10I367.pdf.

"A Literature Review on IOT-Based Soldier Health Monitoring E-Jacket", Published at International Research Journal of Modernization in Engineering Technology and Science, by Ms. Dnyanada Meshram et al., Published Online in [Feb. 2023] https://www.irjmets.com/uploadedfiles/paper/issue_2_february_2023/33517/final/fin_irjmets1676464912.pdf.

"Body-Worn Cameras' Effects On Police Officers and Citizen Behavior: A Systematic Review", Published at Campbell Systematic Reviews, by Cynthia Lum et al., Published Online On [Sep. 9, 2020] https://onlinelibrary.wiley.com/doi/epdf/10.1002/cl2.1112.

"Enhancing Response Capabilities with Smartwatches in Public Safety", Published at The Public Safety Network, Found Online On [Mar. 12, 2024] https://www.publicsafety.network/wp-content/uploads/2021/01/Smartwatches-in-Public-Safety-White-Paper_FINAL.pdf.

"Police Tactical Vest: IoT and AI to Enhance Safety on Operations", Published at Mechatronics Canada, Published Online On [Mar. 1, 2024] https://www.mechatronicscanada.ca/product-news/police-tactical-vest-iot-ai/.

"Body-Worn Video Cameras for Law Enforcement Market Survey Report", Published at Homeland Security, Published Online In [Jun. 2015] https://www.dhs.gov/sites/default/files/publications/Body-Worn-Cams-MSR_0615-508_1.pdf.

"Police Body-Worn Cameras: Perceptions of Law Enforcement Leadership", Published at Springerlink, by John Ortiz Smykla, Oublished Online on [Dec. 4, 2015] https://link.springer.com/content/pdf/10.1007/s12103-015-9316-4.pdf.

"Geolocation Wearables for Enhanced Law Enforcement", Published at Utilities One, Published Online On [Nov. 15, 2023] https://utilitiesone.com/geolocation-wearables-for-enhanced-law-enforcement#anchor-0.

"Want to control your electronics with your tongue?", Published at ZDNET, by Jada Jones, Published Online On [May 13, 2023] https://www.zdnet.com/article/want-to-control-your-electronics-with-your-tongue-this-company-is-making-that-happen/.

"A Magnetic Wireless Tongue-Computer Interface", Published at IEEE Xplore, by Xueliang Huo et al., Published Online On [Jun. 11, 2007] https://www.researchgate.net/publication/4252014_A_Magnetic_Wireless_Tongue-Computer_Interface.

"A Hands-Free, Mouth Operated Joystick Computer Mouse Designed Specifically for Individuals With Disabled Hand Movement", by Quadlife, Published Online On [Sep. 17, 2020] https://quad.life/product.

"MouthPad Turns Your Tongue into a Mouse For Your Phone", Published at Engadget, by Cherlynn Low, Published Online On [Jan. 12, 2024] https://www.engadget.com/the-mouthpad-turns-your-tongue-into-a-mouse-for-your-phone-184541021.html?_fsig=dqmn468RIJE_pgKZXmlOHw -%7EA.

"Evaluation of the Tongue Drive System by Individuals with High-Level Spinal Cord Injury", Published at Conf Proc IEEE Eng Med Biol Soc, by Xueliang Huo et al., Published Online On [Mar. 12, 2024] https://www.ncbi.nlm.nih.gov/pmc/articles/PMC4467691/pdf/nihms698831.pdf.

"An Arch-Shaped Intraoral Tongue Drive System with Built-in Tongue-Computer Interfacing SoC", Published at Miniaturized Wireless Biosensors, by Hangue Park et al., Published Online On [Nov. 14, 2014] https://www.mdpi.com/1424-8220/14/11/21565.

* cited by examiner

COMMAND CENTER 302

NETWORK 140

UAV 136A

SUSPECT 800

WEARER 114

FOOT PURSUIT 850

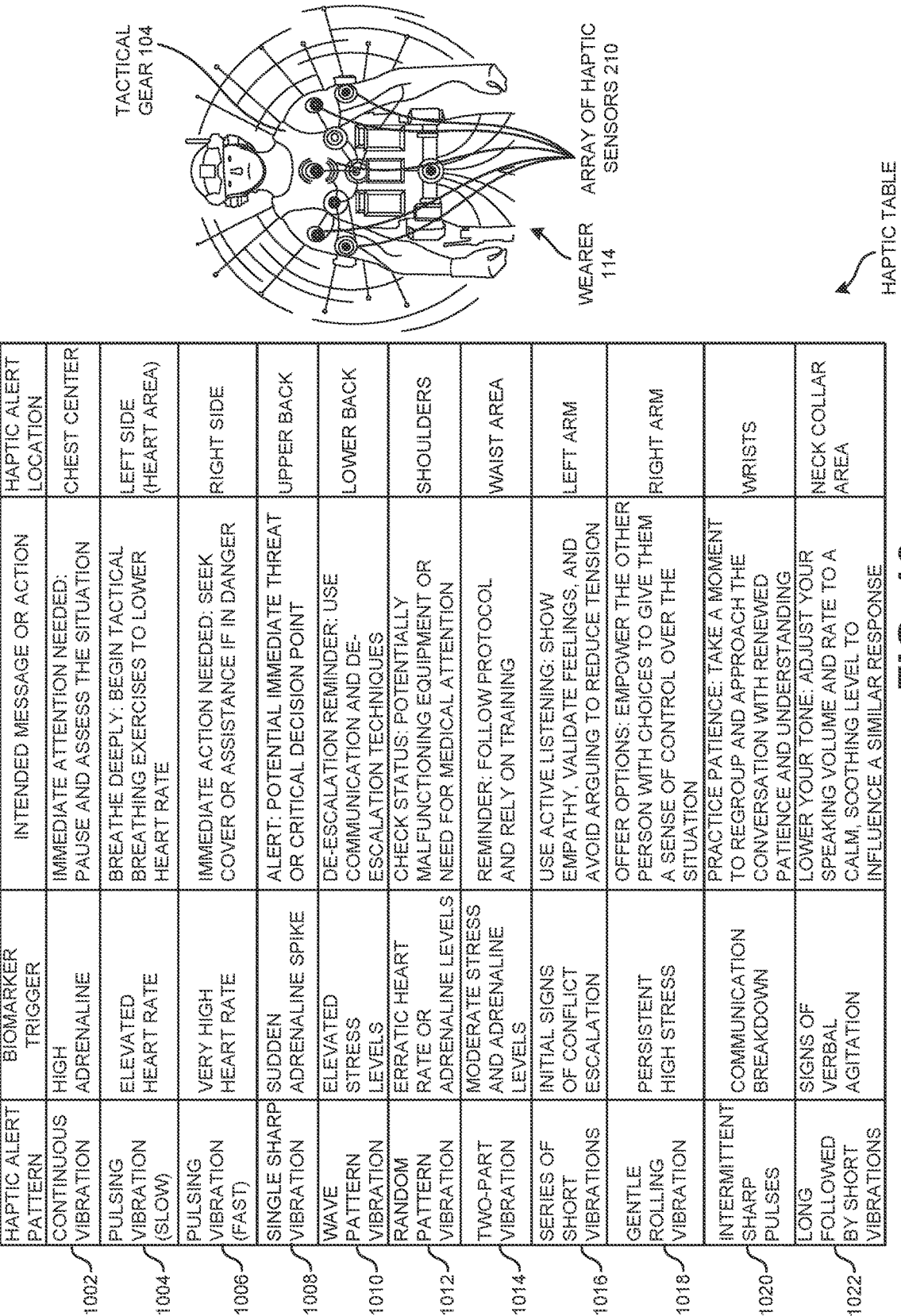

| HAPTIC ALERT PATTERN | BIOMARKER TRIGGER | INTENDED MESSAGE OR ACTION | HAPTIC ALERT LOCATION |
|---|---|---|---|
| CONTINUOUS VIBRATION | HIGH ADRENALINE | IMMEDIATE ATTENTION NEEDED: PAUSE AND ASSESS THE SITUATION | CHEST CENTER |
| PULSING VIBRATION (SLOW) | ELEVATED HEART RATE | BREATHE DEEPLY: BEGIN TACTICAL BREATHING EXERCISES TO LOWER HEART RATE | LEFT SIDE (HEART AREA) |
| PULSING VIBRATION (FAST) | VERY HIGH HEART RATE | IMMEDIATE ACTION NEEDED: SEEK COVER OR ASSISTANCE IF IN DANGER | RIGHT SIDE |
| SINGLE SHARP VIBRATION | SUDDEN ADRENALINE SPIKE | ALERT: POTENTIAL IMMEDIATE THREAT OR CRITICAL DECISION POINT | UPPER BACK |
| WAVE PATTERN VIBRATION | ELEVATED STRESS LEVELS | DE-ESCALATION REMINDER: USE COMMUNICATION AND DE-ESCALATION TECHNIQUES | LOWER BACK |
| RANDOM PATTERN VIBRATION | ERRATIC HEART RATE OR ADRENALINE LEVELS | CHECK STATUS: POTENTIALLY MALFUNCTIONING EQUIPMENT OR NEED FOR MEDICAL ATTENTION | SHOULDERS |
| TWO-PART VIBRATION | MODERATE STRESS AND ADRENALINE LEVELS | REMINDER: FOLLOW PROTOCOL AND RELY ON TRAINING | WAIST AREA |
| SERIES OF SHORT VIBRATIONS | INITIAL SIGNS OF CONFLICT ESCALATION | USE ACTIVE LISTENING: SHOW EMPATHY, VALIDATE FEELINGS, AND AVOID ARGUING TO REDUCE TENSION | LEFT ARM |
| GENTLE ROLLING VIBRATION | PERSISTENT HIGH STRESS | OFFER OPTIONS: EMPOWER THE OTHER PERSON WITH CHOICES TO GIVE THEM A SENSE OF CONTROL OVER THE SITUATION | RIGHT ARM |
| INTERMITTENT SHARP PULSES | COMMUNICATION BREAKDOWN | PRACTICE PATIENCE: TAKE A MOMENT TO REGROUP AND APPROACH THE CONVERSATION WITH RENEWED PATIENCE AND UNDERSTANDING | WRISTS |
| LONG FOLLOWED BY SHORT VIBRATIONS | SIGNS OF VERBAL AGITATION | LOWER YOUR TONE: ADJUST YOUR SPEAKING VOLUME AND RATE TO A CALM, SOOTHING LEVEL TO INFLUENCE A SIMILAR RESPONSE | NECK COLLAR AREA |

1002 1004 1006 1008 1010 1012 1014 1016 1018 1020 1022

TACTICAL GEAR 104

ARRAY OF HAPTIC SENSORS 210

WEARER 114

HAPTIC TABLE 1050

FIG. 10

| FUNCTION 1260 | GESTURE 1270 | DESCRIPTION 1280 |
|---|---|---|
| AERIAL RECONNAISSANCE | SWIPE UP | A QUICK SWIPE UP COMMANDS THE DRONE TO ASCEND TO A PREDEFINED ALTITUDE FOR A BROAD SURVEILLANCE VIEW. |
| CLOSE-UP INSPECTION | PINCH AND ZOOM IN | MIMICKING A CAMERA ZOOM, THIS GESTURE COMMANDS THE DRONE TO MOVE CLOSER TO A POINT OF INTEREST FOR DETAILED INSPECTION. |
| STATIC HOVER | PRESS AND HOLD | PRESSING AND HOLDING A SPOT ON THE TOUCHPAD INSTRUCTS THE DRONE TO HOVER IN ITS CURRENT POSITION, USEFUL FOR STEADY SURVEILLANCE OR WAITING FOR FURTHER INSTRUCTIONS. |
| FOLLOW WEARER | SINGLE TAP | COMMANDS THE DRONE TO START FOLLOWING THE OFFICER. |
| FOLLOW SUSPECT | DOUBLE TAP | COMMANDS THE DRONE TO START FOLLOWING THE IDENTIFIED SUSPECT. |
| FOLLOW SUSPECT VEHICLE | TRIPLE TAP | COMMANDS THE DRONE TO START TRACKING THE SUSPECT VEHICLE. |
| QUICK SHIFT TO SUSPECT | DRAW A 'V' | ALLOWS FOR A QUICK SHIFT IN THE DRONE'S FOCUS FROM FOLLOWING A SUSPECT VEHICLE TO FOLLOWING SUSPECT ON FOOT WITHOUT MANUAL RESELECTION. |
| DYNAMIC ADJUSTMENTS | DRAW AN 'S' | INSTRUCTS THE DRONE TO DYNAMICALLY ADJUST ITS FOLLOW PATTERN FOR OPTIMAL SURVEILLANCE, SUCH AS ALTERING ALTITUDE AND ANGLE. |
| STEALTH MODE FOR FOLLOWING | SWIPE DOWN WITH TWO FINGERS | ACTIVATES STEALTH MODE TO REDUCE THE DRONE'S VISIBILITY AND NOISE, MAKING IT LESS DETECTABLE BY THE SUSPECT. |
| TACTICAL POSITIONING AHEAD | DRAW A 'T' | COMMANDS THE DRONE TO POSITION ITSELF STRATEGICALLY AHEAD OF THE SUSPECT VEHICLE, ANTICIPATING ITS PATH FOR BETTER SURVEILLANCE AND COORDINATION WITH GROUND UNITS. |
| RETREAT AND RETURN | SWIPE DOWN | A SWIPE DOWN COMMANDS THE DRONE TO RETURN TO THE OFFICER OR RETURN TO BASE IF NEEDED FOR RECHARGING OR SAFETY. |

1202 1204 1206 1208 1210 1212 1214 1216 1218 1220 1222

HAPTIC GESTURE DIAGRAM 1250

FIG. 12

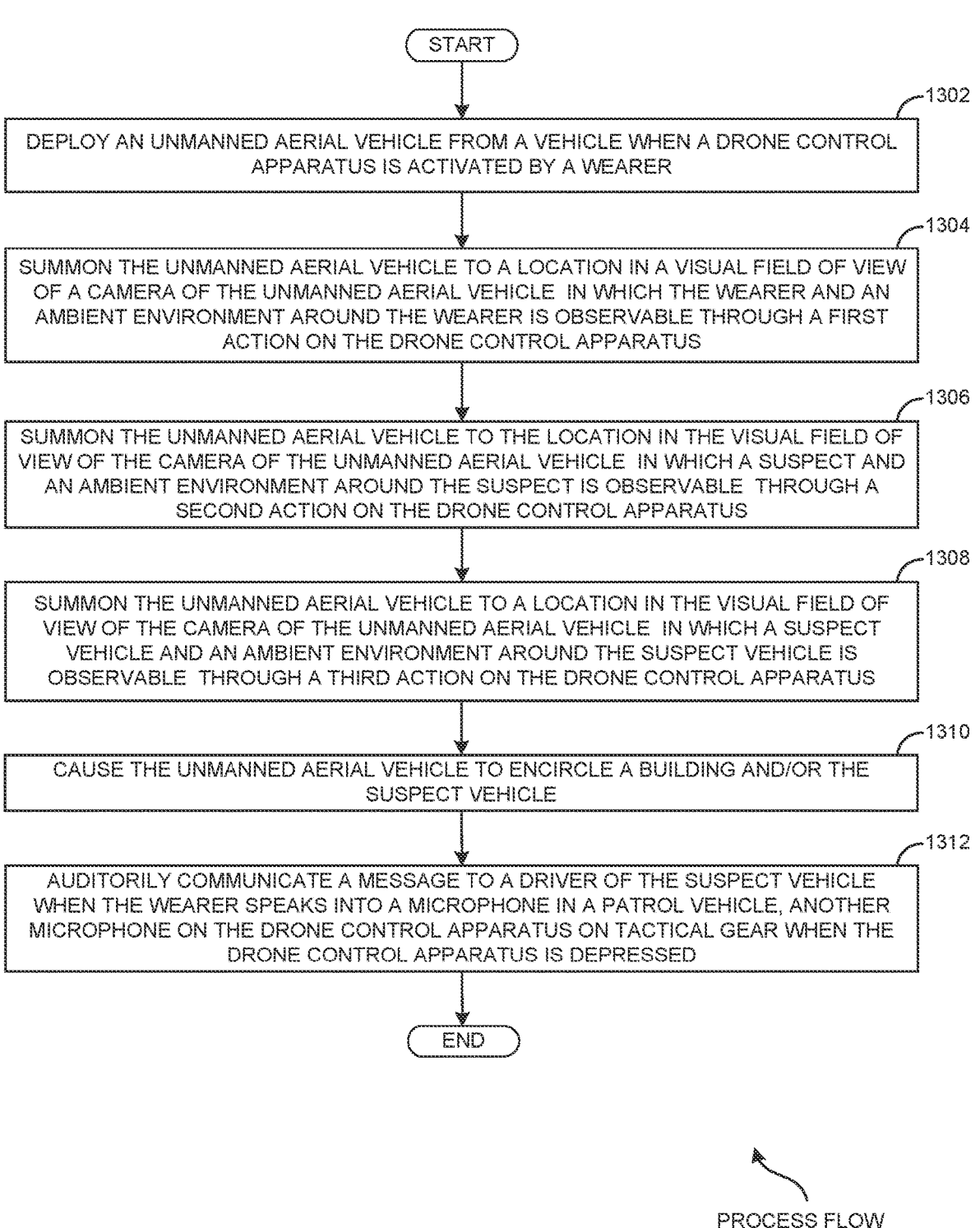

START

DEPLOY AN UNMANNED AERIAL VEHICLE FROM A VEHICLE WHEN A DRONE CONTROL APPARATUS IS ACTIVATED BY A WEARER ⌐1302

SUMMON THE UNMANNED AERIAL VEHICLE TO A LOCATION IN A VISUAL FIELD OF VIEW OF A CAMERA OF THE UNMANNED AERIAL VEHICLE  IN WHICH THE WEARER AND AN AMBIENT ENVIRONMENT AROUND THE WEARER IS OBSERVABLE THROUGH A FIRST ACTION ON THE DRONE CONTROL APPARATUS ⌐1304

SUMMON THE UNMANNED AERIAL VEHICLE TO THE LOCATION IN THE VISUAL FIELD OF VIEW OF THE CAMERA OF THE UNMANNED AERIAL VEHICLE  IN WHICH A SUSPECT AND AN AMBIENT ENVIRONMENT AROUND THE SUSPECT IS OBSERVABLE  THROUGH A SECOND ACTION ON THE DRONE CONTROL APPARATUS ⌐1306

SUMMON THE UNMANNED AERIAL VEHICLE TO A LOCATION IN THE VISUAL FIELD OF VIEW OF THE CAMERA OF THE UNMANNED AERIAL VEHICLE  IN WHICH A SUSPECT VEHICLE AND AN AMBIENT ENVIRONMENT AROUND THE SUSPECT VEHICLE IS OBSERVABLE  THROUGH A THIRD ACTION ON THE DRONE CONTROL APPARATUS ⌐1308

CAUSE THE UNMANNED AERIAL VEHICLE TO ENCIRCLE A BUILDING AND/OR THE SUSPECT VEHICLE ⌐1310

AUDITORILY COMMUNICATE A MESSAGE TO A DRIVER OF THE SUSPECT VEHICLE WHEN THE WEARER SPEAKS INTO A MICROPHONE IN A PATROL VEHICLE, ANOTHER MICROPHONE ON THE DRONE CONTROL APPARATUS ON TACTICAL GEAR WHEN THE DRONE CONTROL APPARATUS IS DEPRESSED ⌐1312

END

PROCESS FLOW
1350

FIG. 13

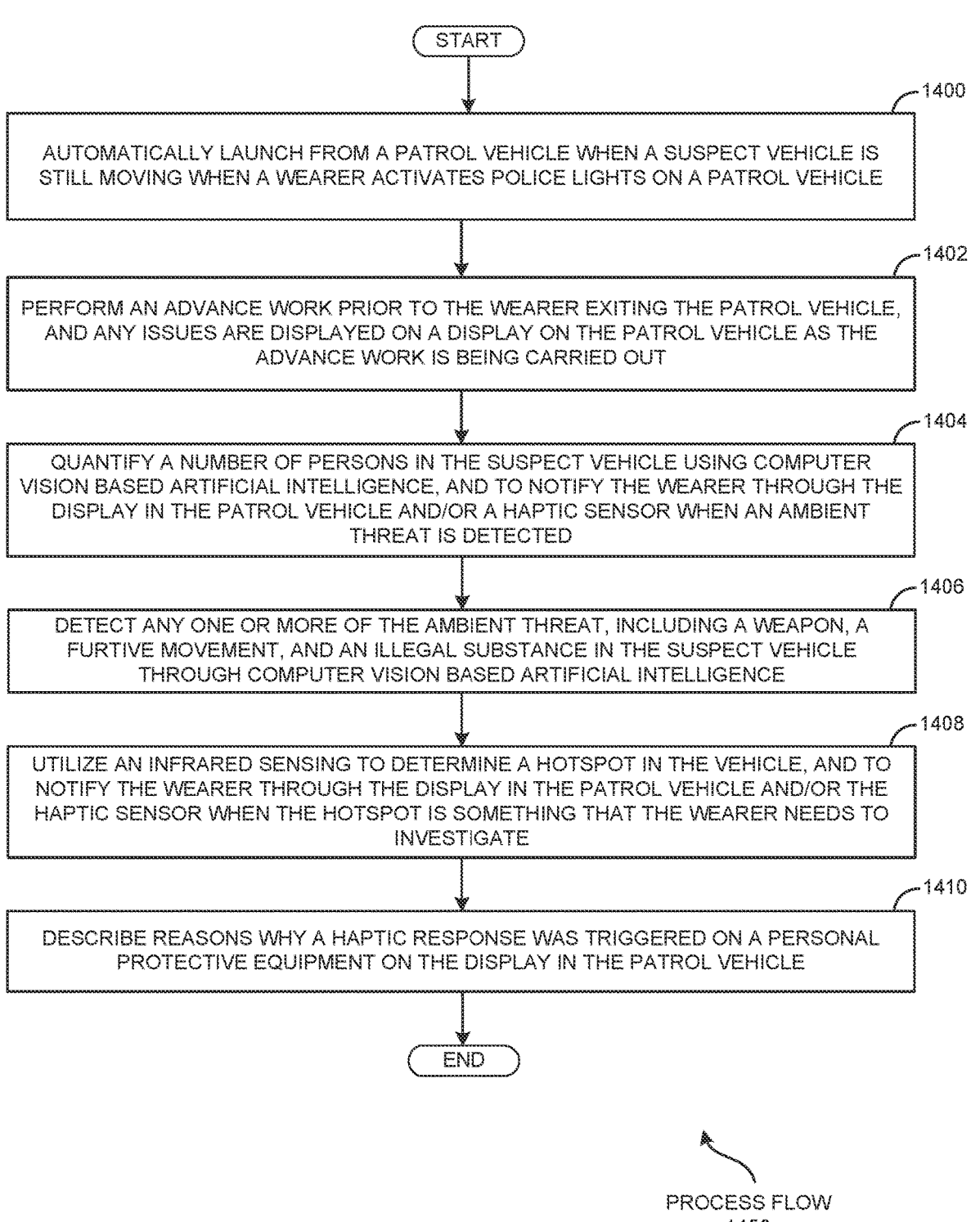

START

1400

AUTOMATICALLY LAUNCH FROM A PATROL VEHICLE WHEN A SUSPECT VEHICLE IS STILL MOVING WHEN A WEARER ACTIVATES POLICE LIGHTS ON A PATROL VEHICLE

1402

PERFORM AN ADVANCE WORK PRIOR TO THE WEARER EXITING THE PATROL VEHICLE, AND ANY ISSUES ARE DISPLAYED ON A DISPLAY ON THE PATROL VEHICLE AS THE ADVANCE WORK IS BEING CARRIED OUT

1404

QUANTIFY A NUMBER OF PERSONS IN THE SUSPECT VEHICLE USING COMPUTER VISION BASED ARTIFICIAL INTELLIGENCE, AND TO NOTIFY THE WEARER THROUGH THE DISPLAY IN THE PATROL VEHICLE AND/OR A HAPTIC SENSOR WHEN AN AMBIENT THREAT IS DETECTED

1406

DETECT ANY ONE OR MORE OF THE AMBIENT THREAT, INCLUDING A WEAPON, A FURTIVE MOVEMENT, AND AN ILLEGAL SUBSTANCE IN THE SUSPECT VEHICLE THROUGH COMPUTER VISION BASED ARTIFICIAL INTELLIGENCE

1408

UTILIZE AN INFRARED SENSING TO DETERMINE A HOTSPOT IN THE VEHICLE, AND TO NOTIFY THE WEARER THROUGH THE DISPLAY IN THE PATROL VEHICLE AND/OR THE HAPTIC SENSOR WHEN THE HOTSPOT IS SOMETHING THAT THE WEARER NEEDS TO INVESTIGATE

1410

DESCRIBE REASONS WHY A HAPTIC RESPONSE WAS TRIGGERED ON A PERSONAL PROTECTIVE EQUIPMENT ON THE DISPLAY IN THE PATROL VEHICLE

END

PROCESS FLOW
1450

FIG. 14

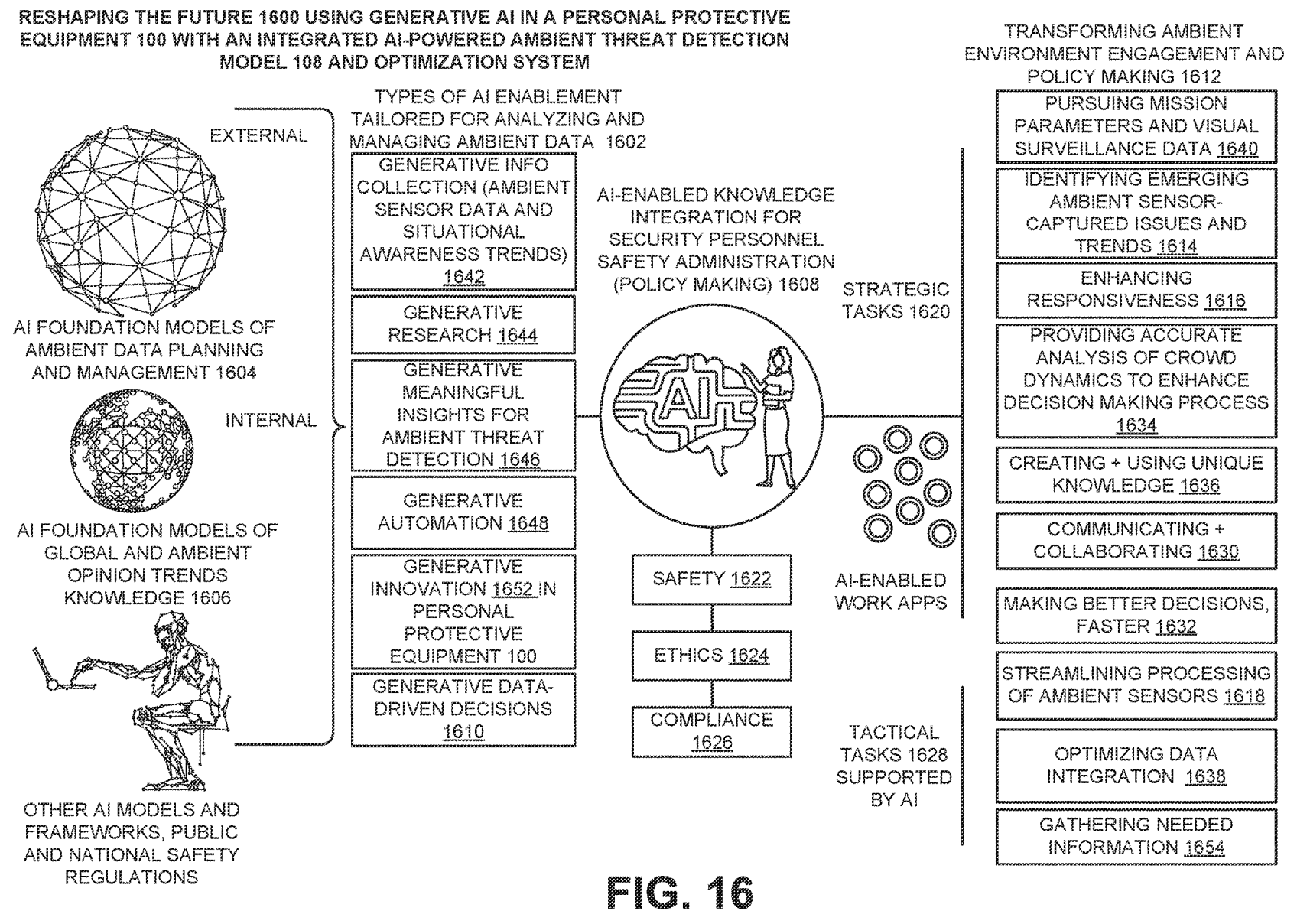

TRANSFORMING AMBIENT ENVIRONMENT ENGAGEMENT AND POLICY MAKING 1612

PURSUING MISSION PARAMETERS AND VISUAL SURVEILLANCE DATA 1640

IDENTIFYING EMERGING AMBIENT SENSOR-CAPTURED ISSUES AND TRENDS 1614

ENHANCING RESPONSIVENESS 1616

PROVIDING ACCURATE ANALYSIS OF CROWD DYNAMICS TO ENHANCE DECISION MAKING PROCESS 1634

CREATING + USING UNIQUE KNOWLEDGE 1636

COMMUNICATING + COLLABORATING 1630

MAKING BETTER DECISIONS, FASTER 1632

STREAMLINING PROCESSING OF AMBIENT SENSORS 1618

OPTIMIZING DATA INTEGRATION 1638

GATHERING NEEDED INFORMATION 1654

STRATEGIC TASKS 1620

AI-ENABLED WORK APPS

TACTICAL TASKS 1628 SUPPORTED BY AI

RESHAPING THE FUTURE 1600 USING GENERATIVE AI IN A PERSONAL PROTECTIVE EQUIPMENT 100 WITH AN INTEGRATED AI-POWERED AMBIENT THREAT DETECTION MODEL 108 AND OPTIMIZATION SYSTEM

TYPES OF AI ENABLEMENT TAILORED FOR ANALYZING AND MANAGING AMBIENT DATA 1602

AI-ENABLED KNOWLEDGE INTEGRATION FOR SECURITY PERSONNEL SAFETY ADMINISTRATION (POLICY MAKING) 1608

GENERATIVE INFO COLLECTION (AMBIENT SENSOR DATA AND SITUATIONAL AWARENESS TRENDS) 1642

GENERATIVE RESEARCH 1644

GENERATIVE MEANINGFUL INSIGHTS FOR AMBIENT THREAT DETECTION 1646

GENERATIVE AUTOMATION 1648

GENERATIVE INNOVATION 1652 IN PERSONAL PROTECTIVE EQUIPMENT 100

GENERATIVE DATA-DRIVEN DECISIONS 1610

SAFETY 1622

ETHICS 1624

COMPLIANCE 1626

EXTERNAL

INTERNAL

AI FOUNDATION MODELS OF AMBIENT DATA PLANNING AND MANAGEMENT 1604

AI FOUNDATION MODELS OF GLOBAL AND AMBIENT OPINION TRENDS KNOWLEDGE 1606

OTHER AI MODELS AND FRAMEWORKS, PUBLIC AND NATIONAL SAFETY REGULATIONS

FIG. 16

② PERSONAL PROTECTIVE EQUIPMENT 100 LISTENS IN OTHER LANGUAGE 2202 AND TRANSLATES TO PRIMARY LANGUAGE 2208 OF THE WEARER 114

PRIMARY LANGUAGE 2208

OTHER LANGUAGE 2202

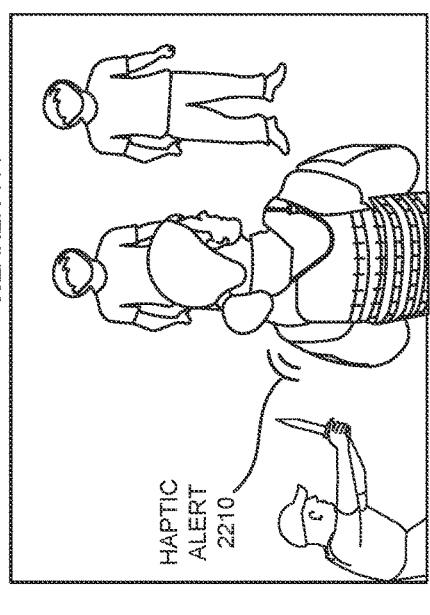

④ HAPTIC ALERT 2210 ONCE A WEAPON 132B NEARBY TO THE WEARER 114

HAPTIC ALERT 2210

① WEARER 114 PRESSES BUTTON 2204 TO TRANSLATE

AMBIENT ENVIRONMENT 2200

WEARER 114

ACTIVATE BUTTON 2204 ON LANGUAGE TRANSLATOR MODULE 144

OTHER LANGUAGE 2202

INDIVIDUAL(S) 2206

③ PERSONAL PROTECTIVE EQUIPMENT 100 LISTENS IN PRIMARY LANGUAGE 2208 AND TRANSLATES TO OTHER LANGUAGE 2202, BI-DIRECTIONAL COMMUNICATION

2202

2208

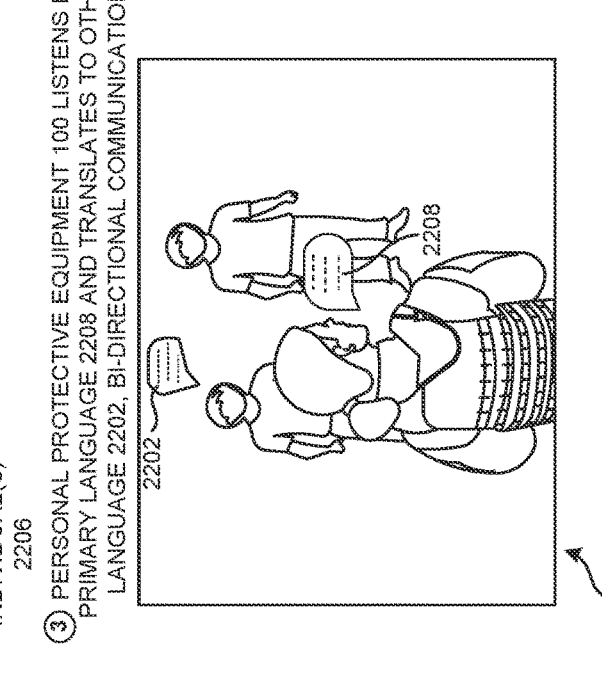

TRANSLATION VIEW 2250

FIG. 22

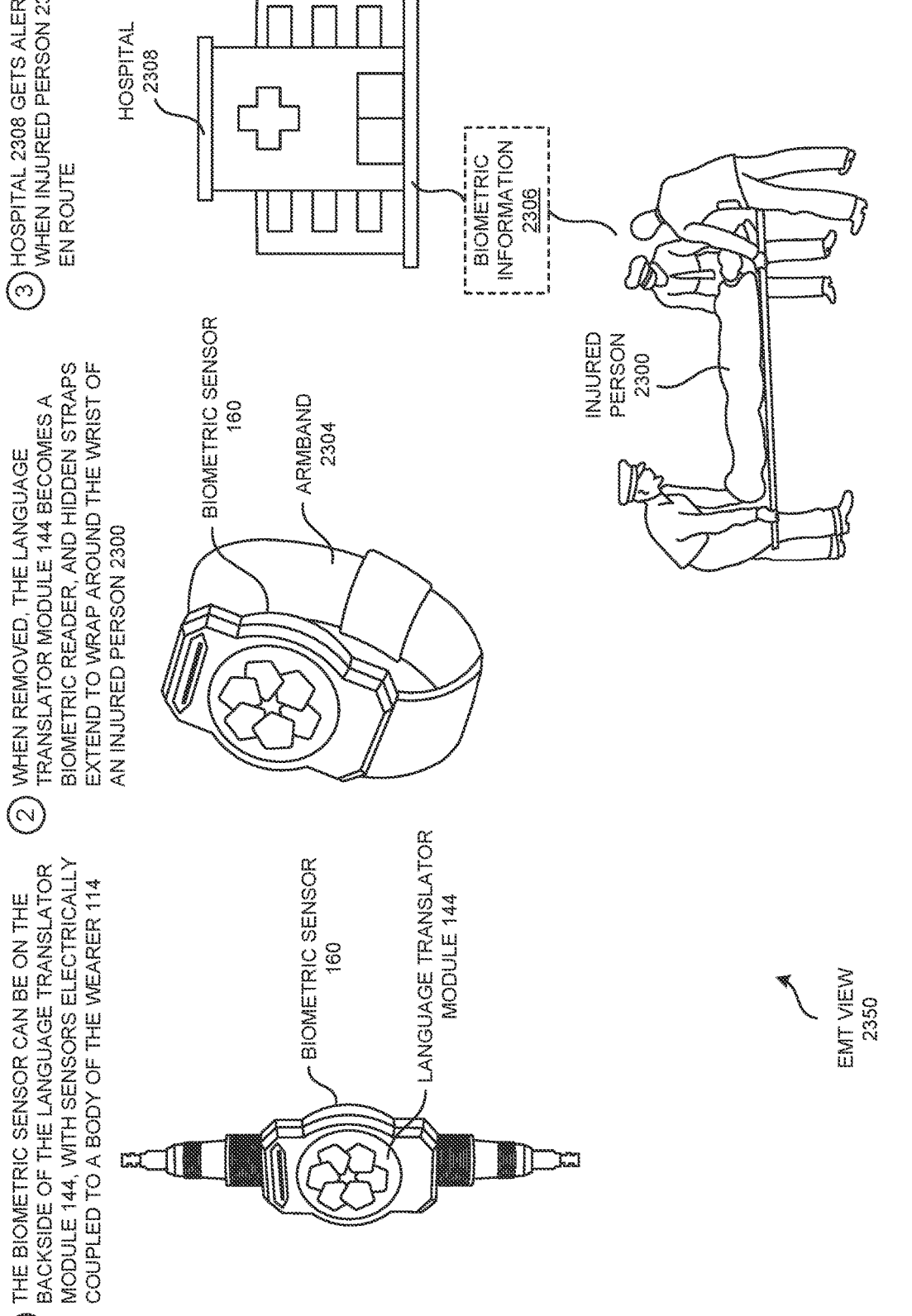

① THE BIOMETRIC SENSOR CAN BE ON THE BACKSIDE OF THE LANGUAGE TRANSLATOR MODULE 144, WITH SENSORS ELECTRICALLY COUPLED TO A BODY OF THE WEARER 114

BIOMETRIC SENSOR 160

LANGUAGE TRANSLATOR MODULE 144

② WHEN REMOVED, THE LANGUAGE TRANSLATOR MODULE 144 BECOMES A BIOMETRIC READER, AND HIDDEN STRAPS EXTEND TO WRAP AROUND THE WRIST OF AN INJURED PERSON 2300

BIOMETRIC SENSOR 160

ARMBAND 2304

③ HOSPITAL 2308 GETS ALERTS WHEN INJURED PERSON 2300 EN ROUTE

HOSPITAL 2308

BIOMETRIC INFORMATION 2306

INJURED PERSON 2300

EMT VIEW 2350

FIG. 23

| TYPE OF CONTRABAND 2500 | HAPTIC FEEDBACK PATTERN 2604 (E.G., HAPTIC RESPONSE 400) | DESCRIPTION |
|---|---|---|
| TOBACCO AND CIGARETTES | SINGLE LONG VIBRATION | A SINGLE, SUSTAINED VIBRATION SIGNALS THE DETECTION OF TOBACCO PRODUCTS, DISTINGUISHING IT FROM MORE IMMEDIATE THREATS |
| DRUGS AND ALCOHOL | RAPID, SHORT BURSTS | A SERIES OF QUICK VIBRATIONS INDICATES THE POTENTIAL PRESENCE OF DRUGS OR ALCOHOL, REQUIRING IMMEDIATE ATTENTION DUE TO THEIR HIGH CONTRABAND VALUE AND DANGER |
| MOBILE PHONES | TWO LONG VIBRATIONS | TWO CONSECUTIVE LONG VIBRATIONS ALERT TO THE DETECTION OF AN UNAUTHORIZED MOBILE PHONE, SUGGESTING COVERT COMMUNICATION ATTEMPTS |
| WEAPONS | CONTINUOUS RAPID PULSING | A FAST, PULSATING VIBRATION WARNS OF THE MOST IMMEDIATE PHYSICAL THREAT, SUGGESTING THE PRESENCE OF A WEAPON. |
| MONEY AND CURRENCY | TRIPLE SHORT VIBRATION | THREE SHORT VIBRATIONS INDICATE THE MOVEMENT OR EXCHANGE OF MONEY OR ITEMS USED AS CURRENCY, POTENTIALLY FOR CONTRABAND TRANSACTIONS. |
| INFORMATION | SINGLE VIBRATION FOLLOWED BY TWO SHORT BURSTS | A UNIQUE PATTERN THAT SIGNIFIES THE POTENTIAL EXCHANGE OF INFORMATION, NECESSITATING FURTHER INVESTIGATION FOR CONTEXT |
| MEDICATIONS | FOUR SHORT VIBRATIONS | FOUR QUICK VIBRATIONS ALERT OFFICERS TO THE UNAUTHORIZED HANDLING OR DISTRIBUTION OF MEDICATIONS, WHICH MAY INDICATE MISUSE OR TRADING |
| CLOTHING AND BEDDING | LONG VIBRATION FOLLOWED BY A SHORT BURST | A PATTERN INDICATING NON-STANDARD CLOTHING OR BEDDING, WHICH MAY SIGNAL UNAUTHORIZED POSSESSION OR STATUS SYMBOLS WITHIN THE INMATE POPULATION |
| FOOD AND SNACKS | TWO VIBRATIONS FOLLOWED BY A LONG BURST | ALERTS TO THE SMUGGLING OR UNAUTHORIZED EXCHANGE OF FOOD ITEMS, POTENTIALLY INDICATING TRADE OR REWARD SYSTEMS AMONG INMATES |
| ENTERTAINMENT | FIVE SHORT VIBRATIONS | A SERIES OF FIVE SHORT VIBRATIONS SIGNALS THE PRESENCE OF UNAUTHORIZED ENTERTAINMENT ITEMS, WHICH COULD BE USED FOR LEISURE OR TRADE. |

TACTICAL GEAR 104

WEARER 114

ARRAY OF HAPTIC SENSORS 210

HAPTIC TABLE 2650

| BEHAVIORS DISPLAYED BY GANG MEMBERS 2602 | HAPTIC FEEDBACK PATTERN 2604 |
|---|---|
| 2606 COMMUNICATION THROUGH SYMBOLS | A SERIES OF SHORT, QUICK VIBRATIONS |
| 2608 FORMATION OF CLIQUES | TWO LONG VIBRATIONS |
| 2610 RECRUITMENT | A PATTERN OF ONE LONG VIBRATION FOLLOWED BY TWO SHORT ONES |
| 2612 TERRITORIALITY | CONTINUOUS VIBRATION FOR A FEW SECONDS. |
| 2614 ENGAGEMENT IN CONTRABAND TRADE. | RAPID, INTERMITTENT BURSTS OF VIBRATIONS |
| 2616 VIOLENCE OR THREATS | A VERY FAST, PULSATING VIBRATION |
| 2618 PROTECTION RACKETS | THREE SHORT VIBRATIONS FOLLOWED BY ONE LONG VIBRATION |
| 2620 RITUALS | A UNIQUE PATTERN OF ALTERNATING LONG AND SHORT VIBRATIONS |
| 2622 UNEXPLAINED INJURIES | SINGLE, PROLONGED VIBRATION |
| 2624 LIMPING OR DIFFICULTY MOVING | TWO SHORT VIBRATIONS FOLLOWED BY A LONG ONE |
| 2626 SIGNS OF SELF-HARM | A SERIES OF GENTLE, YET RAPID VIBRATIONS |
| 2628 CHANGES IN PHYSICAL APPEARANCE | ALTERNATING PATTERNS OF SHORT VIBRATIONS |
| 2630 WITHDRAWAL | SLOW, FADING VIBRATIONS MIMICKING THE ACT OF WITHDRAWING |
| 2632 CHANGES IN BEHAVIOR | ERRATIC VIBRATION PATTERNS |
| 2634 SELF-HARM | A DISTINCT PATTERN OF SHORT, SHARP VIBRATIONS |
| 2636 SUBSTANCE ABUSE | CONTINUOUS, LOW-INTENSITY VIBRATIONS |
| 2638 CHANGES IN COMMUNICATION | A PATTERN OF VIBRATIONS STARTING HIGH AND TAPERING OFF |
| 2640 PHYSICAL SYMPTOMS OF STRESS | A MEDIUM-INTENSITY, STEADY PULSING VIBRATION |

FIG. 26

BIOMETRIC SENSOR OF A TACTICAL GEAR TO MONITOR HEALTH AND STRESS OF A WEARER

CLAIM OF PRIORITY

This Application is a conversion Application of, claims priority to, and incorporates by reference herein the entirety of the disclosures of:

U.S. Provisional Patent Application No. 63/614,022 titled MULTI-FUNCTIONAL WEARABLE AI-ENABLED PENDANT APPARATUS, SYSTEM, AND METHOD OF AMBIENT DATA ANALYSIS AND COMMUNI-CATION IN LAW ENFORCEMENT, FIRE, MEDI-CAL RESPONDER, PRIVATE SECURITY, JOUR-NALISM, COMMERCIAL AND MILITARY OPERATIONAL ENVIRONMENTS filed on Dec. 22, 2023;

U.S. Provisional Patent Application No. 63/616,817 titled EMOTIONALLY INTELLIGENT AERIAL DRONE SYSTEM FOR ENHANCED SITUATIONAL AWARENESS AND RESPONSIVE OPERATIONS filed on Jan. 1, 2024;

U.S. Provisional Patent Application No. 63/622,514 titled HAPTIC FEEDBACK RESPONSIVE TO A THREAT IDENTIFIED THROUGH A GENERATIVE ARTIFI-CIAL INTELLIGENCE BODY WORN APPARATUS filed on Jan. 18, 2024;

U.S. Provisional Patent Application No. 63/626,075 titled SECURE EDGE MESH NETWORK SYSTEM FOR ENHANCED VISUAL INTERPRETATION AND REAL-TIME SITUATIONAL AWARENESS IN COMBAT ZONES filed on Jan. 29, 2024;

U.S. Provisional Patent Application No. 63/552,265 titled MODULAR INTEGRATED BODY CAMERA SYS-TEM FOR ENHANCED ERGONOMICS, OPERA-TIONAL EFFICIENCY, AND TECHNOLOGICAL ADAPTABILITY IN LAW ENFORCEMENT EQUIP-MENT filed on Feb. 12, 2024;

U.S. Provisional Patent Application No. 63/552,277 titled MARITIME SURVEILLANCE AND ASSISTANCE SYSTEM USING A DEPLOYABLE DRONE FLEET filed on Feb. 12, 2024;

U.S. Provisional Patent Application No. 63/555,014 titled TRAUMATIC INJURY COMMUNICATION METH-ODOLOGY AND SYSTEM THROUGH A BODY WORN DEVICE filed on Feb. 17, 2024;

U.S. Provisional Patent Application No. 63/554,380 titled INTERACTIVE VOICE-ACTIVATED DEVICE TO IMPROVE PATIENT CARE AND OUTCOMES IN VETERAN AND CIVILIAN HEALTHCARE ENVI-RONMENTS filed on Feb. 16, 2024;

U.S. Provisional Patent Application No. 63/554,360 titled ENHANCED SITUATIONAL AWARENESS THROUGH A HAPTIC WEARABLE DEVICE OF A POLICE OFFICER OR A WARFIGHTER, ACTI-VATED BY A NEARBY NETWORKED VEHICLE OR A STATIONARY SENSOR UPON DETECTING A THREAT filed on Feb. 16, 2024; and U.S. Utility patent application Ser. No. 18/596,684 titled BODY SAFETY DEVICE WITH VISUAL SENSING AND HAPTIC RESPONSE USING ARTIFICIAL INTELLIGENCE filed on Mar. 6, 2024.

FIELD OF TECHNOLOGY

The present disclosure relates generally to the field of wearable personal safety technology. This disclosure relates generally to a biometric sensor of a tactical gear to monitor health and stress of a wearer.

BACKGROUND

When a police officer is in an agitated state with adrena-line running high, such as after intense scenarios like a high-speed chase, several negative outcomes can arise that may impact decision-making, behavior, and overall effec-tiveness. High adrenaline levels can narrow an individual's focus, potentially impairing judgment and the ability to assess situations accurately. This might lead to misinterpret-ing a situation or missing critical information.

In the heat of the moment, officers might overestimate a threat or react more aggressively than necessary, which could escalate a situation unnecessarily. The physical effects of adrenaline can push the body beyond its normal limits, leading to exhaustion or, in extreme cases, health issues such as heart problems. The physiological responses to stress and adrenaline can impair fine motor skills, affecting an officer's ability to perform tasks that require precision, such as operating equipment or administering first aid. Stress and adrenaline can amplify emotional responses, such as anger or fear, which may not be conducive to calm and rational decision-making.

Prolonged exposure to high-stress situations can lead to long-term psychological effects, including post-traumatic stress disorder (PTSD), anxiety, and depression. Stress and adrenaline can affect an officer's ability to communicate effectively, both with colleagues and civilians. This might lead to misunderstandings or conflicts. In situations requir-ing teamwork, an agitated state can hinder coordination and cooperation among officers, potentially compromising the success of an operation. Actions taken in a highly agitated state can be perceived negatively by the public, especially if they result in unnecessary use of force or harm to civilians. This can erode trust in law enforcement.

Decisions made under the influence of adrenaline and stress can have legal repercussions for the officer and the department, including lawsuits and disciplinary actions. There's an increased risk of resorting to physical force or using weapons, which might not only endanger the officer but also civilians and suspects. The probability of injuries to the officer, suspects, and bystanders escalates in situations where decisions are made under extreme stress or adrenaline influence.

SUMMARY

Disclosed are a method, system, and apparatus of a biometric sensor of a tactical gear to monitor health and stress of a wearer.

In one aspect, a personal protective equipment includes a language translator module integrated in a tactical gear, a biometric sensor, and a responsive device integrated in the tactical gear. A wearer bi-directionally communicates with an individual in an ambient environment using any language other than a primary language spoken by the wearer when the language translator module is activated. The biometric sensor detects a health condition of the wearer. The responsive device vibrates when the biometric sensor detects an elevated stress level of the wearer of the tactical gear. The elevated stress level may be detected through a heart rate monitor which determines whether a heart rate of the wearer is beyond an acceptable range. The heart rate monitor may evaluate a heart rate variability (HRV) which is a variation in time between each heartbeat. A lower HRV may be an indicator of the elevated stress level.

The biometric sensor may be a galvanic skin response (GSR) skin conductance sensor to measure an electrical conductance of a skin of the wearer which increases with sweat gland activity. A higher electrical conductance may indicate the elevated stress level. The biometric sensor may be a blood pressure sensor to detect a temporary spike in blood pressure that indicates the elevated stress level. The responsive device may detect the elevated stress level using an artificial intelligence-based threat detection model. The artificial intelligence-based threat detection model may also detect and/or analyze human emotion of the individual in an ambient area to the wearer using computer vision and/or auditory sensing to detect the presence or absence of an ambient threat. The responsive device may be part of an array of haptic sensors to vibrate at different locations of a body of the wearer depending on a directional location of the ambient threat. An intensity of vibration of the array of haptic sensors may be dependent on a proximity of the ambient threat to the wearer. A pattern of vibration of the responsive device may be dependent on a type of ambient threat to the wearer. The biometric sensor may automatically document a health condition of the wearer and/or communicate that information to a command center and/or a hospital. The biometric sensor may be detachable from the tactical gear and/or placeable on an injured person nearby to the wearer through an armband extendable from the biometric sensor when it is removed from the tactical gear. The biometric sensor may automatically communicate the biometric information of the injured person and/or the wearer to the hospital when removed from the tactical gear and/or placed on an arm of the injured person when the injured person is en route to the hospital. The personal protective equipment may communicate without electronic signature through a non-radiative, human-body-centered communication network.

In another aspect, a personal protective equipment includes a biometric sensor of a tactical gear to detect a health condition of a wearer of the tactical gear and a responsive device integrated in the tactical gear to notify the wearer through vibration when the biometric sensor detects an elevated stress level of the wearer of the tactical gear.

In yet another aspect, a personal protective equipment includes a biometric sensor of a tactical gear to detect a health condition of a wearer and a responsive device to vibrate when the biometric sensor detects an elevated stress level of the wearer of the tactical gear. The biometric sensor is detachable from the tactical gear and placeable on an injured person nearby to the wearer through an armband extendable from the biometric sensor when it is removed from the tactical gear. The biometric sensor automatically communicates a biometric information of the injured person and/or the wearer to a hospital when removed from the tactical gear and placed on an arm of the injured person, when the injured person is en route to the hospital.

The methods and systems disclosed herein may be implemented in any means for achieving various aspects, and may be executed in a form of a non-transitory machine-readable medium embodying a set of instructions that, when executed by a machine, cause the machine to perform any of the operations disclosed herein. Other features will be apparent from the accompanying drawings and the detailed description that follows.

BRIEF DESCRIPTION OF THE DRAWINGS

The embodiments of this invention are illustrated by way of example and not limitation in the figures of the accompanying drawings, in which like references indicate similar elements and in which:

FIG. 10 is a haptic table associated with an array of haptic sensors on the tactical gear to reduce stress of the wearer and remind of mindfulness, when the biometric sensor(s) detect elevated stress markers on a wearer, according to one embodiment.

FIG. 12 is a haptic gesture diagram, depicting various haptic gestures to control the drone control apparatus, according to one embodiment.

FIG. 13 is a process flow describing a series of operations of the drone control apparatus, according to one embodiment.

FIG. 14 is a process flow describing a series of operations the drone system may automatically take when launched from a vehicle (e.g., armored carrier, patrol vehicle), according to one embodiment.

FIG. 16 illustrates the innovative application of "Generative AI in Personal Protective Equipment Management using an Integrated Threat Detection Model," as conceptualized in one embodiment of the GovGPT™ personal protective equipment of FIG. 1, according to one embodiment.

FIG. 22 is a translation view illustrating a bi-directional communication of a wearer of the body safety device of FIG. 1 illustrating communication with a group of individuals in an ambient environment using any language other than a primary language spoken by the wearer when the language translator module is activated by the wearer, according to one embodiment.

FIG. 23 is a medical emergency view illustrating a biometric sensor on a back side of the language translator module and touching a skin of the wearer of the body safety device of FIG. 1, and wherein the entire assembly is detachable and attachable to a wrist of an injured person through a hidden armband to communicate information biometric information to a hospital, according to one embodiment.

FIG. 25 is a table view illustrating haptic response associated with the array of haptic sensors on the tactical gear of FIG. 1 to generate different haptic feedback for each type of detected contraband in a correctional facility, according to one embodiment.

FIG. 26 is a haptic table associated with the array of haptic sensors on the tactical gear of FIG. 1 to generate different haptic patterns for each type of behaviors displayed by gang members detected on the tactical gear, according to one embodiment.

Other features of the present embodiments will be apparent from the accompanying drawings and from the detailed description that follows.

DETAILED DESCRIPTION

Disclosed are a method, system, and apparatus of a biometric sensor of a tactical gear to monitor health and stress of a wearer. The GovGPT TraumaScribe™ leverages a powerful combination of biometric sensors, computer vision, auditory data interpretation through generative artificial intelligence to ensure safety of a wearer and timely notification to a hospital and/or a command center, according to one embodiment. The GovGPT TraumaScribe™ can record audio and visual data during stressful events, addressing mental and physical concerns during police and military engagements, according to one embodiment. The TraumaScribe™ automatically timestamps and geocodes locations of all recorded data, providing an accurate and indisputable record of when specific events occurred, according to one embodiment. This feature can be valuable for command centers and medical personnel who rely on the timing of treatments (such as relieving of duty and ordering of an ambulance) to make informed decisions about tactical strategies and medical interventions, according to one embodiment.

The methods and systems disclosed herein may be implemented in any means for achieving various aspects, and may be executed in a form of a non-transitory machine-readable medium embodying a set of instructions that, when executed by a machine, cause the machine to perform any of the operations disclosed herein. Other features will be apparent from the accompanying drawings and the detailed description that follows.

Figure 1:
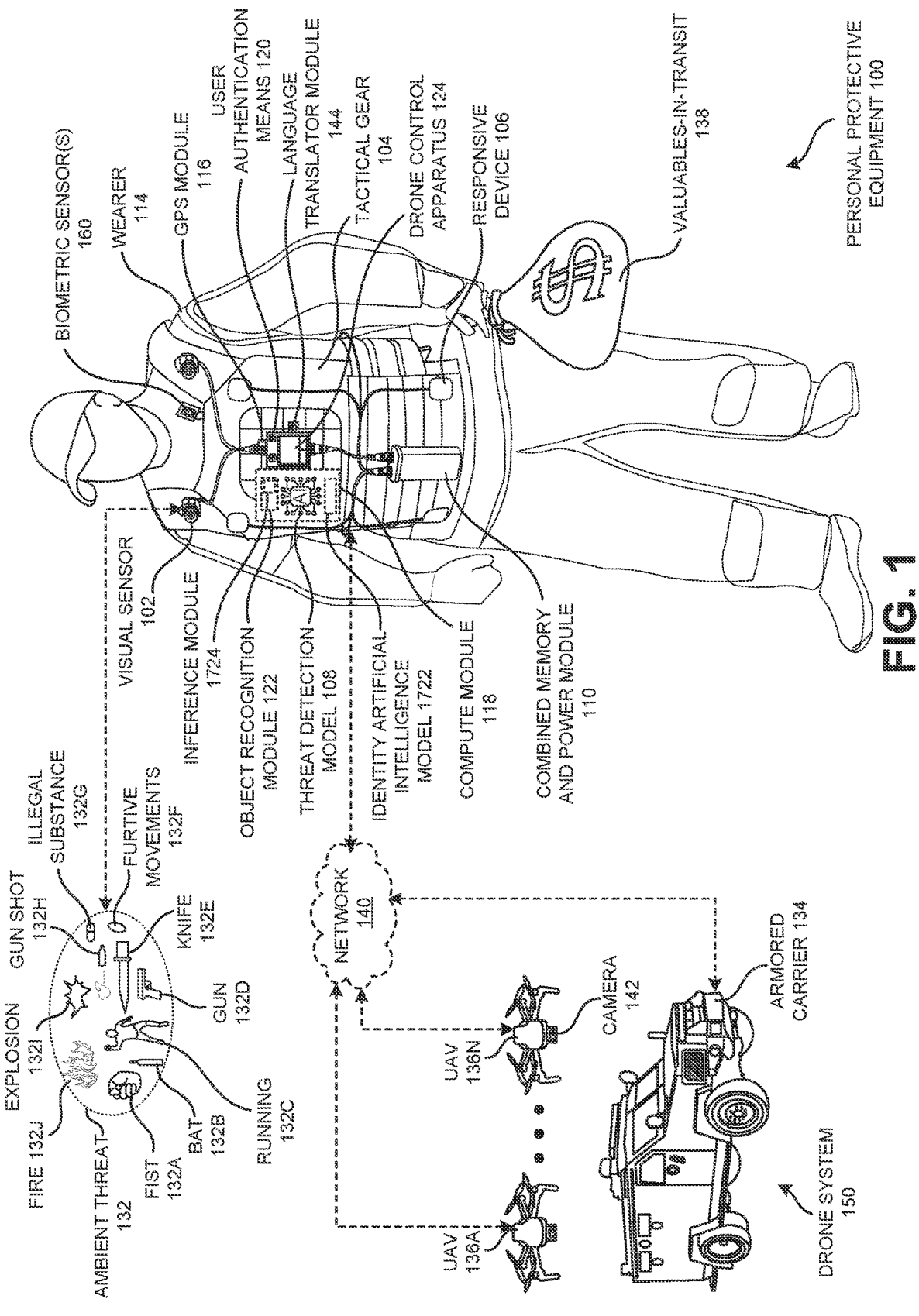
FIG. 1 is a system view of a person wearing a tactical gear having a drone control apparatus to operate a drone system that is networked with the tactical gear and a responsive device on the tactical gear to notify a wearer when an ambient threat to the wearer is detected using computer vision-based artificial intelligence by an unmanned aerial vehicle ("UAV") of the drone system, according to one embodiment.

FIG. 1 is a system view of a person wearing a tactical gear 104 having a drone control apparatus 124 to operate a drone system 150 that is networked (e.g., through network 140) with the tactical gear 104 and a responsive device 106 on the tactical gear 104 to notify when an ambient threat 132 is detected using computer vision-based artificial intelligence (e.g., using the compute module 118) by an unmanned aerial vehicle ("UAV") 136 of the drone system 150, according to one embodiment.

The tactical gear 104 may be any wearable torso covering apparel designed for military and/or law enforcement purposes to enhance the efficiency, safety, and capability of the wearer 114 during operations, such as a tactical vest or a tactical carrier. Tactical gear 104, encompassing tactical vests, inner vests, and carriers, may include a wide range of equipment designed for military, law enforcement, and security personnel, and for civilian use in certain contexts like hunting, shooting sports, and outdoor activities. Tactical vest embodiments of tactical gear 104 may be designed to carry essential gear and provide quick access to ammunition, communications devices, and medical kits, and may have multiple pockets and pouches for organization, according to one embodiment. Tactical carrier embodiments of tactical gear 104 may be plate carriers specifically designed to hold ballistic armor plates for protection against bullets and shrapnel, and may also carry additional gear, according to one embodiment. Tactical gear 104 may also include body armor including stab-proof vests, bulletproof vests and/or other garments (worn inside a uniform or outside a uniform) designed to protect against ballistic and/or sharp object threats. In one embodiment, tactical gear 104 may include ghillie suits and camo netting for blending into the environment during surveillance and/or hunting. In an alternative embodiment, the tactical gear 104 may not have ballistic, stab-proof, or bullet proof protection, but may be a simple garment having the various haptic and visual sensors (e.g., array of visual sensors 200, array of haptic sensors 210) described herein, according to one embodiment.

The visual sensor 102 may be a device integrated into a tactical gear 104 capable of detecting ambient threats 132 through visual inputs, functioning in various lighting conditions to enhance the wearer's situational awareness. Object recognition module 122 may be a computational unit within the system that analyzes visual data from the visual sensor 102 to identify objects and classify them, potentially as threats or non-threats. Threat detection model 108 may be one or more artificial intelligence algorithms designed to analyze inputs from the visual sensor 102 and/or other modules to identify potential threats in the environment surrounding the wearer 114. Compute module 118 may be the main processing unit that executes the software algorithms, including threat detection and object recognition, to analyze data collected by the system's sensors. Combined memory and power module 110 may be a unit that provides both power to the device's components and storage for data captured by the system, such as visual recordings and sensor data. The wearer 114 may be a person equipped with the tactical gear 104 that incorporates the personal protective equipment 100, who benefits from enhanced situational awareness and threat detection, according to one embodiment.

The user authentication means 120 may be a security feature ensuring that the device's functionalities are accessible only by verified users, possibly through biometric verification or a digital passcode. GPS module 116 may be a component that offers geolocation capabilities, enabling the device to track the wearer's position and potentially record the locations of detected threats. Tactical gear 104 may be a wearable garment that houses the visual sensor 102, responsive device 106, and other modules (e.g., object recognition module 122, compute module 118, a combined memory and power module 110, GPS module 116, a threat detection model 108, etc.), designed for use in security, military, or emergency response scenarios. In one embodiment, the tactical gear 104 having the sensor array may be a gear carrier in which a standard bullet proof gear may be inserted, according to one embodiment.

The distinguishing feature of this embodiment of FIG. 1 lies in the drone system 150. The drone system 150 comprises a set of UAVs 136 that are launched from a vehicle, including but not limited to the armored carrier 134 as shown in FIG. 1. Each UAV 136 may include different sensors and components depending on the use case and need, according to one embodiment. Each UAV 136 may include a camera 142, according to one embodiment.

Another feature of the embodiment of FIG. 1, is the incorporation of the optional array of visual sensors 200, one of which is labeled as visual sensor 102, according to one embodiment. While FIG. 1 illustrates two visual sensors 102 positioned on either shoulder area, it is important to note that this arrangement is not always required. Visual sensors may be in just one shoulder, or they may be in neither (e.g., in a center neck or chest area is possible). In addition, the tactical gear 104 may house multiple visual sensors 102 on both the front area 204 and back area 214 of the tactical gear 104, offering 360 degree surveillance capabilities, according to one embodiment. These visual sensors, akin to cameras, may possess the ability to operate in low-light conditions, utilizing advanced visual processing capability technology or similar low-light detection mechanisms, according to one embodiment. Rather than principally recording video footage, their primary function is to detect ambient threats (e.g., 132A-132J) in the wearer's vicinity, according to one embodiment.

The term "ambient threats," referenced as number 132 in FIG. 1, encompasses various potential dangers, as depicted in FIG. 1, according to one embodiment. These threats include but are not limited to a first 132A, a bat 132B, running 132C, a gun 132D, a knife 132E, furtive movements 132F, illegal substance 132G, gun shot 132H, explosion 132I, and fire 132J, according to one embodiment. In the context of ambient threat 132 to a wearer 114, particularly law enforcement officers or security personnel equipped with tactical gear 104 and engaged in operations, recognizing approaching indicators and visual cues may be crucial for assessing potential threats and determining the appropriate response, according to one embodiment. These indicators, often subtle, may provide early warnings of an individual's intentions, allowing officers to preemptively address situations before they escalate into physical confrontations, according to one embodiment.

Approaching Indicators/Visual Cues

Hands in the Pocket Approaching: An individual approaching with hands in pockets may be concealing a weapon or preparing to deploy it, according to one embodiment. This behavior may warrant caution and preparedness for a quick defensive response, according to one embodiment.

Facial Expressions: Expressions such as pressing lips together, jaw crunching, and squinting eyes may often indicate stress, determination, or aggression, according to one embodiment. Observing these may signal an officer (e.g., wearer 114) to the heightened emotional state of the individual, potentially leading to aggressive actions, according to one embodiment.

Disgust, Anger, Frustration: These emotional displays may escalate to physical confrontation, according to one embodiment. Recognizing these emotions allows officers to deploy de-escalation techniques early, according to one embodiment.

Pupil Dilation: Often a physiological response to emotional arousal, fear, or intention to be aggressive, dilated pupils may serve as a cue to the officer (e.g., wearer 114) about the individual's heightened state of alertness or aggression, according to one embodiment.

Making Their Hand into a first 132A: This is a preparatory gesture for a physical attack and may serve as a clear warning sign of potential aggression, according to one embodiment.

Scanning: When an individual alternately walks toward and away from an officer while scanning the surroundings, it may indicate planning an escape route or assessing the environment for an advantage in a potential confrontation, according to one embodiment.

Body Angling: An individual angling their body towards an officer may be positioning themselves for a physical altercation or to gain leverage in an attack (e.g., called "blading," it can also be an indicator that a person is armed), according to one embodiment.

Raising Shoulder and Chest, Stretching Exercises: These actions may indicate an individual is psyching themselves up for a confrontation, increasing their physical presence or preparing their body for a fight, according to one embodiment.

Looking Foot to Head (Sizing Up the Cop): This visual scanning may often be used to assess an officer's physical capabilities, vulnerabilities, and equipment, possibly in preparation for a confrontation, according to one embodiment.

Looking Left and Right: This behavior may indicate nervousness, looking for escape routes, or seeking the presence of law enforcement backups or witnesses before engaging in a confrontational act, according to one embodiment.

Sudden Change in Voice Pitch or Volume: An abrupt change in the tone or loudness of a person's voice may indicate stress, anger, or imminent aggression, according to one embodiment. Higher pitch and louder volume often signal an escalation in emotional intensity, according to one embodiment.

Excessive Sweating: While this may be attributed to various factors, in a confrontational or high-stress situation, excessive sweating may indicate nervousness, stress, or fear, potentially signaling that an individual is preparing for aggressive action, according to one embodiment.

Rapid Breathing: This physiological response may signify anxiety, fear, or aggression. Observing an increase in someone's breathing rate may indicate a heightened emotional state or preparation for physical exertion, according to one embodiment.

Avoiding Eye Contact or Intense Staring: Either avoiding eye contact entirely or engaging in prolonged, intense staring may be indicators of aggression, according to one embodiment. The former may signal a desire to hide intentions, while the latter can be an attempt to intimidate, according to one embodiment.

Exaggerated Yawning or Stretching: While seemingly innocuous, these behaviors in certain contexts may be a way to display dominance, prepare physically for action, or mask nervousness, according to one embodiment.

Tapping Feet or Fidgeting: Signals restlessness or impatience, which, in confrontational scenarios, may indicate a buildup of aggressive energy or a readiness to act, according to one embodiment.

Repeated Touching of Face or Head: This nervous habit may signal lying, anxiety, or stress, potentially indicating that an individual is uncomfortable with the situation and may be considering escalation, according to one embodiment.

Clenching Jaw or Grinding Teeth: Beyond being a sign of stress or anger, this may also be a preparatory action for physical confrontation, signifying that an individual is bracing for aggression, according to one embodiment.

Abrupt Movements or Changes in Posture: Sudden, jerky movements or quickly changing posture may indicate that an individual is gearing up for aggressive actions or trying to assert dominance, according to one embodiment.

Mirroring Officer Movements: If an individual begins to subtly mimic the movements of an officer, it may be a sign of attempted intimidation or preparation for a physical altercation, according to one embodiment.

Concealing One Side of the Body or Shuffling: This behavior may indicate that an individual is concealing a weapon on their person and is possibly positioning themselves to use it, according to one embodiment, according to one embodiment.

Excessive Swearing or Threatening Language: Verbal cues may also serve as indicators of aggression, according to one embodiment. An increase in swearing, threats, or hostile language may signal an escalation towards physical confrontation, according to one embodiment.

Adjusting Clothing or Accessories Frequently: This behavior may indicate nervousness or the concealment of weapons or contraband, according to one embodiment. Frequent adjustments may be a pretext to reach for a concealed item, according to one embodiment.

Foot Tapping or Shifting Weight from One Foot to Another: Signs of impatience, nervousness, or preparing to sprint or move quickly, possibly to initiate an attack or flee, according to one embodiment.

Covering Mouth or Touching Face: Often a sign of deception or nervousness, according to one embodiment. When coupled with other indicators, it may suggest an intent to mislead or hide true intentions, according to one embodiment.

Crossed Arms with Tense Muscles: While sometimes a sign of mere discomfort or self-soothing, in certain contexts, it may indicate defensiveness or resistance to engagement, signaling a potential for escalation if approached, according to one embodiment.

Unusual Posture Adjustments: Sudden or exaggerated adjustments in posture, such as puffing up the chest or overly straightening the back, may be attempts to appear more dominant or intimidating, according to one embodiment.

Physiological Response: The system may utilize thermal imaging cameras (e.g., body worn camera 216) and infrared sensors integrated into tactical gear 104 or UAV 136 to capture subtle changes in body temperature and perspiration levels of individuals within a monitored area, according to one embodiment. These sensors may be sensitive enough to detect increased heat emissions and visible signs of sweating, which are physiological indicators of elevated heart rates and potential pre-assaultive behavior or medical emergency, according to one embodiment. The core of this system may be an AI model (e.g., compute model 118) trained in computer vision techniques to interpret the data collected by thermal and infrared sensors accurately, according to one embodiment. This AI model may analyze patterns of heat and perspiration to distinguish between normal, non-threatening physiological states and those that might precede aggressive actions or be correlated to a heart attack requiring immediate medical attention, according to one embodiment. Upon detecting a suspect 800 exhibiting signs of elevated heat emission and perspiration indicative of a potential threat and/or medical emergency, the system may automatically classify the individual as the suspect 800 of interest or requiring medical attention and triggers an alert, according to one embodiment. Security personnel equipped with the system may receive discreet notifications through their tactical gear 104, possibly via haptic feedback or through a heads-up display (HUD) showing the location and basic information about the individual identified by the AI model, according to one embodiment. The system may guide responding wearer 114 with recommended approaches or interventions, leveraging historical data and predictive modeling to suggest actions that minimize the risk of escalation, according to one embodiment.

The tactical gear 104, including the integration of visual sensor 102, UAV 136 surveillance and artificial intelligence, may assist officers in recognizing and responding to these cues, according to one embodiment. Visual sensor 102, and UAV 136 equipped with advanced sensors may detect subtle physiological and behavioral indicators from a distance, providing officers with an additional layer of situational awareness. Artificial intelligence may analyze these cues in real-time, alerting the wearer 114 through haptic feedback or visual signals on their tactical gear or associated displays, according to one embodiment. This advanced warning system may allow officers to adjust their stance, call for backup, initiate de-escalation protocols, or prepare for defensive measures as needed, according to one embodiment.

Incorporating the detection of precursors to potentially aggressive or evasive actions into the functionality of a tactical gear 104 may involve leveraging a combination of sensors and AI-driven analysis to interpret human behavior and bodily cues in real-time, according to one embodiment. The tactical gear 104, equipped with advanced technology, may analyze these precursors and provide haptic feedback to the wearer, thereby alerting them to potential threats before they fully manifest, according to one embodiment.

Detection of Precursors:

Pick Up the Pants or Tie Up Their Laces: The tactical gear sensors (e.g., responsive device 106, visual sensor 102, etc.), potentially including visual or motion sensors integrated with UAV support, may detect sudden movements or specific gestures associated with preparing to run or engage in physical conflict, according to one embodiment. These actions, such as adjusting one's pants or tying shoelaces, are analyzed by the vest's onboard AI to determine their context and potential threat level, according to one embodiment.

21-Foot Rule Awareness: The tactical gear 104 system may incorporate training data on the 21-foot rule, enabling it to gauge the distance between the officer and an individual armed with a knife, shank, or similar weapon, according to one embodiment. Utilizing GPS module 116, motion sensors, and possibly LIDAR technology, the system may accurately measure distances in real-time, alerting the officer when someone enters this critical range, thereby increasing their risk, according to one embodiment.

Removing Footwear: Similar to detecting adjustments in clothing, the tactical gear 104 system may recognize motions or posture changes indicative of a person removing high heels or sandals, interpreted as preparations for a confrontation or flight, according to one embodiment. This may be detected through a combination of visual recognition technologies and movement analysis algorithms, according to one embodiment.

Sudden Stop in Movement: The tactical gear 104 sensors may detect when an individual who has been moving erratically suddenly stops, which might indicate a decision point or preparation for an aggressive action, according to one embodiment.

Rapid Eye Movement or Blink Rate: Utilizing facial recognition or eye-tracking technology, the system may interpret increased blink rates or rapid eye movement as signs of stress, deception, or the intent to initiate an aggressive action, according to one embodiment.

Hand Gestures Towards Waistband or Jacket: Movements towards areas where weapons are commonly concealed may be detected by visual sensors, indicating a potential draw of a weapon, according to one embodiment.

Sudden Group Convergence: The detection of multiple individuals suddenly converging on a location may indicate a coordinated action or ambush, according to one embodiment. This may be detected through motion sensors and AI analysis of crowd behavior, according to one embodiment.

Change in Vocal Tonality Detected by Audio Sensors: The integration of audio sensors may allow the system to detect changes in vocal pitch, volume, or tone that often accompany aggressive intent or heightened stress, according to one embodiment.

Abnormal Breathing Patterns: Through sound analysis or body sensors on tactical gear 104 or the UAVs 136, the system may detect changes in breathing patterns that may indicate stress, fear, or preparation for physical exertion, according to one embodiment.

Quick Repeated Glancing in a Specific Direction: Indicative of looking for escape routes or the arrival of accomplices, detected through motion or visual sensors analyzing head movements, according to one embodiment.

Rapid Dismount from a Vehicle: Sudden movements associated with exiting a vehicle quickly, which may be detected by a combination of visual and motion sensors, indicating a potential for immediate confrontation or flight, according to one embodiment.

Unusual Posture Adjustments: Detecting through visual sensors, signs of someone adjusting their stance in a way that is common before initiating a physical attack or running, according to one embodiment.

Discrete Signaling Between Individuals: Recognizing subtle signals or gestures between individuals that may indicate coordination or premeditation of an aggressive action, according to one embodiment.

Crowd Noise Analysis: The AI system is designed to recognize shifts in crowd noise that may indicate distress, panic, or the onset of a potentially dangerous situation, according to one embodiment. By analyzing patterns in sound level, frequency, and disruption within ambient noise, the AI may identify anomalies that precede incidents, allowing for preemptive action, according to one embodiment.

Keyword Detection in Multiple Languages: Recognizing the diverse linguistic landscape of urban cities, the AI is programmed to detect keywords or phrases in various languages that may signify a threat or call for help, according to one embodiment. This feature may particularly be useful traffic stops or drug raids, enabling them to pick up spoken cues, according to one embodiment. Integrated into the officer's gear, this module may capture spoken language in the vicinity of the officer, leveraging directional microphones to focus on specific sources of speech, such as a suspect 800 or group of individuals (e.g., number of persons 912), according to one embodiment. This engine may process the captured audio in real-time (e.g., optionally translating it to the officer's preferred language) and analyzing it for specific keywords or phrases known to be pre-assault indicators or threats, according to one embodiment. This analysis relies on an extensive, dynamically updated database of terms and phrases associated with aggressive behavior or intent across multiple languages, according to one embodiment.

Upon detection of specific keywords or phrases indicating imminent threat, the system may immediately alert the officer (e.g., wearer 114) through visual, haptic and/or auditory signals on their personal device or the tactical gear's heads-up display, according to one embodiment. Key phrases or threats detected may be relayed back to a command center 302 or support units in real-time, providing them with situational awareness and the ability to respond appropriately, including dispatching additional resources or guidance, according to one embodiment. All translated conversations and identified keywords/phrases are automatically documented and timestamped (e.g., using real-time data 1112), providing invaluable evidence for later analysis, reporting, or legal proceedings, according to one embodiment. By identifying potential threats before they escalate into physical actions, officers can take preventative measures, increasing their safety and the safety of bystanders, according to one embodiment. The ability to understand and analyze any language in real-time may help the officers to overcome language barriers, ensuring that suspects cannot exploit language differences to their advantage, according to one embodiment.

Prior Assaultive Conduct: Historical data from previous police encounters to inform the real-time evaluation of potential threats when the tactical gear 104 interfaces with Computer-Aided Dispatch (CAD), Records Management Systems (RMS), and other relevant criminal databases, according to one embodiment. This component may establish secure, real-time access to CAD, RMS, and other pertinent databases, according to one embodiment. It may retrieve data related to the individuals (e.g., suspect 800) currently being interacted with or observed, focusing on their history of violence, resistance to arrest, possession or use of weapons, and other relevant factors, according to one embodiment. By leveraging AI and machine learning, the engine may analyze historical data in conjunction with real-time inputs (including the translated conversations and identified verbal pre-assault indicators) to assess the potential threat levels, according to one embodiment. The engine may consider patterns of behavior, the context of previous encounters, and any notes indicating a propensity for violences, according to one embodiment. Based on the analysis, the system may generate a threat level indicator, which is visualized on the display 604 of the patrol vehicle 700, the officer's heads-up display or another accessible interface, according to one embodiment. This indicator may provide a quick, understandable reference that combines historical data insights with real-time situational awareness, according to one embodiment.

When the system identifies an individual with a significant history of violence or resistance, it may alert the wearer 114 with a personalized threat level indicator. This alert may include a brief summary (e.g., using AI summary 1106) of relevant historical data, enabling the officer to approach the situation with appropriate caution and tactics, according to one embodiment. Depending on the assessed threat level, the system may suggest tailored response protocols, ranging from calling for backup to deploying non-lethal measures preemptively, according to one embodiment. These protocols may be dynamically adjusted based on the ongoing situation and any new information gathered, according to one embodiment. All interactions, threat assessments, and responses may be automatically documented within the system, including the rationale for the threat level assigned, according to one embodiment. This documentation may be invaluable for post-incident analysis, training, and legal proceedings, according to one embodiment. The system may incorporate a feedback mechanism, allowing the wearer 114 to provide input on the accuracy and usefulness of the threat assessments, according to one embodiment. This feedback may be used to continuously refine the analytics algorithms, improving the system's effectiveness over time, according to one embodiment.

Implementation and Operation of the Embodiments of Personal Protective Equipment 100 are Described Below:

Integration with Aerial and Ground Systems: The sound and language identification capabilities may be integrated into both tactical gear 104 or the UAVs 136, according to one embodiment. Drones flying over events or crowded areas may capture audio, which is then processed in real-time by the AI to identify potential threats or distress signals, according to one embodiment.

Real-time Alerts and Response Coordination: Upon detecting a significant sound pattern or keyword, the tactical gear 104 or the UAVs 136 system may generate alerts (e.g., haptic response 400) that are communicated to the security team, according to one embodiment. The alerts may be specific, indicating the nature of the detected anomaly and its location, enabling targeted responses. For example, if the AI identifies the sound pattern of a crowd suddenly running or keywords associated with a fight, security personnel may quickly mobilize to the exact location, according to one embodiment.

Gait Pattern Recognition: Utilizing the visual sensors already incorporated into tactical gear 104 or the UAVs 136, the system may employ advanced algorithms to analyze the gait patterns of individuals during specific security scenarios, according to one embodiment. This analysis may focus on identifying deviations from normal gait patterns that can suggest the concealment of a weapon, such as stiffness in one leg, asymmetric arm swings, or other indicators of hidden objects, according to one embodiment.

Unique Gait Signatures: Beyond threat detection, gait analysis may also be employed as a form of biometric identification, according to one embodiment. Each person's gait is unique, and by capturing and analyzing these gait patterns, the system may identify individuals based on their movement alone, according to one embodiment. This feature may be particularly useful for tracking known individuals of interest without relying on facial recognition or other more invasive identification methods, according to one embodiment.

Communications during a Foot Pursuit: In an innovative embodiment designed to address the challenges of foot pursuits in law enforcement and security operations, a specialized drone system 150 may be integrated to serve as a communication link between law enforcement and suspects, according to one embodiment. This UAVs 136, equipped with communication capabilities, may be deployed to engage with a suspect actively attempting to flee on foot, according to one embodiment. The system may aim to safely manage the pursuit, offering commands or negotiations aimed at de-escalating the situation without direct physical confrontation initially, according to one embodiment.

The drone (e.g., UAVs 136) may be equipped with a loudspeaker and microphone, enabling two-way communication between the officer and the suspect, according to one embodiment. This system may enable officers or commanders at headquarters to issue commands, warnings, or negotiate with the suspect 800 in an attempt to de-escalate the situation and encourage peaceful surrender, according to one embodiment. Understanding the importance of tone and language in negotiation, the drone's AI may adapt its communication style based on the suspect's responses, background information, or predefined protocols to increase the chances of compliance, according to one embodiment. The drone may be designed to be non-intimidating, using visual signals such as blinking lights to communicate its purpose as a communication tool rather than a surveillance or attack drone, according to one embodiment. This approach may aim to reduce the suspect's stress and potential for violent reaction, according to one embodiment. The drone (e.g., UAV 136) may be designed to function in various operational modes described below:

Officer to Suspect Communication: In scenarios where the pursuing officer needs to issue commands or warnings to the suspect but is physically unable to due to the intensity of the pursuit, the officer may communicate through the drone, according to one embodiment. The officer's message may be relayed via a control device, such as a headset or a wearable interface integrated into their tactical gear 104, and broadcasted through the drone's loudspeaker (e.g., megaphone 924), according to one embodiment.

Command Center to Suspect Communication: For more strategic communication, or in cases where negotiation might be necessary, the command center 302 may take over the communication process, according to one embodiment. Specialists or negotiators may use the drone as a proxy to communicate directly with the suspect, offering instructions, warnings, or attempting to de-escalate the situation remotely, according to one embodiment.

Haptic Response Mechanism: Upon detecting these precursors, the tactical gear 104 AI system may trigger a haptic response 400 tailored to the specific nature of the detected precursor, according to one embodiment.

Vibration Patterns: Different vibration patterns (e.g., as described in FIG. 10 haptic table 1050) may be assigned to various precursors, according to one embodiment. For instance, a rapid pulsing vibration may indicate someone entering the 21-foot danger zone, while a slower, steady vibration can signal preparatory actions for flight or fight, such as adjusting clothing or removing footwear, according to one embodiment.

Intensity and Location of Vibration: The intensity and location of the haptic feedback on the tactical gear 104 may indicate the urgency and direction of the threat, according to one embodiment. For example, a stronger vibration on the front side of the vest may alert the wearer to a threat directly ahead, according to one embodiment.

Sequential Alerts: If multiple precursors are detected in quick succession, the tactical gear 104 may deliver a series of haptic alerts, enabling the wearer 114 to understand the evolving situation without needing to visually confirm these cues, according to one embodiment.

By providing immediate, intuitive feedback directly to the wearer's body, the tactical gear 104 may allow law enforcement officers to react swiftly and appropriately to potential threats, even in situations where their visual attention may be compromised or directed elsewhere. This system may enhance situational awareness and decision-making capabilities, fundamentally improving the safety and operational efficiency of officers in the field, according to one embodiment. Incorporating technology to detect and interpret these approaching indicators may enhance the safety of law enforcement personnel by providing them with actionable intelligence, thus reducing the likelihood of physical confrontations and enhancing the overall effectiveness of field operations, according to one embodiment. The tactical gear 104, integrated with advanced sensors and AI capabilities, may be designed to enhance the detection and response to various indicators of drug or alcohol impairment during interactions with individuals, according to one embodiment. Detection Capabilities:

Shiftiness of the Eyes and Glossy Eyes: Cameras equipped with high-definition and infrared capabilities may detect rapid eye movements and the physical appearance of the eyes, signaling nervousness or substance influence, according to one embodiment. AI algorithms analyze these visual cues to assess potential impairment, according to one embodiment.

Speech Patterns: By employing auditory sensors and advanced natural language processing algorithms, the gear may analyze speech for signs of acceleration, slowness, slurring, or incoherence, according to one embodiment These speech patterns may be crucial indicators of possible drug or alcohol influence, according to one embodiment.

Failure to Multi-task: Responsive device 106 may observe and AI may interpret actions that demonstrate an individual's difficulty in performing simultaneous tasks, a common symptom of impairment, according to one embodiment.

Repetitive or Nonsensical Conversation: The AI system may identify patterns in speech that indicate confusion, disorientation, or an inability to follow the conversation, such as repeating questions or rambling about unrelated topics, according to one embodiment.

Physical Coordination and Movements: Motion sensors and visual analysis may detect abnormal physical behaviors such as slowed actions, imbalance (swaying), or unusual tics, according to one embodiment. These behaviors may be analyzed in the context of the individual's overall movement and interaction with the environment, according to one embodiment.

Open Bottles and Other Paraphernalia Visibility: Visual sensors may identify objects within the vehicle that suggest substance use, such as open bottles, Ziploc bags, or other containers associated with drug use, according to one embodiment.

Upon detecting one or more signs of drug or alcohol impairment, the tactical gear 104 may alert the wearer through haptic feedback mechanisms, providing a non-visual, discreet notification that allows the officer to maintain focus on the individual and the environment, according to one embodiment. The nature of the feedback (e.g., vibration patterns, intensity) may indicate the type of impairment suspected, enabling the officer to adapt their approach accordingly, according to one embodiment. The haptic feedback may provide real-time alerts to officers, enabling quicker adjustments in handling situations involving impaired individuals, potentially reducing risks, according to one embodiment. The discreet nature of haptic alerts may ensure that the officer gains insights without escalating the situation, maintaining a safer interaction dynamic, according to one embodiment. The sensors' data, including video and audio analysis, may be logged as part of the encounter's record, providing valuable evidence for legal proceedings if necessary, according to one embodiment. The AI's analysis and the recorded data from encounters may serve as training material for law enforcement, helping to refine detection techniques and interaction strategies with impaired individuals, according to one embodiment. Incorporating these technologies into tactical gear 104 may not only enhance the officers' ability to detect and respond to signs of drug or alcohol impairment but also contributes to safer, more effective law enforcement practices, according to one embodiment.

The tactical gear 104, designed with advanced detection capabilities and integrated with a comprehensive sensor array, may identify potential gun-related threats through nuanced behavioral and visual cues, according to one embodiment. This detection system may combine motion sensors, visual recognition technology, artificial intelligence (AI), and thermal imaging to interpret actions and physiological signs indicative of a concealed weapon, according to one embodiment.

Detection Mechanisms Integrated within the Personal Protective Equipment 100 May Include:

Body Posture and Movement Analysis: The tactical gear 104 system may utilize motion sensors and AI to analyze body posture and movements, according to one embodiment. Leaning of the non-dominant shoulder towards the police, a movement that may indicate shielding or preparing to draw a weapon, may be detected through these sensors (e.g., array of haptic sensors 210, array of visual sensors 200), according to one embodiment. The AI may evaluate this movement within the context of the situation to assess threat levels, according to one embodiment.

Visual Recognition Technology: Integrated cameras or visual sensors 102, potentially may be enhanced by real-time data from UAVs, use AI-driven visual recognition to detect repeated touching or glancing towards areas where weapons are commonly concealed, such as under clothing, within front hand pockets of hoodies, sweaters, or jackets, and in cross-body fanny packs, according to one embodiment.

Thermal Imaging: Concealed weapons, particularly those made of metal, may alter the thermal profile of an individual, according to one embodiment. Thermal sensors (e.g., analogous to the thermal sensor 916) may detect unusual heat signatures or the lack thereof between the belly and body or around waist areas where guns are often hidden, providing a clue to the presence of a concealed firearm, according to one embodiment.

Dominant Hand and Access Patterns: The AI system may analyze the positioning of objects (e.g., using object recognition module 122 of the personal protective equipment 100) and body adjustments that align with dominant hand accessibility, according to one embodiment. This may include observations such as individuals moving the compartment of a cross-body fanny pack for easier access or the detectable slant in clothing caused by the weight of a concealed weapon, according to one embodiment.

Haptic Feedback for Gun Situation Awareness: Upon detecting signals indicative of a concealed weapon, the tactical gear's AI system (e.g., threat detection model 108) may trigger a specific haptic response 400 pattern to alert the wearer 114 to the potential threat, according to one embodiment:

Distinct Vibration Patterns: Custom vibration alerts may inform the officer of different threat levels or types of weapon-related behaviors observed, according to one embodiment. For example, a unique pulsating vibration might be used to indicate the detection of an individual adjusting a concealed weapon's position, according to one embodiment.

Directional Alerts: The vest may utilize haptic feedback to indicate the direction of the potential threat, enabling the wearer 114 to focus their attention appropriately without visually confirming the suspect's actions, according to one embodiment.

Urgency Levels: The intensity of the vibration may convey the urgency or immediate threat level, with more intense feedback signaling higher risks, according to one embodiment.

Sequential and Contextual Alerts: If the system detects a combination of precursors, such as body movement followed by touching a concealed area, it may provide a series of haptic alerts in quick succession, emphasizing the need for caution and readiness, according to one embodiment.

By incorporating these sophisticated detection and alert systems, the tactical gear 104 may empower law enforcement officers with enhanced situational awareness, allowing them to preemptively identify potential threats and respond with appropriate caution and strategy, according to one embodiment. This technology may underscore a significant advancement in personal protective equipment, combining safety with intelligent threat detection to address the complex challenges faced by officers in the field, according to one embodiment.

The tactical gear 104, equipped with an array of advanced sensors (e.g, array of haptic sensors 210, array of visual sensors 200, etc.) and powered by sophisticated AI algorithms, may be designed to enhance the situational awareness of law enforcement officers by detecting subtle cues and behaviors indicative of concealed weapons or contraband. This gear may address specific scenarios and behaviors as follows:

Watch their Hands:

Running Biomechanics Impacted: Advanced motion sensors and AI analysis may detect anomalies in an individual's running biomechanics, such as one arm moving less than the other or a hand consistently placed near a concealed area, suggesting the presence of a concealed weapon, according to one embodiment. Haptic feedback may alert the wearer 114 of these observations, enabling them to approach the situation with heightened caution, according to one embodiment.

Traffic Stop:

Repositioning Contraband with Legs: Visual sensors 102 integrated into the tactical gear 104 or supported by UAV 136 surveillance capture and analyze the body language and movements of individuals during a traffic stop, according to one embodiment. The AI may identify specific behaviors, such as individuals looking down at their legs while repositioning objects with their feet, and provides a haptic alert to signal the attempt to conceal contraband, according to one embodiment.

Direct Gaze and Continuous Reaching: The system's AI may process visual data to recognize when a suspect 800 consistently looks at or reaches toward a specific location on their body or within the vehicle, suggesting the hiding spot of a concealed item, according to one embodiment. This repeated behavior may trigger a specific pattern of haptic feedback, alerting the officer to potential concealment spots, according to one embodiment.

Clothing Adjustments and Leg Extension: Similar to visual cues, adjustments in clothing or unusual positioning, like a backseat passenger extending their legs in an unnatural manner, may be flagged by the AI, according to one embodiment. These actions, analyzed in real-time, may activate a corresponding haptic alert, indicating the possible concealment of objects, according to one embodiment.

Observation of Suspicious Items: The tactical gear's AI (e.g., threat detection model 108) may be trained to recognize the visual signatures of contraband packaging, such as graphic bags, small rubber bags, or unusual amounts of money, either through direct observation or relayed UAV footage, according to one embodiment. Upon detection, the officer may receive a haptic alert (e.g., haptic response 400), guiding their search or questioning, according to one embodiment.

Pre-Stop Vehicle Movement: Sudden or excessive movement within a vehicle following the activation of police lights but before the vehicle stops may indicate attempts to hide contraband or weapons, according to one embodiment. The tactical gear 104, using inputs from motion sensors or UAV surveillance, may alert the officer to these last-minute adjustments, suggesting a thorough search upon stopping the vehicle, according to one embodiment.

Through these advanced detection methods and haptic feedback mechanisms, tactical gear 104 may significantly enhance an officer's ability to detect concealed weapons and contraband, promoting safety and efficacy during operations, according to one embodiment. This technology may enable officers to interpret potential threats and contraband concealment behaviors more accurately, ensuring a well-informed approach to each encounter, according to one embodiment.

The integration of advanced technology into tactical gear 104 may offer a multifaceted approach to alerting wearers about potential threats or important situational changes, according to one embodiment. Beyond haptic feedback, which provides tactile alerts through vibrations, wearers may receive notifications through audio, visual cues, and even coded language or keywords, according to one embodiment. These diverse notification methods may enhance situational awareness and allow for discreet communication that can maintain operational secrecy and safety, according to one embodiment.

Audio Alerts

Earpiece Communication: Wearers may receive spoken alerts through an earpiece connected to the tactical gear 104 system, according to one embodiment. This method may allow for immediate communication of detailed information directly into the wearer's ear, minimizing the risk of suspects or bystanders overhearing sensitive data, according to one embodiment.

Coded Sounds: Specific tones or sequences of beeps may be used to represent different alerts, such as the urgency of a situation or the type of threat detected, according to one embodiment. These sounds may be designed to be recognizable to the wearer 114 but not to untrained ears, according to one embodiment.

Visual Alerts

Heads-Up Display (HUD): Some tactical gear 104 may include HUDs in eyewear or visors, providing visual notifications directly in the wearer's line of sight, according to one embodiment. Information may be displayed as icons, text, or even augmented reality overlays that do not obstruct the wearer's view but add valuable contextual information, according to one embodiment.

LED Indicators: Small LED lights on the tactical gear 104 may flash or change color to signal different alerts, according to one embodiment. These indicators may be positioned to be easily seen by the wearer 114 without revealing the alert to others, according to one embodiment.

Coded Language or Keywords

Predefined Keywords: The AI system may use a speaker to utter predefined keywords that sound innocuous to bystanders but carry specific meanings for the wearer 114, according to one embodiment. For instance, saying "Omaha" may indicate the presence of a gun, while another name might signify different types of threats or situational updates, according to one embodiment.

Subtle Verbal Cues: The system may employ less explicit verbal cues that blend into normal conversation but are understood by the wearer 114 to convey messages or alerts. These may be phrases or references that, while seeming ordinary, may have been predetermined to carry specific meanings, according to one embodiment.

Combined Notifications

For enhanced effectiveness, these notification methods may be combined to ensure the wearer 114 receives and recognizes important alerts under various conditions, according to one embodiment. For example:

Dual Alerts: A visual alert for a specific threat might be accompanied by a tactile vibration to ensure the wearer notices the alert even if they're momentarily not looking at the HUD, according to one embodiment.

Sequential Alerts: In situations where discretion is paramount, a coded keyword may be used first, followed by detailed information transmitted through an earpiece once it's safe to do so, according to one embodiment.

Priority Alerts: High-priority threats may trigger all forms of notification simultaneously to ensure immediate attention, whereas lower-priority alerts may only activate a single notification method to avoid overwhelming the wearer, according to one embodiment.

This sophisticated approach to notifications within tactical gear 104 may not only enhance the safety and effectiveness of law enforcement personnel and military operators but also provides flexibility in how information is disseminated and received during critical operations, according to one embodiment. By leveraging a combination of haptic, audio, visual, and coded language alerts, wearers may remain acutely aware of their surroundings and any potential threats, all while maintaining operational discretion and minimizing the risk of miscommunication, according to one embodiment.

Upon the detection of such threats by the visual sensors 102, the corresponding responsive device 106 embedded within the wearer's body activates, providing tactile, auditory or visual feedback in the form of vibrations, according to one embodiment. While FIG. 1 illustrates the placement of responsive device 106 primarily in the torso area, alternative configurations may be feasible, allowing for adaptable sensor distribution across the wearer's body, according to one embodiment.

Signal Jamming System Integration

Jamming Devices: These tactical gear 104 devices may be designed to block cell phone and radio frequencies within a specific radius, effectively creating a communication denial zone around each officer or under a zone of the unmanned aerial vehicle 136 (e.g, Denial of communications (jamming cell phone or radio signals to prevent communication from a suspect or potentially to prevent remote bomb detonation).

Drone-Deployed Jamming Units: For broader area coverage or to target specific locations from a safe distance, drones equipped with signal jamming technology may be deployed, according to one embodiment. The unmanned aerial vehicle 136 may hover over an area of interest, such as a standoff location, to prevent suspects from using communication devices or detonating devices remotely, according to one embodiment.

Operational Modes and Controls

Selective Jamming: The system may be capable of selective jamming, allowing operators to block specific frequencies, such as those used for cell phones, while leaving emergency communication channels open for law enforcement use, according to one embodiment. This precision may prevent complete communication blackouts, ensuring coordination among response teams remains unaffected, according to one embodiment.

Remote Activation: Jamming devices may be activated remotely from a command center or through a control interface on the officer's tactical gear 104, according to one embodiment. This flexibility may allow for immediate response to evolving situations and the ability to activate or deactivate the jamming as needed, according to one embodiment.

Features and Benefits

Prevention of Remote Detonations: By blocking the signals that may be used to remotely detonate explosive devices, the system may significantly reduce the risk of such attacks, according to one embodiment.

The connectivity between the array of visual sensors 200, array of haptic sensors 210, and the combined memory and power module 110, as depicted in FIG. 1, may be concealed within the gear to ensure a streamlined design, according to one embodiment. Notably, the activation of haptic alerts, exemplified by haptic alert, may serve as the trigger for the gear to respond to detected threats, according to one embodiment. Moreover, the presence of the object recognition module 122 and the threat detection model 108, housed within the computational core (e.g., compute module 118), may serve as the operational brain of the device, according to one embodiment. In one embodiment, the compute module 118 may be upgradable and is available in a number of potential configurations, according to one embodiment. Different versions of the compute module 118 may employ advanced algorithms to recognize one or more potential threats, such as pre-assaultive indicators, firearms or bladed weapons, chemical dependency addiction, alcohol addiction, enhancing the wearer's situational awareness, according to one embodiment.

The combined memory and power module 110, a pivotal component of the system, may not only provide power to the device's electronics, including responsive device 106 and computational modules but also features combined non-volatile memory for data storage when the combined memory and power module 110 is docked, according to one embodiment. This may enable the seamless uploading of critical information to a central server, facilitating post-incident analysis, according to one embodiment. Additionally, the combined memory and power module 110 may capture and store the wearer's GPS coordinates (e.g., using GPS module 116) during active duty, ensuring accurate documentation of deployment locations, according to one embodiment.

In operational terms, the system may remain dormant until the wearer 114 is dispatched to an active incident location, conserving battery life, according to one embodiment. Upon activation, all computational modules and sensor arrays may be initiated, remaining operational for the duration of the assignment, according to one embodiment. The threat detection model 108, an integral part of the system, may employ artificial intelligence algorithms trained to identify ambient threats 132 in the wearer's vicinity, enhancing the device's proactive threat detection capabilities, according to one embodiment.

In summary, FIG. 1 illustrates a comprehensive depiction of the innovative personal protective device 100, integrating advanced visual sensors 102, haptic feedback mechanisms (e.g., array of haptic sensors 210), computational modules (e.g., compute module 118), and combined memory and power technology (e.g., using combined memory and power module 110) to enhance the safety and effectiveness of security personnel in challenging environments, according to one embodiment.

Figure 2:
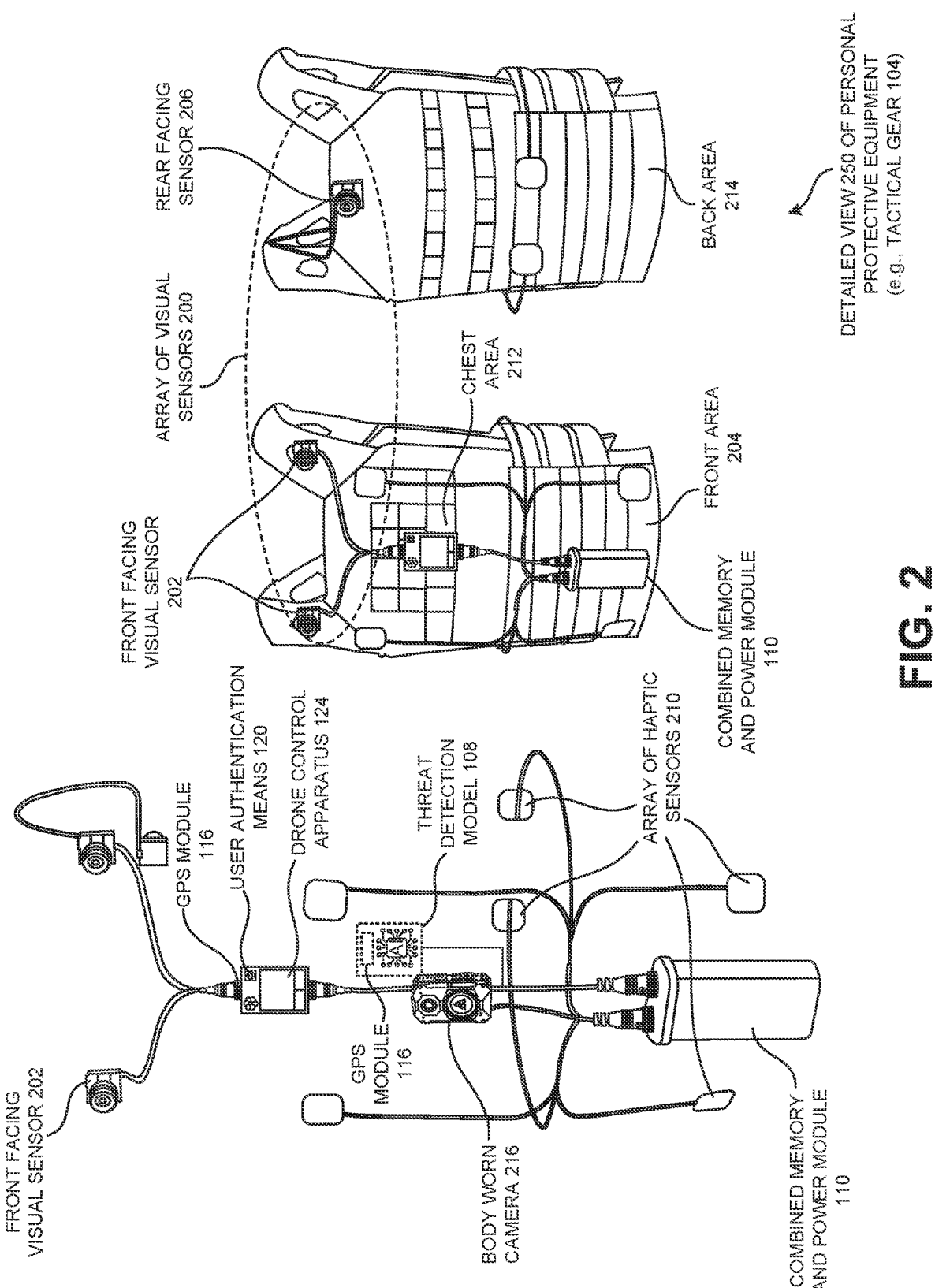
FIG. 2 is a detailed view of the tactical gear of FIG. 1 illustrating an exemplary arrangement of its internal components, according to one embodiment.

FIG. 2 is a detailed view 250 of the personal protective equipment 100 of FIG. 1 illustrating the arrangement of its internal components, according to one embodiment. Particularly, FIG. 2 builds on FIG. 1, and further adds, an array of visual sensors 200, a front-facing visual sensor 202, a front area 204, a rear facing sensor 206, an array of haptic sensors 210, a chest area 212, a back area 214, and a body worn camera 216, according to one embodiment.

The array of visual sensors 200 may be an assembly of a number of small, high-resolution cameras and/or sensors (e.g., thermal sensors, low light sensors, infrared sensors, motion sensors, proximity sensors, fire and smoke sensors, etc.) distributed strategically across the tactical gear 104. These sensors may be embedded within the fabric and/or attached to the gear's surface in a manner that optimizes the field of view and coverage area. Each sensor may be capable of capturing visual data in various spectrums, including visible light, infrared, and possibly thermal imaging to provide situational awareness in different environmental conditions. These sensors may be designed to cover a 360-degree field of view around the wearer 114, providing a comprehensive visual feed of the surrounding environment, according to one embodiment.

The responsive device 106 may be interconnected, likely through a secure, low-latency network that allows for real-time data processing and analysis. The AI component of the threat detection model 108 may be crucial for interpreting the vast amounts of visual data collected by the array of visual sensors 200. The threat detection model 108 may utilize machine learning algorithms to identify and categorize objects, detect motion, recognize faces and/or behavioral patterns to assess potential threats automatically, according to one embodiment.

The AI system of the threat detection model 108 may process the visual data in real-time, using advanced algorithms for object recognition using the object recognition module 122, threat assessment, and situational awareness. It may highlight points of interest, identify known individuals and/or objects, and flag potential hazards. The threat detection model 108 may be trained to recognize specific patterns, uniforms, weapons, and even behavioral cues that may indicate a threat to the wearer 114, according to one embodiment.

The threat detection model 108 might also be designed to adapt and learn from new situations, improving its accuracy and response over time. It may provide the wearer 114 with actionable insights through a heads-up display (HUD) and/or other augmented reality (AR) interfaces, haptic feedback (e.g., haptic alert 400 using the responsive device 106 and threat detection model 108), and/or audio alerts. Moreover, the threat detection model 108 of the compute module 118 may be programmed to work collaboratively with other systems within the tactical gear 104, such as communication arrays, navigation tools (e.g., using the GPS module 116), and health monitoring devices, to provide a comprehensive, integrated operational platform for the wearer 114, according to one embodiment.

This advanced integration of visual sensors and AI may not only enhance the situational awareness and response capabilities of the wearer 114 but may also contribute to team-level strategies and tactics by sharing processed information across a networked battlefield or operational environment.

FIG. 2 is a detailed view of the tactical gear 104 of FIG. 1 illustrating an exemplary arrangement of its internal components, according to one embodiment.

The front-facing visual sensor 202 may be an electronic device that detects and responds to a stimulus from the physical environment in its surrounding. The front-facing visual sensor 202 may be a sophisticated component integrated within the front area 204 of the tactical gear 104 designed for real-time data acquisition and processing to assist the wearer 114 in identifying and reacting to threats and other important environmental cues, according to one embodiment.

The front-facing visual sensor 202 may include an advanced camera capable of capturing high-definition video in a range of lighting conditions, from bright daylight to low-light scenarios. It may also possess infrared capabilities for night vision, allowing the wearer 114 to see in the dark. In addition, the front-facing visual sensor 202 may include thermal imaging to detect heat signatures, which may be especially useful for identifying living targets at night and/or through obstructions like smoke or foliage, according to one embodiment.

The AI component of the front-facing visual sensor 202 may be responsible for analyzing the visual feed. It may use machine learning algorithms to perform tasks such as facial recognition, uniform and insignia identification, object detection, and even behavioral analysis to assess potential threats. For example, the AI of the front-facing visual sensor 202 may be trained to recognize the subtle movements that precede an aggressive action, allowing for preemptive response, according to one embodiment.

In an embodiment focused on enhancing security operations through advanced technology, tactical gear 104 equipped with facial recognition capabilities may represent a significant leap forward, according to one embodiment. This gear, designed for use by secret service agents, police officers, and military personnel, may incorporate computer vision technology to identify individuals within large crowds or during specific scenarios like traffic stops, according to one embodiment. Captured images may be processed in real-time through embedded computer vision algorithms, according to one embodiment. These algorithms may compare facial features against databases, such as the National Crime Information Center (NCIC), local lookouts, or protective intelligence (Intel) subjects databases, to identify known threats or individuals of interest, according to one embodiment.

Earpiece communication may also relay detailed information about the identified individual, such as their threat level, last known actions, or reasons for interest. For example, the generated facial signature may be automatically queried against the government database, which includes records of wanted persons, missing persons, gang members, terrorists, sex offenders, and other persons of interest, according to one embodiment. The query process may be facilitated through secure, encrypted communication channels to protect data privacy and integrity, according to one embodiment. If a match is found within the NCIC database, the tactical gear 104 may alert the wearer 114. This may be achieved through several methods:

Haptic Feedback: The gear may vibrate in a specific pattern to indicate a match, ensuring the wearer 114 is alerted discreetly, according to one embodiment.

Audio Cues: An earpiece connected to the tactical gear 104 may provide a verbal alert or details about the matched individual, according to one embodiment.

Visual Notification: For tactical gear 104 equipped with a heads-up display (HUD), information about the matched individual, such as their identity and reason for interest, may be displayed, according to one embodiment.

Upon receiving an alert, the officer may take appropriate tactical actions based on the specific context and protocols, according to one embodiment. This may include detaining the individual for further questioning, calling for backup, or taking precautionary measures if the person is known to be dangerous, according to one embodiment. This information may be delivered securely and discreetly to the wearer. For gear equipped with heads-up displays (HUDs), a visual alert may appear, showing the suspect's photograph, name, and relevant details, according to one embodiment. This may allow the wearer 114 to visually confirm the match and take appropriate action.

At events with large crowds, such as political rallies, the system may scan attendees, identifying potential threats from a database of individuals who have made threats against protected figures or are known to pose security risks, according to one embodiment. During traffic stops, officers may quickly identify individuals in a vehicle who may give false information or are wanted, without the need for manual checks or questioning, according to one embodiment. Facial recognition (e.g., using facial recognition algorithm 1704 of the government database 1714) may enhance security by identifying individuals (e.g., face 1710 of the suspect 800) who pose a threat, such as those with restraining orders or flagged for surveillance, ensuring timely intervention before incidents occur, according to one embodiment. The deployment of facial recognition in tactical gear 104 may consider legal frameworks and privacy concerns, according to one embodiment. Operational protocols may ensure the technology's use complies with regional laws and civil liberties, according to one embodiment. Information captured and processed through facial recognition may be secured against unauthorized access, ensuring that personal data is protected in line with privacy standards, according to one embodiment.

Upon a positive match with a person of interest (e.g., target person 1720 of the government database 1714) or a potential threat, the tactical gear 104 may trigger a discreet haptic feedback to alert the wearer 114, according to one embodiment. This may be a specific vibration pattern that indicates the nature of the alert, allowing the wearer 114 to respond without alarming the suspect 800 or the public, according to one embodiment. By utilizing facial recognition technology, tactical gear 104 enables law enforcement and security personnel to enhance situational awareness, preemptively identify threats, and respond more effectively to potential security risks, according to one embodiment. This integration of technology into tactical operations may signify a move towards smarter, more secure approaches to public safety and national security, according to one embodiment.

In secret service scenarios, the integration of facial recognition technology (e.g., using facial recognition algorithm 1704 of the government database 1714) with tactical gear 104 for identifying both local and national lookouts during events or operations may involve a sophisticated network of databases (e.g. using government database 1714), communication systems, and real-time analysis (e.g., using realtime data 1112, analytics summary 1100, AI summary 1106 of the system), according to one embodiment. This technology may significantly enhance security measures, especially during high-profile events with large crowds in the crowded field 300 or in sensitive locations, according to one embodiment. Agents and officers equipped with tactical gear 104 featuring embedded cameras and facial recognition technology may be deployed at event venues or within the vicinity of protected sites, according to one embodiment. The tactical gear 104 may be configured to continuously capture and analyze the faces (e.g., face 1710 of attacker 602) of individuals within the crowd (e.g., in the crowded field 300), at entry points, or during any encounters, according to one embodiment.

As the event progresses, the tactical gear 104 may scan and analyze faces (e.g., using identity artificial intelligence model 1722 and facial recognition algorithm 1704) in real-time, comparing them against the integrated database (e.g. using government database 1714) of local and national lookouts, according to one embodiment. Utilizing advanced algorithms, the system may quickly identify matches despite potential challenges such as partial face visibility, varied lighting conditions, or the presence of facial coverings, according to one embodiment. Upon identifying a match with a lookout for target person 1720, the system may instantly alert the wearer 114 through one or multiple methods (haptic feedback, audio cues, or visual notifications on a HUD), specifying whether the match is a local or national lookout, according to one embodiment. Agents may then coordinate with command centers 302 and other field agents (e.g., wearer 114A, different wearer 114B, etc.) to manage the situation discreetly and efficiently, according to one embodiment. This may involve additional verification, discreet surveillance, interception, or detaining the individual for questioning, depending on the threat level and operational protocols, according to one embodiment.

In an alternative embodiment, where a law enforcement officer, secret service agent, or military personnel needs to quickly identify a target person 1720 (or even an animal) in a crowded or complex environment, the system may leverage a combination of user-friendly interfaces, mobile technology, and integrated tactical gear 104 to achieve this objective, according to one embodiment.

License Plate scanning: In a scenario designed to enhance the effectiveness of law enforcement patrols, tactical gear 104 equipped with visual sensors 102 may play a pivotal role in the identification and recovery of stolen vehicles, according to one embodiment. This advanced system may aim to streamline the process, making it both automated and discreet, thereby increasing the safety and efficiency of officers on duty, according to one embodiment. While on patrol, an officer may wear tactical gear 104 equipped with visual sensors 102, including body worn cameras 216 capable of high-resolution imaging and optical character recognition (OCR) technology, according to one embodiment. These sensors may be activated and continuously scan the environment for license plates (e.g., front license plate 908, back license plate 910) as the officer moves through different areas, whether on foot or in a patrol vehicle 700, according to one embodiment. The visual sensors 102 may automatically capture images of license plates on nearby vehicles, according to an embodiment. The OCR technology may then process these images in real-time, extracting the license plate numbers for further analysis, according to one embodiment.

Each recognized license plate number may be instantly queried against a database of stolen vehicles, which is regularly updated to ensure accuracy and comprehensiveness, according to one embodiment. This process may be facilitated through a secure wireless connection, maintaining data integrity and confidentiality, according to one embodiment. When the system identifies a match, indicating that a license plate is associated with a stolen vehicle (e.g., suspect vehicle 708), it may trigger an alert mechanism within the tactical gear 104, according to one embodiment.

Upon detection of a stolen vehicle, the officer's tactical gear 104 may vibrate to alert them of the find (e.g., a hidden body 922 in the suspect vehicle 708 of FIG. 9), according to one embodiment. The vibration pattern may be distinct and predefined, enabling the officer to immediately understand the nature of the alert without needing to visually confirm it on a device, according to one embodiment. This method ensures discretion, keeping the officer's attention on their surroundings and the suspect vehicle 708 without alerting the occupants (e.g., number of persons 912), according to one embodiment. Guided by the haptic feedback (e.g., haptic alert 2210), the wearer 114 may then discreetly approach the identified stolen vehicle to verify its status visually, call for backup, and prepare to engage with the occupants if necessary, according to one embodiment. This approach may minimize the risk of confrontation and enables a coordinated response, according to one embodiment. The wearer 114 may communicate the discovery to the command center 302 and/or nearby units, ensuring that additional resources are available for support during the vehicle's recovery and the occupants' apprehension, according to one embodiment.

The automated and discreet alert system may minimize the risk to officers (e.g., wearers 114) by reducing the need for direct interaction with potentially dangerous suspects until backup arrives, according to one embodiment. Continuous, real-time scanning for stolen vehicles may enhance patrol effectiveness, enabling officers to cover more ground and identify more stolen vehicles without additional resources, according to one embodiment. The use of haptic feedback may allow officers to receive haptic alerts 2210 without drawing attention, maintaining the element of surprise and operational security, according to one embodiment. By integrating visual sensors 102 and haptic feedback into tactical gear 104, law enforcement agencies may significantly improve their capacity to recover stolen vehicles and apprehend suspects, all while ensuring the safety and operational efficiency of their officers, according to one embodiment.

The AI component of the front-facing visual sensor 202 may also have a decision-making capability to prioritize and alert the wearer 114 to the most immediate threats through auditory, visual, or haptic feedback. This may be conveyed through an earpiece, a visual display inside a helmet, or vibrations in specific areas of the threat detection model 108 to indicate the direction of a threat. Integration with other systems may include network connectivity to share real-time data with team members or command centers 302, GPS module 116 for location tracking, and databases (e.g., government database 1714, visual inference database 1718, etc.) for cross-referencing individuals and/or objects detected by the responsive device 106, according to one embodiment. Durability and discretion may be the key design aspects of the array of visual sensors 200, ensuring that it is robust enough to withstand the rigors of field operations while being inconspicuous enough not to draw attention or hinder the wearer's mobility. Its placement on the tactical gear 104 may be strategic to maximize field of view while minimizing blind spots, ensuring comprehensive coverage of the area in front of the wearer 114, according to one embodiment.

The front area 204 may be an anterior portion of the tactical gear 104 on which the front-facing visual sensor 202 are installed such that it is capable of capturing visual data covering a 360-degree field of view around the wearer 114, providing a comprehensive visual feed of the surrounding environment, according to one embodiment.

Analogous to the front-facing visual sensor 202, the rear-facing sensor 206 may be an electronic device that detects and responds to a stimulus from the physical environment in its surroundings in the rear of the wearer 114 of the tactical gear 104. The rear-facing sensor 206 may be integrated within the back area 214 of the tactical gear 104 designed for real-time data acquisition and processing to assist the wearer 114 in identifying and reacting to threats and other important environmental cues, according to one embodiment. The array of haptic sensors 210 may constitute a network of tactile feedback devices designed to communicate information through the sense of touch.

Placement and Integration: The array of haptic sensors 210 may be distributed across the tactical gear 104 in key locations, such as over the shoulders, back, and sides primarily in the torso area of the wearer 114. The sensors may be embedded into the fabric of the tactical gear 104 and/or attached to the inner lining to maintain comfort and mobility, according to one embodiment.

Functionality: Each sensor in the array of haptic sensors 210 may be capable of producing different types of tactile feedback, such as vibrations, pressure, and/or temperature changes. This feedback may inform the wearer 114 of various conditions and alerts without relying on visual or auditory cues, which is critical in stealth and/or high-noise environments, according to one embodiment.

AI Processing: The array of haptic sensors 210 may be connected to the threat detection model 108 of the compute module 118 incorporated directly into the gear. This unit may receive input from various data sources, such as visual or auditory sensors, GPS, and/or other monitoring devices. The threat detection model 108 may analyze this data to detect threats, navigate terrain, and/or relay tactical information, according to one embodiment.

Communication Through Tactile Signals: Based on the threat detection model's 108 analysis, the compute module 118 may send signals to the array of haptic sensors 210 to deliver specific patterns of tactile feedback. For example, a pulsing vibration on the left side may indicate an approaching threat from that direction, while a steady pressure on the back might signal the wearer 114 to halt. The threat detection model 108 may use different rhythms, intensities, or durations of feedback to convey different messages or levels of urgency, according to one embodiment.

Adaptive Learning: The threat detection model 108 of the compute module 118 may be capable of learning from the wearer's responses and the environment to optimize the haptic feedback. For instance, if the wearer 114 consistently reacts more quickly to certain types of vibrations, the AI may prioritize those for urgent alerts, according to one embodiment.

Interactivity: The tactical gear 104 may also allow the wearer 114 to communicate back to the AI through touch, perhaps by tapping certain areas of the gear to confirm receipt of a message or to request specific information, according to one embodiment.

Power Efficiency and Durability: Given the potential for extended field use, the array of haptic sensors 210 and AI system may be designed for low power consumption and high durability. They may be powered by advanced, long-lasting combined memory and power module 110 batteries integrated within the tactical gear 104, according to one embodiment.

User Customization: The system may allow for user customization and authentication using the user authentication means 120, enabling each wearer 114 to adjust the intensity, location, and type of haptic feedback according to personal preference and mission requirements. Overall, this AI-driven array of haptic sensors 210 may enhance the situational awareness and survivability of the wearer 114 by providing an intuitive, non-disruptive means of receiving critical information, according to one embodiment.

The body worn camera 216 (e.g., Axon® Body 4 body worn camera) may be an electronic device for recording visual images in the form of photographs, film, and/or video signals for both real-time analysis and after-action review. The body worn camera 216 may be integrated within the chest area 212 area of the tactical gear 104. The body worn camera 216 may have a wide-angle lens to capture a broad field of view. In a preferred embodiment, the body worn camera 216 may work along with the personal protective equipment 100. While the personal protective equipment 100 focuses on real time threat detection in one embodiment, the body worn camera 216 may focus on storage for later review.

In an alternative embodiment, the visual sensor 102 may be part of an array of the body worn camera 216, and also store and capture visual data. In another embodiment, the body worn camera 216 may be a detachable version of the visual sensor 102, capable of doing each function described herein. Given the various environments that tactical operations may encounter, the personal protective equipment 100 may be equipped with low-light capabilities for low-light adaptability. The personal protective equipment 100 may utilize night vision and/or thermal imaging technologies to maintain visibility in near-darkness and/or through obscurants like smoke. To ensure that the sensor feed is clear even when the wearer 114 is in motion, the personal protective equipment 100 may have advanced image stabilization technology for each of its visual sensors 102, according to one embodiment.

The AI system within the personal protective equipment 100 (e.g., note: in alternative embodiments, the AI system and processing may occur in an edge processing node such as the land vehicle, patrol vehicle 700, armored carrier 134 and/or in a cloud based server) may be capable of running complex algorithms for facial recognition, license plate reading, and/or detecting specific patterns of behavior that may indicate a threat. It may also tag and categorize different elements within the video for easy retrieval. The personal protective equipment 100 may be able to stream footage to a command center 302 and/or other team members (e.g., wearer 114B-N), allowing for coordinated responses and situational awareness sharing. This streaming may be done over encrypted channels to ensure operational security, according to one embodiment.

Footage data may be stored in a secure, encrypted format, with the ability to upload data (e.g., analytics summary 1100) to a cloud server and/or local storage depending on the operational needs and security protocols. The personal protective equipment 100 may be ruggedized to withstand impacts, water, dust, and other environmental factors typically encountered in field operations, according to one embodiment. While the visual sensors 102 of the personal protective equipment 100 may autonomously record based on certain triggers or AI detections, the wearer 114 may also have the ability to manually activate or deactivate recording as necessary. The personal protective equipment 100 may be integrated with the array of sensors 200 and systems on the tactical gear 104, such as GPS module 116 for geotagging footage, biometric sensors 160 for monitoring the wearer's vitals, and array of haptic sensors 210 for alerting the wearer 114 to specific AI detections, according to one embodiment.

Since the personal protective equipment 100 may be worn and used potentially over long periods, it may be designed to be power-efficient, with a battery life suitable for extended missions and the ability to be recharged using the combined memory and power module 110 of the tactical gear 104 or have its recharged in the docking station. This personal protective equipment 100 may serve as a proactive tool to enhance the operational capabilities and safety of the wearer 114 through its AI-driven insights and connectivity, according to one embodiment.

Figure 3:
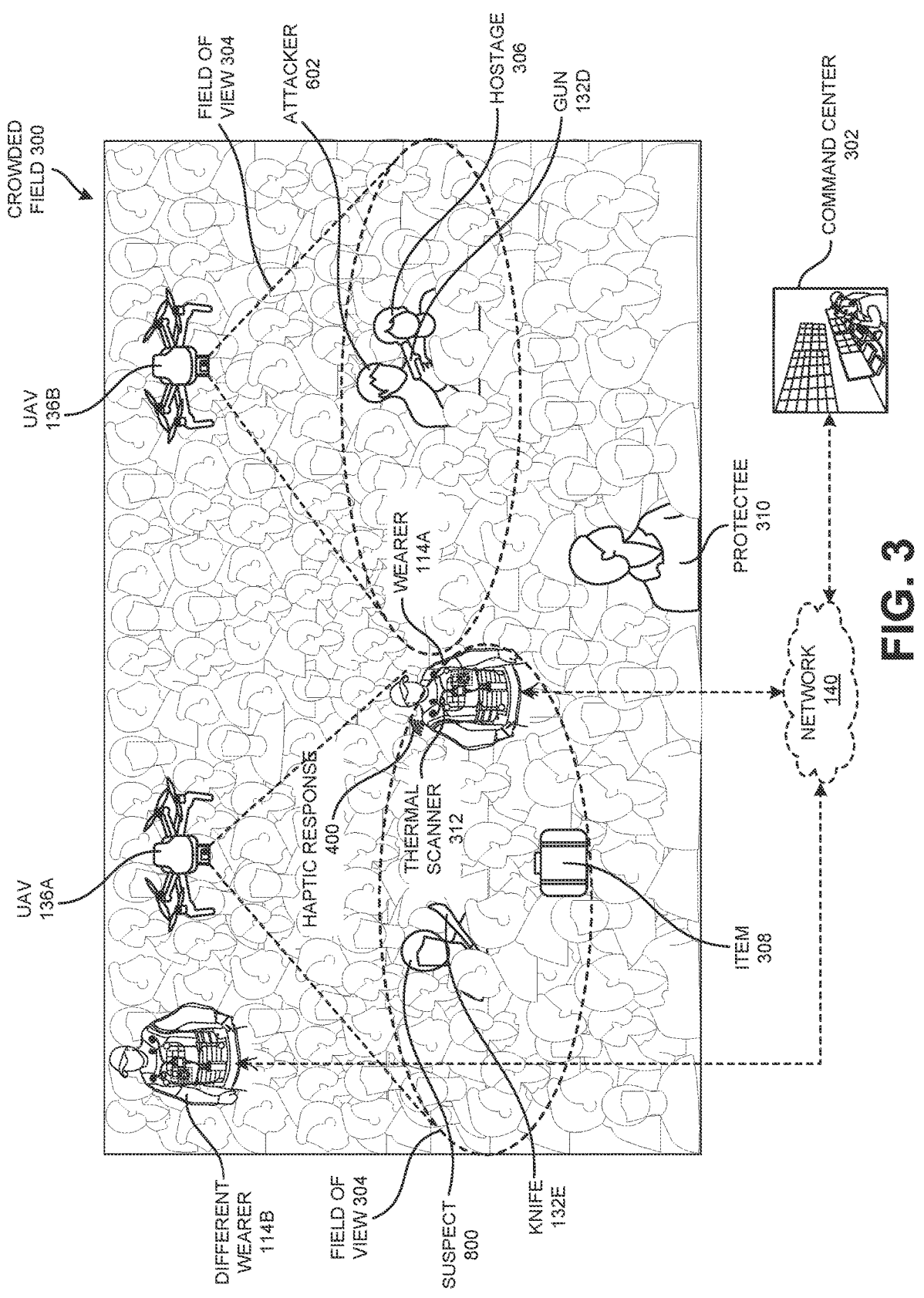
FIG. 3 is an operational view in which a UAV follows a wearer in a crowded field of people during a riot, and provides a visual view and/or a haptic response to the wearer and a command center based on a detected ambient threat to a protectee of the wearer and the additional person, according to one embodiment.

FIG. 3 is an operational view in which a UAV 136A follows a wearer 114A in a crowded field 300 of people during a riot, and provides a visual view and/or a haptic response 400 to the wearer 114A and a command center 302 based on a detected ambient threat 132 to a protectee 310 of the wearer 114 and the additional person, according to one embodiment. The UAV 136A, described in FIG. 3 may play a critical role in enhancing situational awareness and safety for individuals (referred to as the wearer 114A) in complex, dynamic environments such as riots, according to one embodiment. The UAV 136A may be designed to autonomously follow a designated individual—the wearer 114A—through a crowded field 300 filled with people, according to one embodiment. This capability is particularly invaluable in scenarios marked by chaos and potential danger, such as riots, where maintaining situational awareness is both challenging and crucial for the safety of the individual and those around them, according to one embodiment.

In this operational view, the UAV 136A not only serves as an aerial surveillance unit providing a comprehensive visual overview of the wearer's immediate environment but also acts as an intermediary for haptic communication, according to one embodiment. It may detect ambient threats 132 within the crowd—potentially armed individuals, aggressive behavior, weapons (such as the machete knife 132E and the gun 132D in FIG. 3) or other hazards—and conveys this critical information back to the wearer 114A and a command center 302 in real-time, according to one embodiment. The communication of detected threats is achieved through three primary means: a visual view, likely a live feed of the surveillance captured by the UAV, notifications based on generative artificial intelligence (printed on a screen, texted out, emailed out, etc.) and a haptic response 400, according to one embodiment.

An item 308 (e.g., backpack, a pressure cooker, and/or explosive device) left by suspect 800 may be identified among the crowded field 300 in FIG. 3 through the visual sensor 102 and/or the UAV 136A-N according to one embodiment. This may reflect a further embodiment tailored to enhance security measures within sensitive environments such as schools, public spaces, or transport hubs, the tactical gear system may incorporate advanced technology for detecting when individuals intentionally leave behind items 308, such as backpacks, packages, or other objects that can pose a potential threat, according to one embodiment. This technology goes beyond simple object detection, focusing on the behavior of individuals (e.g., suspect 800) placing items down and then departing without them, which can indicate a security threat. Integrated body worn cameras 216 on tactical gear 104, UAV 136A-N, or stationary surveillance systems may use computer vision to continuously monitor areas of interest, according to one embodiment. These cameras are not only programmed to detect stationary objects but may also be equipped with algorithms capable of recognizing specific behavioral patterns associated with an individual intentionally leaving an object behind, according to one embodiment.

Upon detecting suspicious behavior associated with leaving an item 308 behind, the system may immediately alert security personnel (e.g., wearer 114) through their tactical gear 104, according to one embodiment. The alert may be conveyed via haptic feedback to ensure discretion and an immediate response, supplemented by audio or visual cues providing detailed information about the location and nature of the potential threat, according to one embodiment.

The responsive device 106 may notify the wearer 114 of the tactical gear 104 and an additional person when the visual sensor 102 identifies a threat to a protectee 310 of the wearer 114 and the additional person. The additional persons and/or the wearer 114 may all be responsible for the same protectee 310. The method may include identifying a target person 1720 using an identity artificial intelligence model 1722, vibrating a responsive device 106 on a tactical gear

104 of the wearer 114 when a visual sensor 102 of the tactical gear 104 detects the ambient threat 132 to the protectee 310 of the wearer 114, and modulating an intensity of vibration of the responsive device 106 based on a proximity of the ambient threat 132 to the wearer 114 and the protectee 310. A pattern of vibration of the responsive device 106 may be dependent on a type of threat. A thermal scanner 312 may be coupled to the tactical gear 104 to capture and create images or videos based on the infrared radiation (heat) emitted by objects (e.g., ambient threat 132 and/or the item 308 left behind by the suspect 800) in its field of view. The thermal scanner 312 may measure the temperature over a wide area and may differentiate temperatures across different parts of the scene. The thermal scanner 312 may alert the wearer 114 when a heat signature detects the presence of the threat to the wearer 114 and/or the protectee 310 of the wearer 114, according to one embodiment.

The haptic response 400 may particularly be an innovative aspect of this system, according to one embodiment. Upon detection of a threat, the UAV 136 may trigger a haptic feedback mechanism integrated within the wearer's personal protective equipment 100, according to one embodiment. This may manifest as a vibration or other tactile, auditory, or visual signal directly to the wearer 114A, alerting them to the danger without requiring them to shift their focus or divert their attention from their immediate surroundings, according to one embodiment. The haptic feedback may offer a discreet, immediate, and intuitive means of communication, enhancing the wearer's ability to react swiftly to potential threats, according to one embodiment. Additionally, this information may be simultaneously relayed to a command center 302 and the different wearer 114B, ensuring that situational awareness is shared among all relevant parties, facilitating coordinated response efforts, and enhancing overall operational effectiveness in managing the situation, according to one embodiment.

This embodiment may underscore a significant advancement in personal protective technology, leveraging the synergistic potential of UAV surveillance (e.g., using UAV 136), artificial intelligence (AI)-driven threat detection (e.g., using threat detection model 108), and haptic communication (e.g., using array of haptic sensors 210), according to one embodiment. It might epitomize a forward-thinking approach to enhancing the safety and situational awareness of individuals operating in potentially hazardous environments, offering a blend of autonomy, immediacy, and discretion in threat detection and communication, according to one embodiment.

Figure 4:
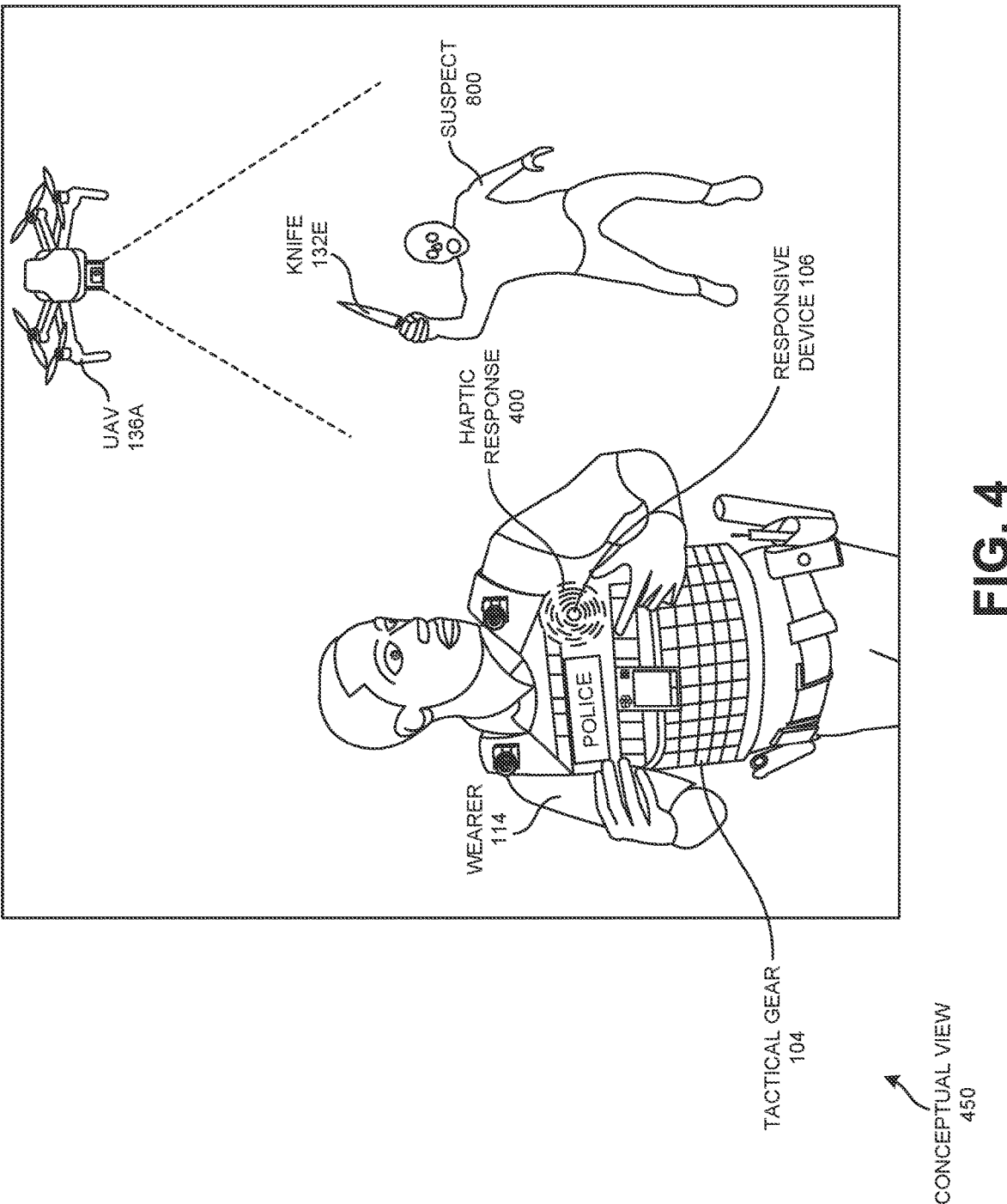
FIG. 4 is a response view of the tactical gear of FIG. 1 illustrating a haptic response when an ambient threat is detected by the UAV of the drone system of FIG. 1, according to one embodiment.

FIG. 4 is a response view of the tactical gear 104 of FIG. 1 illustrating a haptic response 400 when an ambient threat 132 is detected by the UAV 136A of the drone system 150 of FIG. 1, according to one embodiment. FIG. 4 is a conceptual view 450 of the personal protective equipment 100 of FIG. 1 illustrating the tactical gear 104 worn by a law enforcement personnel (e.g., wearer 114) during a hostile situation, according to one embodiment. As described in various embodiments of FIG. 1-28, the tactical gear 104 worn by law enforcement personnel shown in FIG. 4 may be integrated with advanced visual sensors (e.g., array of visual sensors 200), haptic feedback mechanisms (e.g., using array of haptic sensors 210), computational modules (e.g., threat detection model 108, compute module 118, etc.), and combined memory and power technology (e.g., combined memory and power module 110) to enhance the safety and effectiveness of security personnel in challenging environments, according to one embodiment.

As shown in FIG. 4, the tactical gear 104 may be equipped with a responsive device 106, which includes capabilities to sense various forms of threats, such as sharp objects, firearms, and/or other potential weapons. In the embodiment of FIG. 4, the haptic response 400 may be initiated not when the visual sensors on the tactical gear 104 detect a threat, but when a UAV 136A detects an ambient threat 132 to the wearer 114 through a camera 142 on the UAV 136A, according to one embodiment.

In another embodiment, the object recognition module 122 may analyze data from these sensors and responsive device 106 to determine the presence of the ambient threat 132 such as a gun, knife, shank, bomb and/or weapon, etc. The object recognition module 122 may analyze data from these sensors to determine the presence of the ambient threat 132 such as a gun, knife, bomb and/or weapon. Upon detecting a potential ambient threat 132, the system may use AI to quickly assess the level of danger and the appropriate response. The system may then send a haptic alert 400 to the wearer 114. This alert may be a vibration and/or other tactile signals that inform the wearer 114 of the direction and proximity of the threat without requiring them to look at a display and/or listen to audio cues, which may be critical when visual or auditory senses are already overloaded due to loud, chaotic, and/or low-visibility environment. By providing immediate physical feedback, the tactical gear 104 may enhance the wearer's situational awareness, enabling them to react quickly to the threat. The threat detection model 108 may assist in decision-making by recommending actions based on the type of detected threat and previous training data. For instance, the GPS module 116 integrated within the tactical gear 104 may direct the wearer 114 to a safe route in the proximity of the anticipated hostile attack. The threat detection model 108 may further suggest taking cover to a nearby refuge, drawing a weapon, and/or using non-lethal force, depending on the situation. Furthermore, the system might record data about encountered threats, which may be used for later analysis, training, or legal purposes. In addition, the tactical gear 104 may also be linked to a communication system (e.g., through network 140) to ensure constant connectivity with command centers 302, database, and other team members (e.g., patrol vehicle 700, different wearer 114B, 114N) for real-time intelligence and coordination, according to one embodiment.

Figure 5:
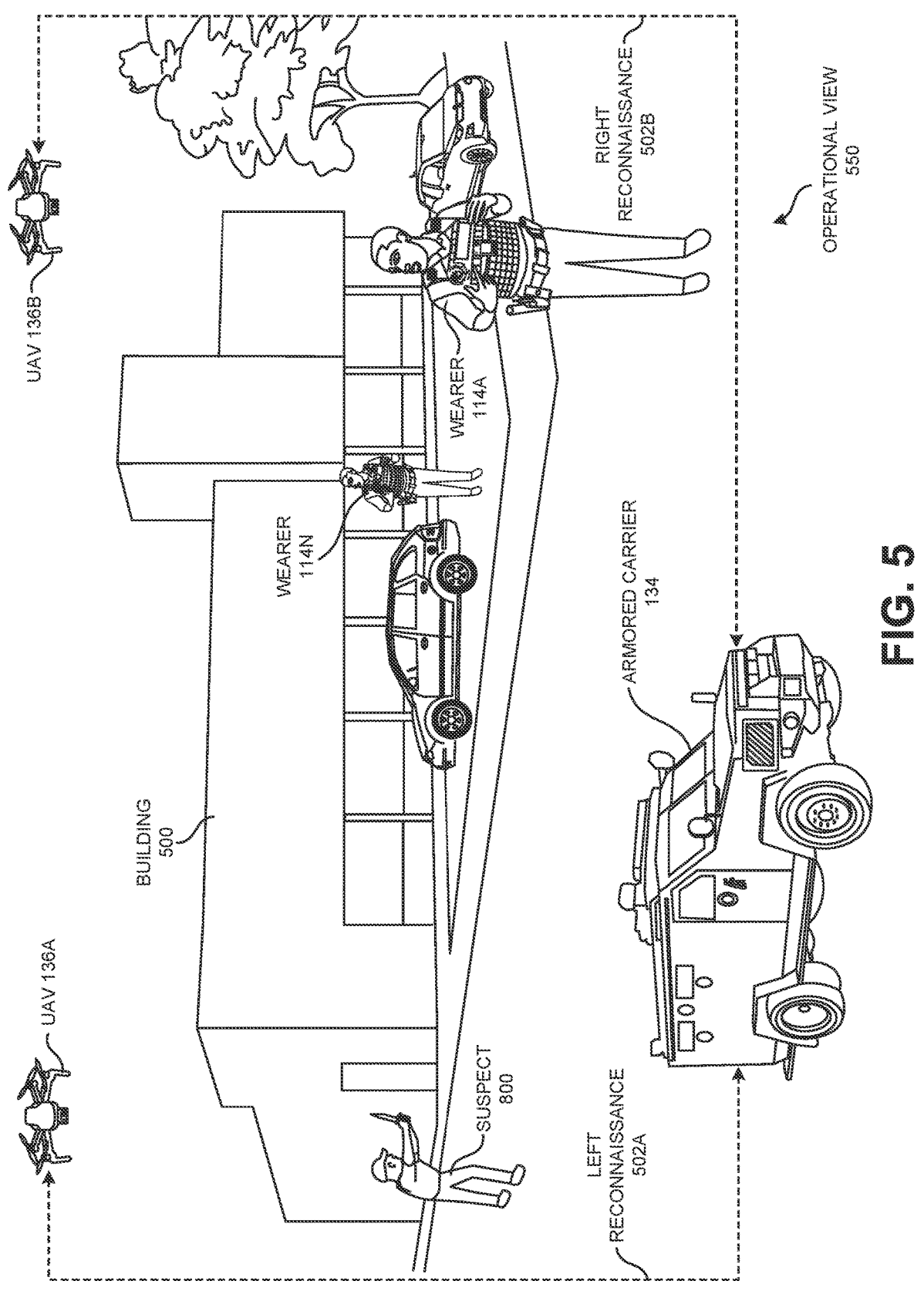
FIG. 5 is an operational view in which a first UAV to perform a left reconnaissance of a building, and a second UAV to perform a right reconnaissance of the building, after both the first UAV and the second UAV are launched from a vehicle (e.g., armored carrier, patrol vehicle) to perform advance work, according to one embodiment.

FIG. 5 is an operational view 550 in which a first UAV 136A performs a left reconnaissance 502A of a building 500, and a second UAV 136B performs a right reconnaissance 502B of the building 500, after both the first UAV 136A and the second UAV 136B are launched from a vehicle (e.g., armored carrier 134, patrol vehicle 700) to perform advance work, according to one embodiment. In FIG. 5, a scenario is presented involving a coordinated reconnaissance mission executed by two Unmanned Aerial Vehicles (UAVs), 136A and 136B, around a specific building 500, according to one embodiment. This scenario exemplifies a sophisticated operational tactic aimed at maximizing situational awareness and security efficiency in potentially hazardous environments or critical situations such as surveillance, search and rescue, or tactical operations, according to one embodiment.

Upon deployment from a vehicle, such as an armored carrier 134 or a patrol vehicle 700, each UAV 136A-N is tasked with a distinct surveillance trajectory around the building 500 (e.g., a retail store such as a Target or Walmart) to comprehensively assess the situation from multiple angles, according to one embodiment. UAV 136A is assigned to perform a left reconnaissance 502A, which entails flying a predefined path on the left side of the building 500, according to one embodiment. This path is likely determined to cover strategic points of interest, potential entry/exit points, and areas where threats or subjects of interest can be located or hidden, according to one embodiment. Similarly, UAV 136B conducts a right reconnaissance 502B, mirroring the objectives of UAV 136A on the opposite side of the building 500, according to one embodiment. This dual-path approach ensures that the surveillance covers a full 360-degree view around the building 500, leaving minimal blind spots and significantly enhancing the ability to detect potential threats, activities, or valuable intelligence, according to one embodiment.

The operation of UAVs 136A and 136B is indicative of an integrated drone system 150 strategy, where multiple drones may be utilized in concert to achieve a comprehensive surveillance objective, according to one embodiment. This strategy not only increases the operational coverage area but also reduces the time required to gather critical information, thereby enhancing decision-making speed and accuracy, according to one embodiment. The drones may relay live video feeds, capture high-resolution images, and possibly employ other sensory technologies (such as thermal or infrared cameras 142) to detect signs of human presence, heat signatures, or other indicators of interest that might not be visible to the naked eye, according to one embodiment.

Moreover, the coordinated reconnaissance around the building 500 demonstrates the versatility and tactical advantage offered by UAVs in modern operational scenarios, according to one embodiment. Such an approach is invaluable in scenarios where human entry might be risky or impossible, such as hazardous environments, areas with potential hostile threats, or when the element of surprise is crucial, according to one embodiment. Additionally, the data collected by UAVs 136A and 136B may be streamed in real-time to a command center 302 or to tactical teams on the ground, providing them with actionable intelligence to plan their next steps, whether it's conducting a raid, initiating a rescue operation, or monitoring the area for further developments, according to one embodiment.

Figure 6:
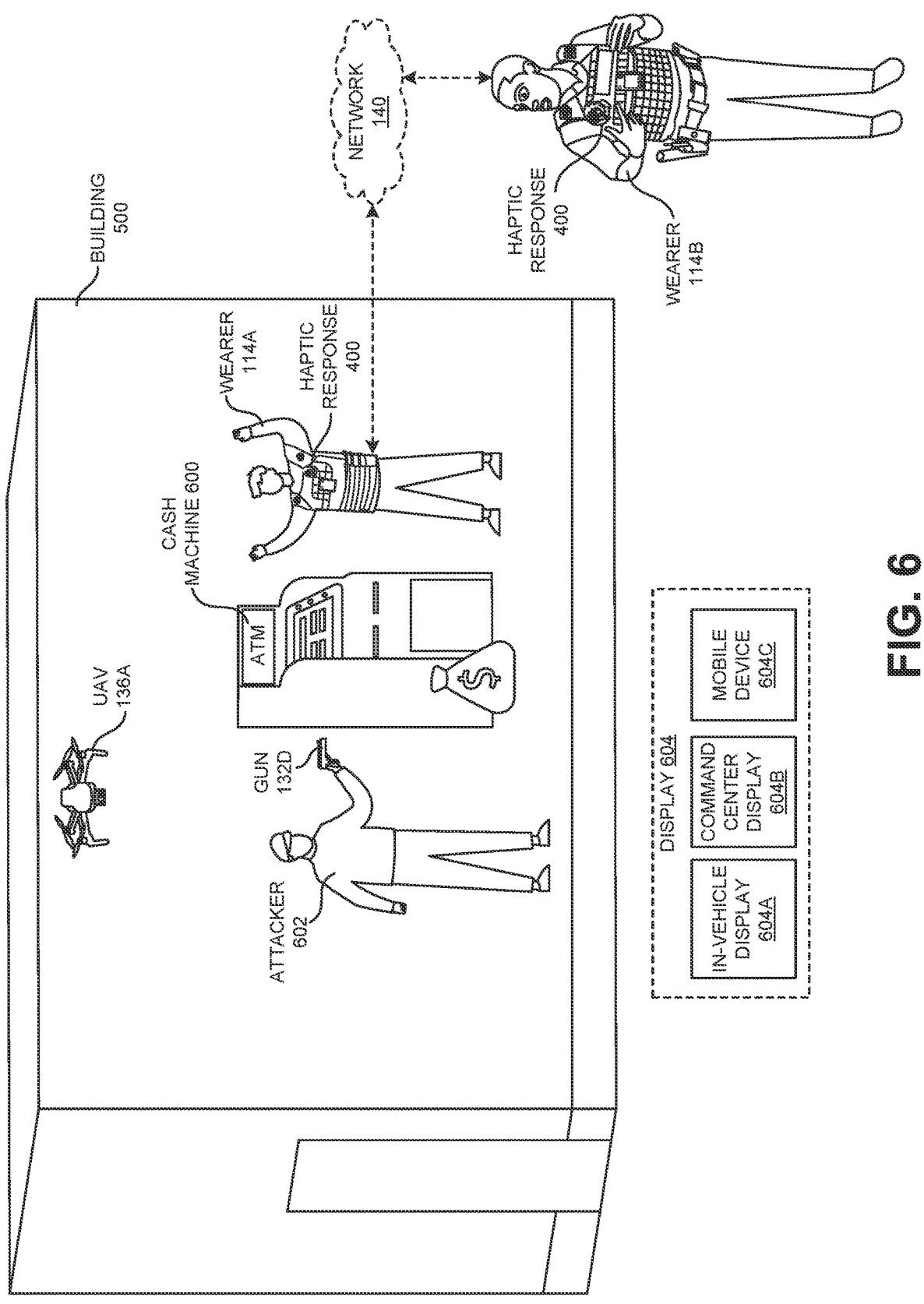
FIG. 6 is an operational view in which a UAV is directed through a drone control apparatus of a second wearer to travel inside of the building of FIG. 5 to inspect a location of a first wearer when a haptic response associated with an ambient threat of an attacker detected through a visual sensor of a tactical gear of the first wearer, according to one embodiment.

FIG. 6 is an operational view in which a UAV is directed through a drone control apparatus 124 of a second wearer 114B to travel inside of the building 500 of FIG. 5 to inspect a location of a first wearer 114A when a haptic response 400 associated with an ambient threat 132 of an attacker 602 is detected through a visual sensor 102 of a tactical gear 104 of the first wearer 114A, according to one embodiment. In FIG. 6, an intricate operational scenario is illustrated where a UAV 136A is commanded via a drone control apparatus 124 by a second individual, referred to as the second wearer 114B. This directive is in response to a situation involving the first wearer 114A, who has potentially encountered an ambient threat 132, identified by the attacker 602, within a building 500 previously described in FIG. 5, according to one embodiment. The UAV's task is to navigate inside the building 500 to closely inspect the situation surrounding the first wearer 114A, leveraging the intelligence gathered through the visual sensor 102 integrated into the first wearer's tactical gear 104, according to one embodiment.

This scenario exemplifies an advanced use of UAV technology in a tactical or law enforcement context, leveraging both aerial reconnaissance capabilities and ground-level operational coordination, according to one embodiment. The drone control apparatus 124 serves as an interface through which the second wearer 114B may swiftly command the UAV 136A to adapt its mission focus based on real-time developments, showcasing the system's dynamic responsiveness to evolving threat landscapes, according to one embodiment.

The concept of deploying a UAV 136A to inspect a location inside a building upon detection of an ambient threat 132 may introduce several strategic advantages in operational contexts:

Immediate Response: The UAV's rapid deployment may allow for an immediate evaluation of the threat scenario surrounding the first wearer 114A, according to one embodiment. This capability is critical in situations where every second counts, such as hostage situations (e.g., hostage 306 taken by the attacker 602 at gunpoint captured by UAV 136B in a crowded field 300 as shown in FIG. 3 and FIG. 6), active shooter incidents, or when navigating hazardous environments, according to one embodiment.

Enhanced Situational Awareness: By entering the building 500, the UAV 136A provides a direct visual feed from inside captured using camera 142, offering perspectives and information that might be inaccessible through external reconnaissance alone, according to one embodiment. This inside look may reveal the attacker's position, the condition and location of the first wearer 114A, and other critical factors influencing tactical decisions, according to one embodiment.

Increased Safety for Personnel: The UAV's ability to scout ahead and provide a real-time assessment minimizes the exposure of law enforcement or tactical team members (e.g., wearer 114) to potential threats (e.g., ambient threat 132A-J), according to one embodiment. By understanding the situation before making entry, teams may strategize their approach to maximize safety and effectiveness, according to one embodiment.

Operational Flexibility: The FIG. 6 scenario illustrates the UAV's versatility in transitioning from external to internal reconnaissance roles, underscoring the adaptability of UAVs in complex operational frameworks, according to one embodiment. This flexibility may be crucial in dynamic environments where conditions can change rapidly, according to one embodiment.

Integration with Tactical Gear: The interaction between the UAV 136A and the visual sensor 102 of the first wearer's tactical gear 104 may enable a cohesive operational approach, where wearable technology and UAV capabilities complement each other to enhance overall mission effectiveness, according to one embodiment.

In essence, FIG. 6 depicts a forward-thinking approach to utilizing UAVs within law enforcement and tactical operations, emphasizing real-time intelligence gathering, personnel safety, and operational adaptability, according to one embodiment. The ability of UAVs to perform such advanced tasks as inspecting locations inside buildings in response to detected threats represents a significant evolution in the capabilities available to law enforcement and security personnel, paving the way for more informed and effective response strategies, according to one embodiment.

In FIG. 6, the operational scenario presents a critical situation where an individual, identified as the first wearer 114A, is servicing a cash machine 600 located within a building 500. At this moment, an attacker 602, armed with a gun 132D, confronts the wearer 114A, posing a significant threat to their safety, according to one embodiment. This scenario vividly illustrates the risks associated with servicing and managing cash machines and Automated Teller Machines (ATMs), especially in locations where security may be compromised, according to one embodiment.

The invention addresses a paramount concern in the security and maintenance of cash and ATM machines: the safety of personnel during cash pickups (e.g., for example, handling cash and/or valuables-in-transit 138, etc.), servicing, and the general operation of these machines, according to one embodiment. Typically, servicing cash machines may involve transporting, loading, or retrieving cash, making these operations highly susceptible to robberies and armed assaults, according to one embodiment. The personnel performing these tasks may remain at constant risk, particularly in environments with inadequate security measures, according to one embodiment.

The solution offered by the various embodiments may enhance the safety of these operations through the utilization of advanced UAV and haptic technology made possible by generative artificial intelligence, according to one embodiment. By integrating UAVs into the security and surveillance system, the invention enables real-time monitoring and threat detection, which is crucial for preempting potential attacks and ensuring the safety of personnel, according to one embodiment. The UAV, directed through a drone control apparatus 124 by a second wearer 114B, may enter the building 500 to inspect the situation around the cash machine 600, providing a strategic advantage in several ways:

Immediate Threat Detection: The UAV 136A, equipped with visual sensors 102, may quickly identify the presence of an attacker 602, capturing crucial details such as their appearance, weapon, and actions, according to one embodiment. This real-time information may be invaluable for assessing the threat level and determining the appropriate response, according to one embodiment.

Enhanced Situational Awareness: By relaying live footage from inside the building, the UAV 136A may provide a comprehensive view of the environment, enabling remote operators or law enforcement to understand the dynamics of the situation without putting additional lives at risk, according to one embodiment.

Haptic Alert System: The integration of a haptic feedback mechanism may alert personnel to imminent dangers discreetly and efficiently, according to one embodiment. In this scenario, when the UAV detects the threat posed by the attacker 602, it may trigger a haptic response 400 in the tactical gear 104 of the first wearer 114A, according to one embodiment. This instant alert may provide the wearer 114B with a critical window to take defensive actions or retreat safely from the threat, according to one embodiment.

Operational Coordination and Response: The information gathered by the UAV may be used to coordinate a precise and informed response from law enforcement or security teams, minimizing the risk to all involved while maximizing the chances of apprehending the attacker without harm to the personnel or bystanders, according to one embodiment.

This inventive approach may solve a critical problem by significantly enhancing the safety protocols around servicing cash and ATM machines, according to one embodiment. It may transform a traditionally reactive security posture into a proactive, technology-driven strategy that prioritizes the safety of personnel through advanced surveillance, threat detection, and communication systems, according to one embodiment. This operational model may be adopted in various contexts where cash machines are serviced, offering a scalable solution to a widespread security challenge, according to one embodiment.

In the context of FIG. 6, the video footage captured by UAV 136A, while inspecting the situation inside building 500 where a first wearer 114A is confronted by an attacker 602 at a cash machine 600, plays a crucial role in the operational response and strategy, according to one embodiment. This footage may be displayed on various interfaces, including an in-vehicle display 604A, a command center display 604B, and mobile devices 604C like tablets or smartphones, according to one embodiment. The flexibility in the display options may ensure that critical information is accessible to relevant parties in real-time, facilitating immediate and informed decision-making, according to one embodiment.

In-Vehicle Display 604A: This may allow operatives in proximity to the incident, such as patrol vehicles 700 or security teams, to receive live footage directly in their vehicles, according to one embodiment. It may enable them to assess the situation while en route, preparing them for an immediate and appropriate response upon arrival, according to one embodiment. The in-vehicle displays 604A may be crucial for coordinating the first line of response in real-time situations, according to one embodiment.

Command Center Display 604B: A broader overview and long-term strategizing may be conducted here, where higher-level operational decisions are made, according to one embodiment. The command center 302 may access live feeds from multiple UAVs simultaneously, providing a comprehensive situational overview, according to one embodiment. This capability may be vital for allocating resources, providing backup, and engaging in negotiations or tactical planning with an overarching view of the situation, according to one embodiment. The command center 302 may be an onsite command center, such as a secure room at a police headquarter, correctional facility, and/or in a building. The command center 302 may also be a remote command center capable of dispatching resources to respond to incidents.

Mobile Device 604C (Tablets/Mobile Phones): The portability of mobile devices allows for flexible monitoring by on-ground personnel, higher-ups, or even off-site specialists who might be called upon for expert analysis or advice, according to one embodiment. It may ensure that critical information is not siloed but can be shared with all stakeholders, including tactical units, negotiators, or external support services, according to one embodiment.

Wireless Coupling and Network Infrastructure: The seamless integration and communication between drones like UAVs 136A, tactical gear 104, and the various display units may be enabled through wireless coupling over an internet or edge network, according to one embodiment. This network infrastructure facilitates a real-time data flow (e.g., realtime data 1112), which is essential for operational efficacy in critical situations, according to one embodiment. The use of edge computing may minimize latency, ensuring that the video feeds and sensor data from the drones are processed closer to where it is needed, thereby accelerating the response time, according to one embodiment.

The network's design may consider security protocols to safeguard the transmission of sensitive information against unauthorized access or cyber threats, according to one embodiment. This secure, efficient communication system allows for a coordinated response across different levels of operation, from immediate tactical actions to strategic oversight, ensuring that all parties are informed and aligned in their efforts to manage the situation effectively, according to one embodiment.

In summary, the provision to display drone footage on various platforms may enhance the operational capabilities of law enforcement and security teams, according to one embodiment. It bridges the gap between on-ground realities and command center 302 strategies, ensuring a united and informed response to incidents, particularly in high-risk scenarios like the one depicted in FIG. 6. This integrated approach exemplifies how advanced technology may significantly augment safety and efficiency in security operations, according to one embodiment.

Figure 7:
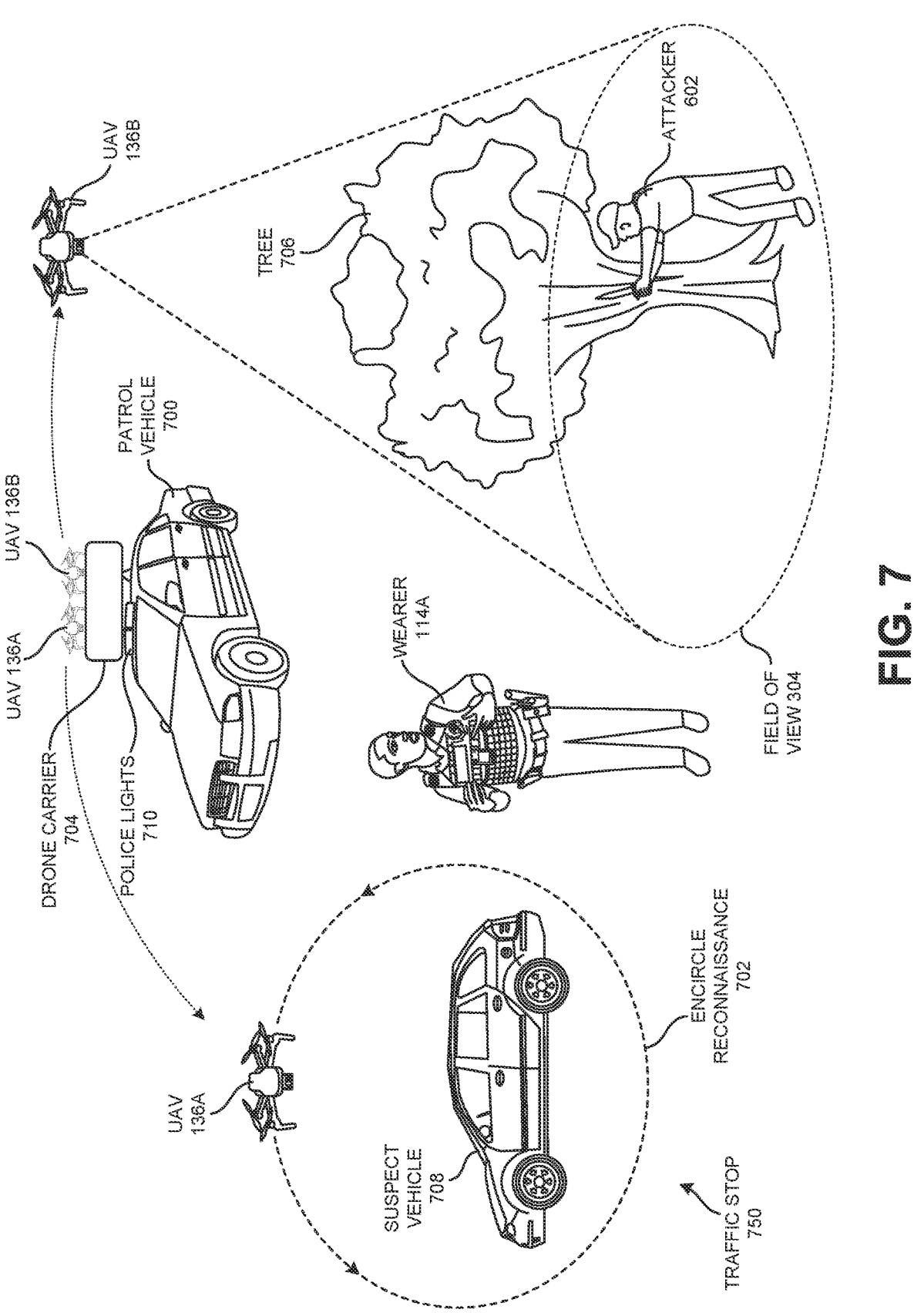
FIG. 7 is an operational view illustrating a first UAV performing an encircle reconnaissance of a suspect vehicle, and a second UAV detects an attacker behind a tree, after both the first UAV and the second UAV are launched from a vehicle (e.g., armored carrier, patrol vehicle) during a traffic stop, according to one embodiment.

FIG. 7 is an operational view illustrating a first UAV 136A performing an encircle reconnaissance 702 of a suspect vehicle 708, and a second UAV 136B detects an attacker 602 behind a tree 706, after both the first UAV 136A and the second UAV 136B are launched from a vehicle (e.g., armored carrier 134, patrol vehicle 700) during a traffic stop 750, according to one embodiment. FIG. 7 illustrates a dynamic operational scenario where Unmanned Aerial Vehicles (UAV) 136A and UAV 136B are deployed from a patrol vehicle 700 during traffic stop 750 while tracking a suspect vehicle 708. The patrol vehicle 700 may be equipped with a launch system and/or platform to launch the UAVs directly from the patrol vehicle 700 while following the suspect vehicle 708 during a traffic stop 750. Once launched, the first UAV 136A may perform an encircle reconnaissance 702 of a suspect vehicle 708 by flying in a pattern around the suspect vehicle 708 gathering realtime visual information from all angles using its camera and sensors.

This UAV 136A may serve a dual-purpose role by following the suspect vehicle 708 to provide real-time visual surveillance but also communicating critical threat information both visually and through haptic feedback mechanisms to involved personnel and the patrol vehicle 700, according to one embodiment. The haptic feedback mechanisms may trigger a haptic response 400 in the tactical gear 104 of the involved personnel (e.g., wearers 114) following the attacker 602 and the suspect vehicle 708 without getting out of the patrol vehicle 700, according to one embodiment.

Concurrently, the second UAV 136B may detect an "attacker 602" hiding behind a tree 706. This second UAV 136B may identify threats that are not visible to the wearer 114 on the ground due to obstructions or line-of-sight limitations. The attacker 602 may possibly remain undetectable by the wearer 114 without the assistance of the UAV 136B demonstrating the UAV's capability to detect hidden dangers.

This capability may ensure continuous observation, capturing vital details such as the suspect vehicle's movements and any interactions with the environment or other attacker 602, according to one embodiment. The live feed from the UAVs may be invaluable for tactical team inside the patrol vehicle 700, providing them with a bird's-eye view of the pursuit, which is crucial for strategizing interception tactics and predicting the suspect's next moves, according to one embodiment. The UAVs may significantly enhance officer safety and operational intelligence during traffic stops 750 by providing aerial reconnaissance and threat detection. The UAVs may function as airborne sentinels that can quickly and efficiently survey the scene from vantage points inaccessible to the officer on the ground, relaying critical information back to the law enforcement personnel. This immediate, tactile, visual, and/or auditory alert system may allow officers to react swiftly to evolving threats without needing to visually process information, according to one embodiment.

Figure 8:
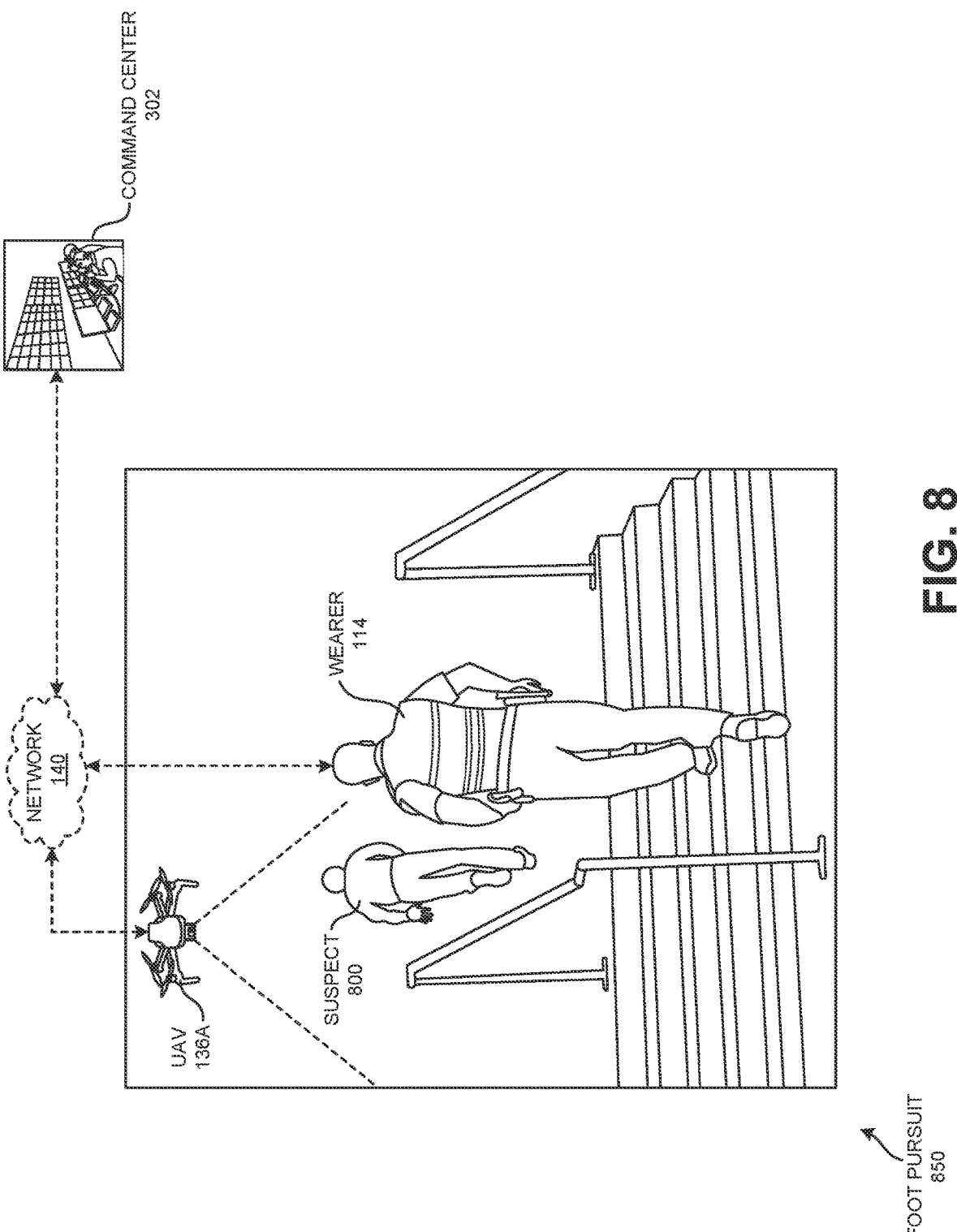
FIG. 8 is an operational view in which a UAV follows a suspect over a foot pursuit. It provides a visual view and/or haptic responses to the wearer and a command center based on a detected ambient threat, according to one embodiment.

FIG. 8 is an operational view in which a UAV 136A follows a suspect 800 over a foot pursuit 850, and provides a visual view and/or a haptic response 400 to the wearer 114 and a command center 302 based on a detected ambient threat 132, according to one embodiment. FIG. 8 illustrates a dynamic operational scenario where an Unmanned Aerial Vehicle (UAV) 136A is deployed in a foot pursuit 850 situation, tracking a suspect 800. This UAV 136A may serve a dual-purpose role: it not only follows the suspect 800 to provide real-time visual surveillance but also communicates critical threat information both visually and through haptic feedback mechanisms to involved personnel and a command center 302, according to one embodiment. This sophisticated approach to law enforcement and tactical operations show-cases how integration of UAV technology may enhance situational awareness and response capabilities during high-stakes scenarios, according to one embodiment.

The UAV 136A, equipped with high-definition cameras and potentially other sensory equipment, may maintain a visual lock on the suspect 800 throughout the foot pursuit 850, according to one embodiment. This capability may ensure continuous observation, capturing vital details such as the suspect's appearance, movements, direction of flight, and any interactions with the environment or other individuals, according to one embodiment. The live feed from the UAV may be invaluable for tactical teams on the ground, providing them with a bird's-eye view of the pursuit, which is crucial for strategizing interception tactics and predicting the suspect's next moves, according to one embodiment.

Concurrently, the UAV's 136A detection of any ambient threat 132—such as the suspect wielding a weapon or entering a densely populated area—may trigger a haptic response 400 in the tactical gear 104 of the involved personnel (e.g., wearers 114), according to one embodiment. This immediate, tactile, visual, and/or auditory alert system may allow officers to react swiftly to evolving threats without needing to visually process information, which may be especially beneficial in high-adrenaline situations where visual attention may be divided, according to one embodiment. The haptic feedback mechanism may act as a direct line of communication between the UAV's intelligence-gathering capabilities and the on-ground personnel's sensory awareness, enhancing safety and operational efficiency, according to one embodiment.

The visual feed and threat detection alerts may be simultaneously transmitted to a command center 302, where strategic oversight occurs, according to one embodiment. This may ensure that decision-makers have a comprehensive understanding of the situation as it unfolds, allowing them to allocate resources, provide additional support, or issue critical instructions to on-ground teams, according to one embodiment. The command center 302 may also use this information to coordinate with other law enforcement agencies, medical teams, or negotiation experts as required by the evolving scenario, according to one embodiment.

The seamless operation of this system—spanning UAV surveillance, haptic feedback, and command center coordination—may rely on robust wireless and network capabilities, according to one embodiment. These technologies may ensure the rapid, secure transmission of video feeds and sensor data across different platforms and participants in the operation, according to one embodiment. By leveraging advanced networking solutions, such as edge computing and secure communication protocols, the system may minimize latency and enhance the reliability of the information flow, which is crucial for the success of fast-paced tactical operations, according to one embodiment.

The scenario depicted in FIG. 8 highlights the transformative impact of UAV technology in enhancing law enforcement capabilities, according to one embodiment. By integrating aerial surveillance, real-time data analysis, and innovative communication methods, law enforcement agencies may significantly improve their response to dynamic situations like foot pursuits, according to one embodiment. This may not only increase the likelihood of apprehending suspects with minimal risk to civilian populations and officers but also exemplifies a shift towards more technologically advanced, data-driven operational tactics in public safety and security domains, according to one embodiment.

Figure 9:
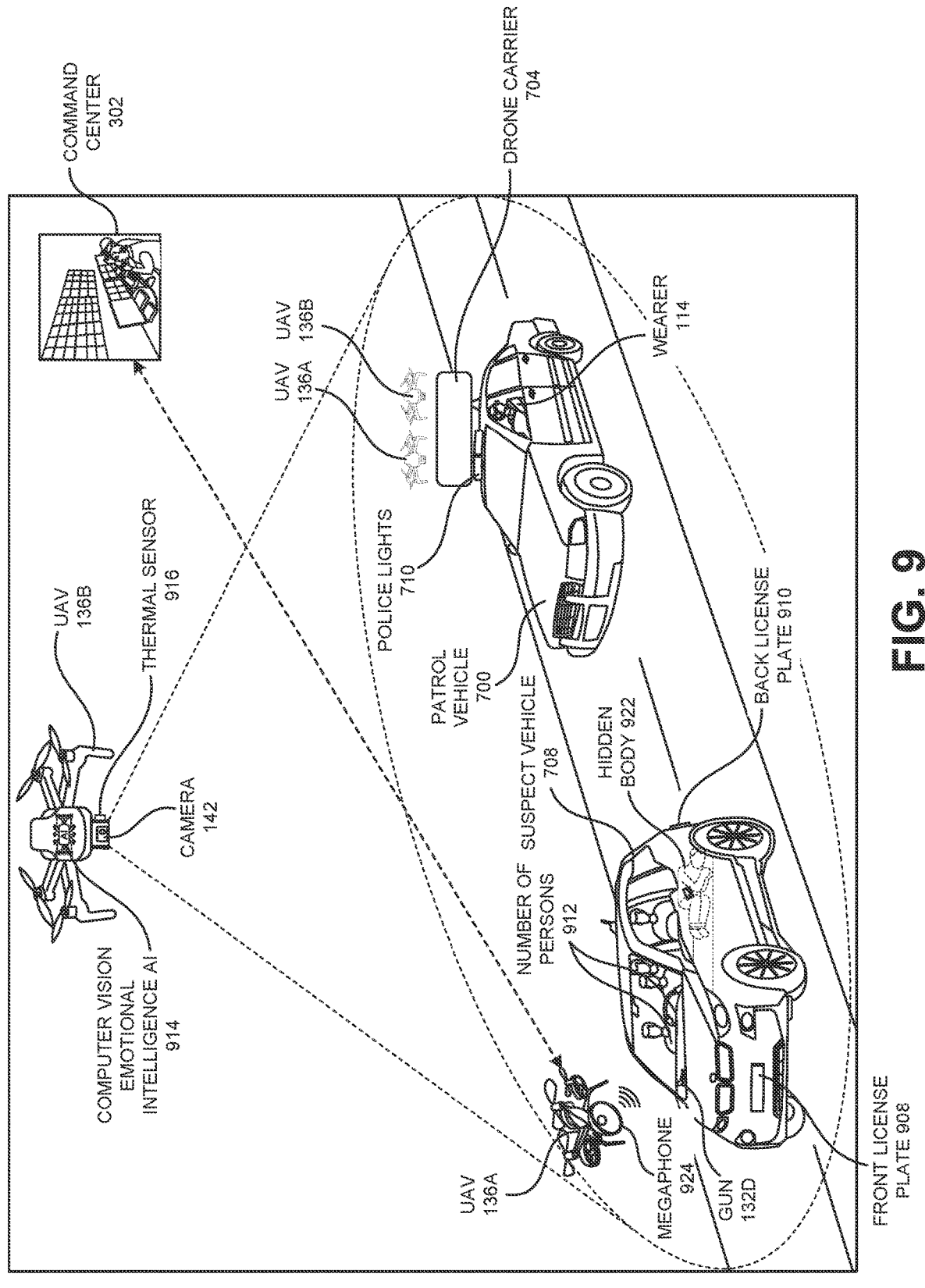
FIG. 9 is an operational view illustrating a first UAV using the sensors to identify a number of persons in a suspect vehicle, a gun in the suspect vehicle, a front license plate of the suspect vehicle, and a back license plate of the suspect vehicle, a hidden body in the suspect vehicle, after both the first UAV and the second UAV are launched from a vehicle (e.g., armored carrier, patrol vehicle) while the suspect vehicle is still moving, according to one embodiment.

FIG. 9 is an operational view illustrating a first UAV 136A using the sensors (e.g., a thermal sensor 916, a camera 142, auditory sensors, long distance sensors such as parabolic microphones, etc.) to identify a number of persons 912 in a suspect vehicle 708, a gun 132D in the suspect vehicle 708, a front license plate 908 of the suspect vehicle 708, and a back license plate 910 of the suspect vehicle 708, a hidden body 922 in the suspect vehicle 708, after both the first UAV and the second UAV are launched from a vehicle (e.g., armored carrier 134, patrol vehicle 700) while the suspect vehicle 708 is still moving, according to one embodiment.

In the described operational scenario, two Unmanned Aerial Vehicles (UAVs), 136A and 136B, may be deployed from a patrol vehicle 700, optionally triggered by the activation of police lights 710, according to one embodiment. This deployment may mark the initiation of a highly sophisticated and technologically advanced approach to law enforcement and surveillance operations involving a suspect vehicle 708, according to one embodiment. The UAVs may be equipped with an array of sensors and communication devices designed to assess, monitor, and engage with the situation in a manner that enhances safety, efficiency, and the effectiveness of law enforcement personnel, according to one embodiment.

UAV 136A may play a crucial role in visual and auditory surveillance, according to one embodiment as shown in FIG. 9 because it may be equipped with a megaphone 924 which allows the UAV to fly close to the ground next to the suspect vehicle 708 and relay messages directly to the driver of the suspect vehicle 708, according to one embodiment. In one embodiment, the megaphone 924 may relay a message directly from a remote command center 302 rather than the wearer 114. This capability may be used for giving commands, warnings, or attempting negotiation without exposing law enforcement personnel to potential threats, according to one embodiment. A camera 142 and sensory equipment such as a thermal sensor 916 may enable the UAV 136A to capture detailed visual information about the suspect vehicle 708, including the number of occupants (e.g., number of persons 912) and visible and hidden weapons like a gun 132D, according to one embodiment. The camera and additional sensors like parabolic microphones may enhance the UAV's ability to collect comprehensive data on the suspect vehicle's occupants and their actions, according to one embodiment.

UAV 136B may complement the capabilities of UAV 136A with a focus on detecting concealed threats using thermal sensor 916, according to one embodiment. This sensor allows the UAV to detect variations in temperature, which can be used to identify hidden compartments or bodies (e.g., hidden body 922) within the suspect vehicle 708, according to one embodiment. The thermal imaging may be invaluable in nighttime operations or scenarios where visibility is limited, offering a non-invasive means to assess potential threats hidden from plain sight, according to one embodiment.

Both UAVs work in tandem to encircle the suspect vehicle 708, offering a 360-degree surveillance capability in the embodiment of FIG. 9, according to one embodiment. This coordinated maneuver may enable them to verify the consistency of the vehicle's identification, such as matching the front license plate 908 with the back license plate 910, according to one embodiment. Such information is crucial for confirming the vehicle's identity, ownership, and potentially its involvement in criminal activities, according to one embodiment. The data and insights gathered by UAVs 136A and 136B are relayed back to the patrol vehicle 700 in real-time, according to one embodiment. This may ensure that the officers who are dispatched and at a control room at headquarters are well-informed about the situation, enabling them to make tactical decisions based on comprehensive situational awareness, according to one embodiment.

A noteworthy feature of these UAVs may be the integration of computer vision emotional intelligence AI 914 (AI), according to one embodiment. This advanced AI capability may allow the UAVs to not only capture and analyze visual and thermal data but also interpret subtle cues that may indicate stress, aggression, or other emotional states of the vehicle's occupants, according to one embodiment. By understanding these psychological and emotional dynamics, law enforcement may tailor their approach to de-escalate potentially volatile situations or anticipate aggressive behavior, significantly enhancing the chances of a peaceful resolution, according to one embodiment.

The automatic deployment of UAVs 136A and 136B upon the activation of police lights 710 may signify a protocol where the utilization of advanced surveillance technology is seamlessly integrated into routine police operations, according to one embodiment. This rapid deployment capability may ensure that law enforcement personnel are equipped with immediate aerial support during traffic stops, enhancing their ability to assess and respond to threats with a greater degree of safety and strategic advantage, according to one embodiment.

FIG. 10 is a haptic table 1050 associated with an array of haptic sensors 210 on the tactical gear 104 to reduce stress of the wearer 114 and remind of mindfulness, when the biometric sensor(s) 160 detect elevated stress markers on a wearer 114, according to one embodiment. The haptic table 1050 incorporates de-escalation techniques into the table with suggested haptic responses, according to one embodiment.

FIG. 10 introduces a sophisticated integration of technology and psychological insights through the concept of a haptic table 1050, which may be designed to enhance the operational effectiveness and well-being of personnel wearing tactical gear 104. The table delineates a series of haptic alert patterns generated by an array of haptic sensors 210 embedded in the gear, each corresponding to specific biometric triggers detected by biometric sensors 160. These triggers may include various physiological markers such as adrenaline levels, heart rate, and stress indicators, reflecting the wearer's emotional and physical state during high-pressure scenarios.

This system aims to provide immediate, intuitive feedback to the wearer 114, guiding them towards actions or mental exercises that may mitigate stress, enhance decision-making, and improve situational response. Below is an expanded explanation of the haptic table's components and their intended applications, according to one embodiment:

A continuous vibration 1002 haptic alert pattern may be triggered by a high adrenaline in the wearer 114 which may initiate an intended signal to the wearer 114 to pause and critically assess the situation, fostering a moment of mindfulness to prevent hasty decisions, according to one embodiment.

A pulsing vibration (Slow) 1004 haptic alert pattern may be triggered by an elevated heart rate in the wearer 114 which may intend to encourage the wearer 114 to initiate tactical breathing exercises, helping to lower the heart rate and calm the nervous system, according to one embodiment.

A pulsing vibration (Fast) 1006 haptic alert pattern may be triggered by a very high heart rate in the wearer 114 which may urge immediate physical action, such as seeking cover or assistance, indicating a situation that necessitates swift movement to ensure safety, according to one embodiment.

A single sharp vibration 1008 haptic alert pattern may be triggered by a sudden adrenaline spike in the wearer 114 which may act as an immediate alert to a potential threat or a critical decision point, enhancing the wearer's focus on immediate dangers or decisions, according to one embodiment. A wave pattern vibration 1010 haptic alert pattern may be triggered by elevated stress levels in the wearer 114 which may serve as a reminder to use communication skills and de-escalation techniques, aiming to lower both the wearer's and any involved parties' stress levels, according to one embodiment. Also, may tell the command to deploy different officers to assist.

A random pattern vibration 1012 haptic alert pattern may be triggered by an erratic heart rate or adrenaline levels of the wearer 114 which may indicate a need to check personal status for potential equipment malfunction or medical attention, addressing irregular physiological readings, according to one embodiment. A two-part vibration 1014 haptic alert pattern may be triggered by a moderate stress and adrenaline levels of the wearer 114 which may be a reminder to adhere to established protocols and training, reinforcing reliance on preparation and training to navigate the situation, according to one embodiment. A series of short vibrations 1016 haptic alert pattern may be triggered by an initial signs of conflict escalation which may prompt the use of active listening skills to de-escalate conflicts, emphasizing empathy, validation of feelings, and avoidance of confrontation, according to one embodiment.

A gentle rolling vibration 1018 haptic alert pattern may be triggered by persistent high stress detected in the wearer 114 which may intend to encourage offering choices to others involved, empowering them with control options to defuse stress and tension, according to one embodiment. An intermittent sharp pulses 1020 haptic alert pattern may be triggered by communication breakdown which may intend to advise practicing patience, suggesting a momentary step back to regroup and approach interactions with renewed understanding and patience, according to one embodiment. A long, followed by short vibrations 1022 haptic alert pattern may be triggered by the signs of verbal agitation of the wearer 114 which may recommend lowering the tone of voice, adjusting speaking volume and rate to a calm level to encourage a calmer response from others, according to one embodiment.

The haptic table 1050 and its associated alert patterns represent a groundbreaking approach to leveraging wearable technology for enhancing the psychological resilience and operational capacity of personnel in high-stress environments, according to one embodiment. By directly linking physiological indicators with actionable feedback, the system may provide a real-time, non-intrusive support mechanism to aid personnel in maintaining composure, making informed decisions, and effectively managing interactions and conflicts, thereby significantly contributing to the success and safety of operations, according to one embodiment. Furthermore, as shown in FIG. 10, the wearer 114 may have any number of responsive devices 106, which may form an array of haptic sensors 210 as illustrated in FIG. 10, according to one embodiment.

Figure 11:
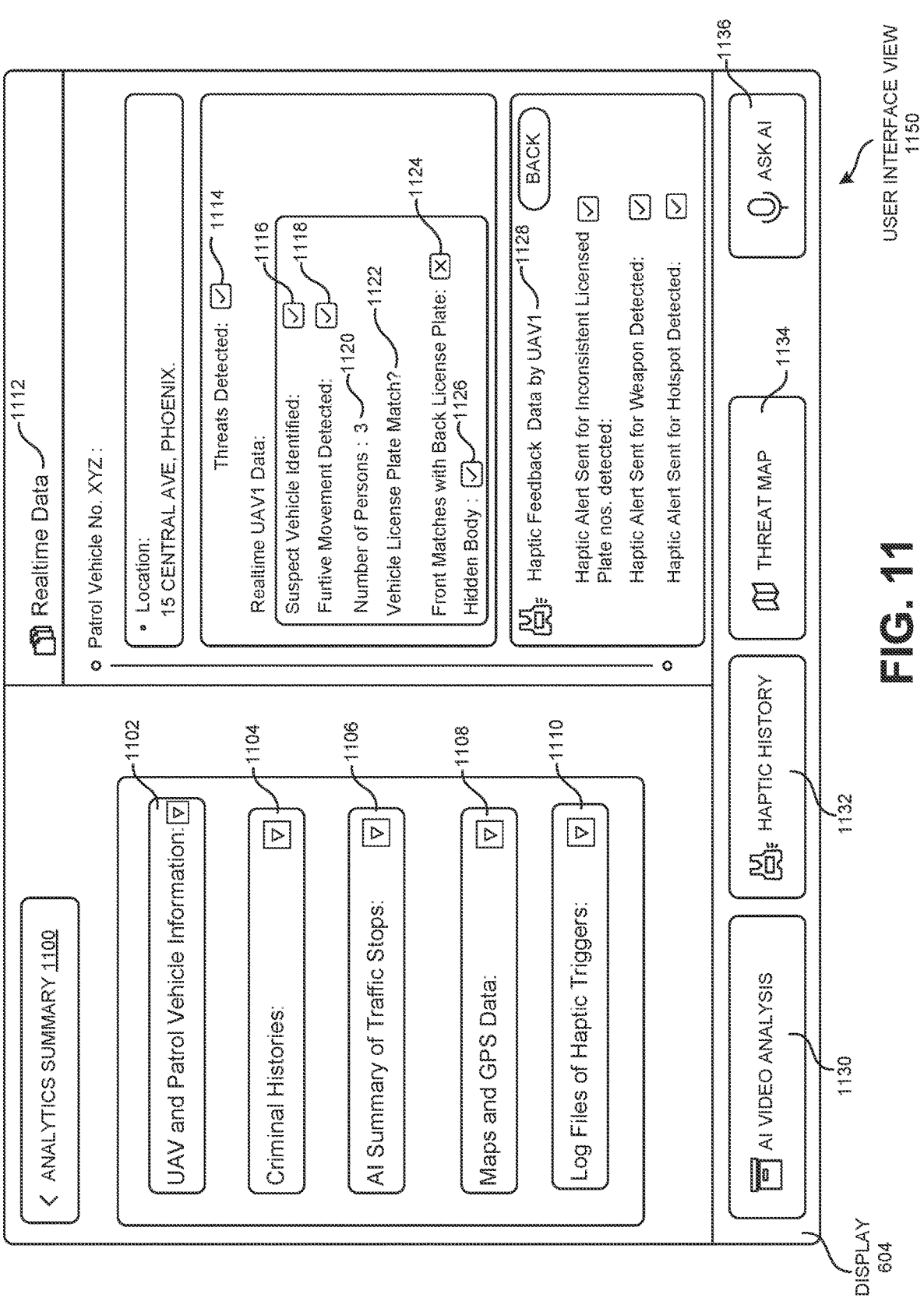
FIG. 11 is a user interface view showing a display in a vehicle (e.g., armored carrier, patrol vehicle) or in a computing device (e.g., a command center display, a tablet, etc.) describing results of advance work performed by a drone system along with a log file, according to one embodiment.

FIG. 11 is a user interface view 1150 showing a display 604 in a vehicle (e.g., armored carrier 134, patrol vehicle 700) and/or at a command center 302 describing results of advance work performed by a drone system 150 along with a log file of the haptic triggers 1110, according to one embodiment.

In FIG. 11, we delve into a comprehensive analytics summary 1100 derived from the advanced reconnaissance and operational efforts of Unmanned Aerial Vehicles (UAVs) 136 as part of a law enforcement operation, according to one embodiment. The analytics summary 1100 displayed on the user interface view 1150 provides a holistic overview of critical data points and operational insights, facilitating informed decision-making and strategic planning, according to one embodiment.

Detailed Components of the Analytics Summary 1100:

UAV and Patrol Vehicle Information (1102): This section may provide specifics on the UAVs and patrol vehicles 700 involved in the operation, including deployment times, operational status, and any relevant technical data that may impact their performance or effectiveness, according to one embodiment.

Criminal Histories (1104): If suspects are identified during the operation, this area may detail their criminal backgrounds, leveraging database integrations to pull historical data, according to one embodiment. This information may be crucial for assessing threat levels and planning appropriate responses, according to one embodiment.

AI Summary of Traffic Stop (1106): An AI-powered analysis may give a written-by-AI overview of how the traffic stop unfolded, using data from video feeds, audio captures, and sensor readings, according to one embodiment. This summary may highlight moments of compliance or resistance and provide insights into the suspects' behavior, according to an embodiment.

Maps and GPS Data (1108): Geolocation data may offer a spatial understanding of the operation, pinpointing the locations of UAVs 136A-N, patrol vehicles 700, suspects 800, and significant incidents, according to one embodiment. This real-time mapping may enhance situational awareness and tactical coordination, according to one embodiment.

Log File of Haptic Triggers (1110): May give a detailed record of instances when haptic feedback was activated on officers' tactical gear 104, including the stimuli that triggered these alerts, according to one embodiment. Analyzing these triggers may offer insights into stress points and potential dangers encountered during the operation, according to one embodiment.

Real-Time Data (1112): Live feeds from UAV cameras 142 and sensors (e.g., thermal sensor 916) may provide immediate visual and sensory information, allowing command centers 302 and field officers to monitor the situation as it evolves actively, according to one embodiment.

Operational Dashboard Checklists: The user interface may also feature a dashboard with key checklists for quick reference and assessment:

Threats Detected (1114): Confirmation of any threats identified by UAVs or officers on the ground, categorized by type and urgency, according to one embodiment.

Suspect Vehicle Identification (1116): Verification that the suspect vehicle 708 has been correctly identified, aiding in tracking and subsequent legal processes, according to one embodiment.

Furtive Movements Detected (1118): Observations of suspicious behaviors or movements that may indicate hidden threats or intentions to flee, according to one embodiment.

Number of Persons 912 in the Vehicle (1120): A count of individuals within the suspect vehicle 708, essential for assessing the situation and planning a response, according to one embodiment.

License Plate Verification (1122 and 1124): May check whether the vehicle's front and back license plates match each other and database records, a critical step in confirming the vehicle's identity and potential flags for stolen vehicles, according to one embodiment.

Hidden Body Detection (1126): Utilization of UAV thermal sensors to identify concealed individuals within the vehicle, may be an essential factor in risk assessment and operational planning, according to one embodiment.

Haptic Feedback Data by UAV (1128): This may provide a list of haptic feedback sent by the UAVs specifying the reason the haptic alert 2210 was generated by a particular UAV.

This analytics summary 1100 may embody the strategic integration of technology in modern law enforcement, providing a depth of operational intelligence previously unattainable, according to one embodiment. By leveraging UAVs 136, AI analysis (e.g., analytics summary 1100), and real-time data 1112, law enforcement agencies may significantly enhance their operational effectiveness, situational awareness, and safety protocols, paving the way for smarter, safer public safety solutions, according to one embodiment.

Expanding on the sophisticated features of the analytics summary 1100 illustrated in FIG. 11, the display interface, particularly when integrated within a patrol vehicle 700, includes additional crucial components designed to enhance operational clarity and interactive functionality, according to one embodiment. These components may cater to the modern demands of law enforcement operations, offering a blend of automated analysis (e.g., AI video analysis 1130), historical data review (e.g., haptic history 1132), strategic mapping (e.g., threat map 1134), and interactive AI querying using the ask AI button 1136, according to one embodiment.

AI Video Analysis 1130: This feature may employ advanced artificial intelligence algorithms to scrutinize video footage captured by UAVs in real-time, according to one embodiment. It may identify critical elements such as suspect behaviors, weapon presence, and unusual activities, providing a distilled analysis that helps in understanding the unfolding situation more deeply, according to one embodiment. This analysis may pinpoint moments of interest that may require further attention or immediate action, thus aiding officers in making informed decisions quickly, according to one embodiment.

Haptic History 1132: Given the importance of haptic feedback in modern tactical gear, this historical log may capture all instances where haptic alerts were triggered, the nature of these alerts, and the context in which they occurred, according to one embodiment. By reviewing the haptic history 1132, officers and command centers 302 may assess the frequency and severity of threats encountered during operations, offering insights into stress points and potential areas for operational adjustment or improvement, according to one embodiment.

Threat Map 1134: Integrating real-time data with geospatial analytics, the threat map may visually represent the location and nature of identified threats, plotted against the operational terrain, according to one embodiment. This dynamic mapping tool may allow officers to visualize the distribution of threats, plan navigation routes, and coordinate strategic positioning, according to one embodiment. The threat map 1134 may be essential for spatial analysis, helping to allocate resources effectively and anticipate potential challenges in the operation's environment, according to one embodiment.

Interactive AI querying enabled by the Ask AI Button 1136: Recognizing the value of immediate, context-specific information, the "Ask AI" feature may introduce an interactive dimension to the display interface, according to one embodiment. By pressing the Ask AI button, officers may engage with the onboard AI system, dubbed "DragonFly," using natural language queries, according to one embodiment. This functionality may allow officers to request information, clarify analysis outputs, or seek operational suggestions based on the AI's comprehensive understanding of the ongoing situation and accumulated data, according to one embodiment. For instance, an officer may ask, "Dragon-fly™, are there any known associates of the suspect 800 in the vicinity?" or "What's the safest approach route to the suspect vehicle 708?" The AI can then process the query against its database, real-time inputs, and analytical models to provide a concise, actionable response, according to one embodiment.

The integration of AI video analysis 1130, haptic history 1132, threat mapping 1134, and interactive AI querying into the patrol vehicle's display illustrating user interface view 1150 represents a significant leap forward in operational technology for law enforcement, according to one embodiment. This system may not only enhance situational awareness and decision-making efficiency but also fosters a proactive approach to public safety operations, according to one embodiment. By leveraging these advanced features, law enforcement agencies may navigate the complexities of modern operations with greater agility, precision, and confidence, ensuring a higher level of safety for both officers and the communities they serve, according to one embodiment.

FIG. 12 is a haptic gesture diagram 1250, depicting various haptic gestures 1270 to control the drone control apparatus 124, according to one embodiment. FIG. 12 shows three columns, functions 1260, haptic gesture 1270, and a description of the gesture 1280, according to one embodiment. Here are descriptions of each function 1260, according to one embodiment:

A 'swipe up' gesture may be used for an 'aerial reconnaissance 1202' function by executing a swift upward swipe on the drone control apparatus 124 touchpad to send a command to the drone, instructing it to rise to a predetermined altitude, according to one embodiment. This elevation may offer a wide-angle view of the area, essential for comprehensive surveillance and situational awareness, according to one embodiment.

A 'pinch and zoom-in' gesture may be used for 'close-up inspection 1204' by mimicking the pinch-and-zoom gesture familiar to smartphone users, officers to command the drone to decrease its altitude and approach a specific point of interest, according to one embodiment. This may allow for detailed inspections from a closer perspective, according to one embodiment.

A 'press and hold' gesture may be used for a 'static hover 1206' function by pressing and holding a designated area on the drone control apparatus 124 touchpad to instruct the drone to maintain its current position in the air, according to one embodiment. This functionality may be crucial for conducting sustained surveillance or while waiting for further orders, according to one embodiment.

A 'single tap' gesture may be used for a 'follow wearer 1208' function by a single tap on the drone control apparatus 124 touchpad to signal the drone to initiate following the officer, according to one embodiment. This may ensure the drone maintains a protective and observational stance over the officer during operations, according to one embodiment.

A 'double tap' gesture may be used for a 'follow suspect 1210' function through a double-tap gesture on the drone control apparatus 124 touchpad, the drone may receive a command to lock onto and follow a specified suspect 800, according to one embodiment. The way the drone determines which suspect to track may be based on a suspect vehicle 708 that has been stopped by the patrol vehicle 700 in which the wearer 114 is located. In one embodiment, the wearer 114 may simply point their finger to a suspect or in the direction of a suspect 800, and the visual sensor 102 on the tactical gear 104 may determine what is the best direction to travel. This feature may be vital for tracking movements without manual guidance, according to one embodiment.

A 'triple tap' gesture may be used for a 'follow suspect vehicle 1212' function through a triple tap on the drone control apparatus 124 touchpad to direct the drone to begin tracking the suspect's vehicle, enabling persistent surveillance of the vehicle's path and actions, according to one embodiment.

Draw a 'V' gesture may be used for a 'quick shift to suspect 1214' function by drawing a 'V' on the drone control apparatus 124 touchpad to allow officers to swiftly change the drone's focus from tracking a vehicle to following a suspect on foot, enhancing adaptability during pursuit scenarios, according to one embodiment.

Draw an 'S' gesture may be used for a 'dynamic adjustments 1216' function. This gesture may instruct the drone to modify its tracking behavior dynamically, such as changing its altitude or angle, ensuring optimal surveillance coverage, according to one embodiment.

A 'swipe down with two fingers' gesture may be used for a stealth mode for following 1218 function by activating stealth mode to significantly reduce the drone's visibility and noise, a critical feature when discreet surveillance is required, according to one embodiment.

Draw a 'T' gesture may be used for a stealth mode for 'tactical positioning ahead 1220' function by drawing a 'T' to command the drone to position itself ahead of a moving suspect or vehicle, predicting their path to provide advanced surveillance and coordination capabilities, according to one embodiment.

A 'swipe down' gesture may be used for a 'retreat and return 1222' function through a downward swipe to instruct the drone to either return to the officer for close support or to its base for recharging or safety, ensuring its readiness for subsequent deployments, according to one embodiment.

These haptic gestures may represent a breakthrough in the operational efficiency of drone-assisted law enforcement activities, according to one embodiment. By enabling officers (e.g., wearer 114) to intuitively control drones with simple touchpad inputs using the drone control apparatus 124 of the tactical gear 104, the system not only simplifies the complexities of drone operation but also significantly enhances the tactical flexibility and response capabilities of law enforcement personnel in the field, according to one embodiment.

These haptic gestures 1270 may represent a breakthrough in the operational efficiency of drone-assisted law enforcement activities, according to one embodiment. By enabling officers to intuitively control drones with simple touchpad inputs, the system not only simplifies the complexities of drone operation but also significantly enhances the tactical flexibility and response capabilities of law enforcement personnel in the field, according to one embodiment.

FIG. 13 is a process flow 1350 describing a series of operations of the drone control apparatus 124, according to one embodiment. In operation 1302, an unmanned aerial vehicle UAV 136A-N may be deployed from a vehicle (e.g., armored carrier 134) when the drone control apparatus 124 is activated by a wearer 114, according to one embodiment.

In operation 1304, the unmanned aerial vehicle UAV 136A-N may be summoned to a location in a visual field of view 304 of a camera 142 of the unmanned aerial vehicle UAV 136B in which the wearer 114 and an ambient environment around the wearer 114 is observable through a first action on the drone control apparatus 124, according to one embodiment.

In operation 1306, the unmanned aerial vehicle (UAV) 136A may be summoned to a location in a visual field of view 304 of a camera 142 of the unmanned aerial vehicle (UAV) 136A in which the suspect 800 and an ambient environment around the suspect 800 is observable through a second action on the drone control apparatus 124, according to one embodiment.

In operation 1308, the unmanned aerial vehicle (UAV) 136A may be summoned to a location in a visual field of view 304 of a camera 142 of the unmanned aerial vehicle (UAV) 136A in which the suspect vehicle 708 and an ambient environment around the suspect vehicle 708 is observable through a third action on the drone control apparatus 124, according to one embodiment. In operation 1310, the unmanned aerial vehicle (UAV) 136A may encircle at least one of a building 500 and a suspect vehicle 708.

In operation 1312, unmanned aerial vehicle (UAV) 136A may auditorily communicates a message to the driver of the suspect vehicle 708 when the wearer 114 speaks into a microphone in the patrol vehicle 700, and/or another microphone on the drone control apparatus 124 on tactical gear 104 when the drone control apparatus is depressed 124.

The message may be delivered directly from a command center 302 in an attempt to de-escalate the situation and encourage peaceful surrender of the suspect 800 in a manner which is adapted its communication style based on the suspect 800 responses, background information, and/or predefined protocols to increase the chances of compliance, according to one embodiment. It should be noted that while a touchpad version of the drone control apparatus 124 is illustrated, other embodiments are possible. For example, in one embodiment, the drone control apparatus 124 might operate purely through human speech and direction, as opposed to using hands on a touchpad of the drone control apparatus 124. In another embodiment, the drone control apparatus 124 may include a built in language translator module 144 to enable the wearer 114 to communicate with the suspect 800 in any language, bidirectionally, according to one embodiment.

FIG. 14 is a process flow 1450 describing a series of operations the drone system 150 may automatically take when launched from a vehicle (e.g., armored carrier 134, patrol vehicle 700), according to one embodiment. In operation 1400, an unmanned aerial vehicle UAV 136A-N may be automatically launched from a patrol vehicle 700 when a suspect vehicle 708 is still moving when the wearer 114 activates police lights 710 on the patrol vehicle 700. In operation 1402, the system may perform an advance work prior to the wearer 114 exiting the patrol vehicle 700, and any issues are displayed on the display 604A on the patrol vehicle 700 as the advance work is being carried out. In operation 1404, the system may quantify a number of persons 912 in the suspect vehicle 708 using computer vision based artificial intelligence, and notify the wearer 114 through the display 604A in the patrol vehicle 700 and the responsive device 106 when the ambient threat 132 is detected, according to one embodiment.

The advance work may include automatically detecting when the suspect 800 intentionally leaves behind an item 308 comprising a backpack, package, and any object that can pose a potential threat through object detection and a behavior of placing items down and then departing without them to determine a security threat level, according to one embodiment.

In operation 1406, the system may detect any one or more of the ambient threat 132, including a weapon, a furtive movement 132F, and an illegal substance 132G in the suspect vehicle 708 through computer vision based artificial intelligence, according to one embodiment.

In operation 1408, the unmanned aerial vehicle UAV 136A may utilize an infrared sensing to determine a hotspot in the vehicle 708, and notify the wearer 114 through the display 604A in the patrol vehicle 700 and the responsive device 106 when the hotspot is something that the wearer 114 needs to investigate, according to one embodiment.

In operation 1410, the system may describe the reasons why a haptic response 400 was triggered on the personal protective equipment 100 on the display 604A in the patrol vehicle 700, according to one embodiment.

Figure 15:
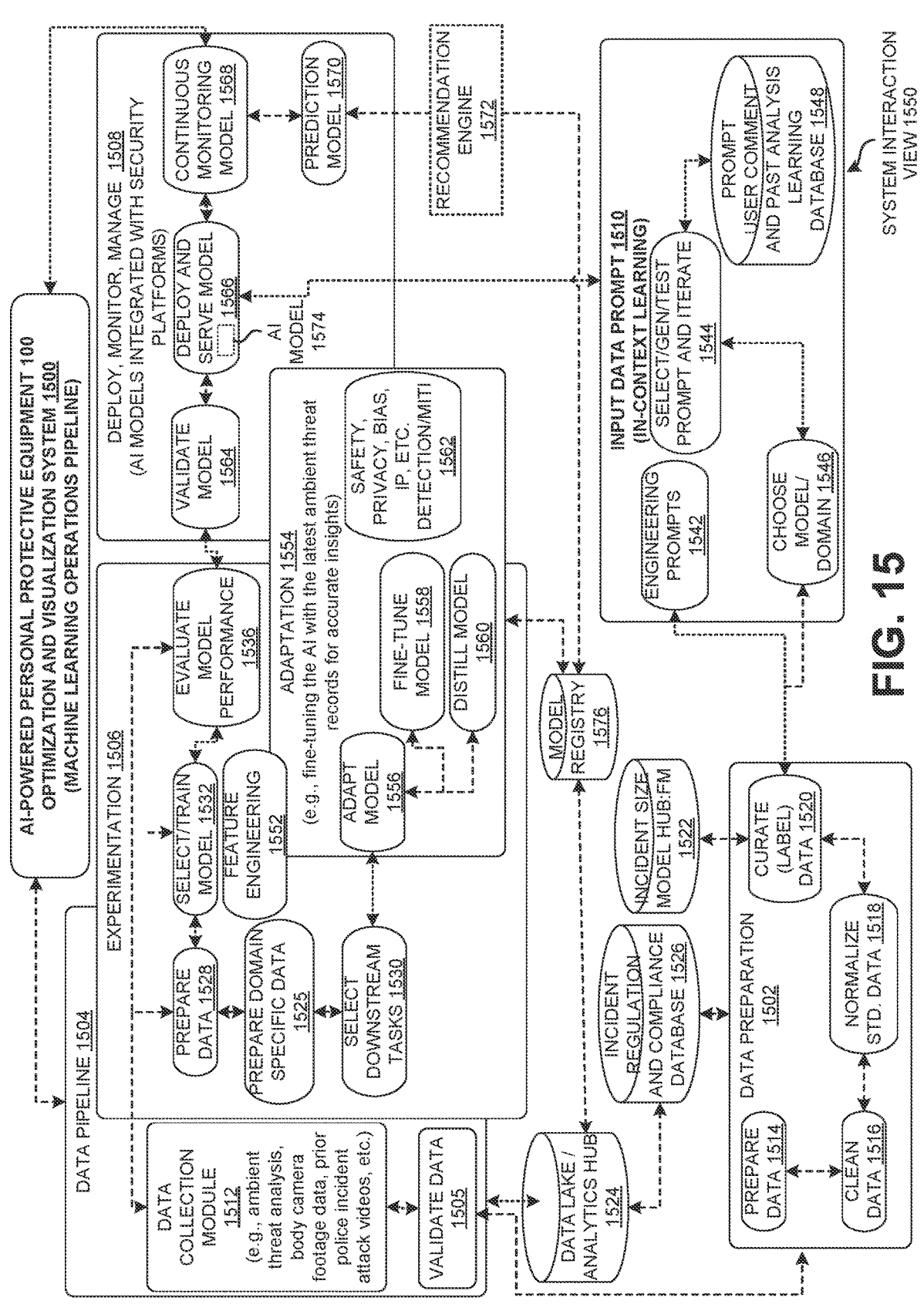
FIG. 15 is a system interaction view that visually represents the intricate process of developing and implementing generative AI models within the personal protective equipment of FIG. 1, according to one embodiment.

FIG. 15 is a system interaction view 1550 that visually represents the intricate process of developing and implementing generative AI models within the context of Gov-GPT™ AI-powered personal protective equipment 100 optimization and visualization system 1500. The lifecycle of this system may ensure that it not only processes and categorizes tactical gear 104 ambient data efficiently but also provides insightful analytics and interactive visualizations to users. Below is a summary of each element:

Data Pipeline 1504: This involves collecting (e.g., using data collection module 1512 of the data pipeline 1504) and validating a wide range of data (e.g., using validate data 1505 of the data pipeline 1504), including the personal protective equipment 100 ambient data, captured conversations, and sentiment analysis. The ambient data may include the body camera footage data, the incident sensory data, ambient threat analysis, and the prior police incident attack videos, etc. The data then flows into a data lake or analytics hub 1524 and feature store for subsequent tasks. In Gov-GPT™ pendant's context, the Data Pipeline 1504 may involve collecting and validating data pertinent to public opinions, pre-incident video data, public record with prior police incident videos of police being attacked by ambient threats, body camera footage, history of crowd dynamics and behavior, etc., according to one embodiment The data preparation 1502 may be the process of preparing raw data extracted from the data lake and/or analytics hub 1524 based on the prompt received from a user so that it is suitable for further processing and analysis by the AI-powered personal protective equipment 100 optimization and visualization system 1500. The data preparation 1502 may include collecting, cleaning, and labeling raw data into a form suitable for machine learning (ML) algorithms and then exploring and visualizing the data. The data preparation 1502 phase may include prepare data 1514, clean data 1516, normalize standardized data 1518, and curate data 1520. The prepare data 1514 may involve preprocessing the input data (e.g., received using the data collection module 1512) by focusing on the data that is needed to design and generate a specific data that can be utilized to guide data preparation 1502. The prepared data 1514 may further include conducting geospatial analysis to assess the physical attributes of each incident, etc. In addition, the prepared data 1514 may include converting text to numerical embeddings and/or resizing images for further processing, according to one embodiment.

The clean data 1516 may include cleaning and filtering the data to remove errors, outliers, or irrelevant information from the collected data. The clean data 1516 process may remove any irrelevant and/or noisy data that may hinder the AI-powered optimization and visualization system 1500, according to one embodiment.

The normalize standardized data 1518 may be the process of reorganizing data within a database (e.g., using the data lake and/or analytics hub 1524) of the AI-powered personal protective equipment 100 optimization and visualization system 1500 so that the AI model 1574 may utilize it for generating and/or address further queries and analysis. The normalize standardized data 1518 may be the process of developing clean data from the collected data (e.g., using the collect data module 1512) received by the database (e.g., using the data lake and/or analytics hub 1524) of the AI-powered personal protective equipment 100 optimization and visualization system 1500. This may include eliminating redundant and unstructured data and making the data appear similar across all records and fields in the database (e.g., data lake and/or analytics hub 1524). The normalize standardized data 1518 may include formatting the collected data to make it compatible with the AI model 1574 of the AI-powered personal protective equipment 100 optimization and visualization system 1500, according to one embodiment.

The curate data 1520 may be the process of creating, organizing and maintaining the data sets created by the normalize standardized data 1518 process so they can be accessed and used by people looking for information. It may involve collecting, structuring, indexing and cataloging data for users of the AI-powered personal protective equipment 100 optimization and visualization system 1500. The curate data 1520 may clean and organize data through filtering, transformation, integration and labeling of data for supervised learning of the AI model 1574. Each data in the AI-powered personal protective equipment 100 optimization and visualization system 1500 may be labeled based on whether they are suitable for processing. The normalize standardized data 1518 may be labeled based on the incident size model hub 1522 and input data prompt 1510 of the database (e.g., using incident regulation and compliance database 1526), according to one embodiment.

The data lake and/or analytics hub 1524 may be a repository to store and manage all the data related to the AI-powered personal protective equipment 100 optimization and visualization system 1500. The data lake and/or analytics hub 1524 may receive and integrate data from various sources in the network to enable data analysis and exploration for optimization and visualization, according to one embodiment.

Experimentation 1506: This phase includes preparing data 1528, engineering features 1552, selecting and training models 1532, adapting the model 1556, and evaluating the model's performance 1536. Experimentation 1506 in Gov-GPT™ personal protective equipment's case may encompass the AI analyzing various ambient scenarios and sensors of the tactical gear 104 to suggest the most prevalent concerns and sentiments, according to one embodiment.

In the adaptation 1554 phase, the machine learning models may adapt and improve their performance as they are exposed to more data by fine tuning (e.g., using the fine-tune model 1558) the adapt model 1556 for a specific threat incident and include additional domain specific knowledge. The adapt model 1556 may modify the model architecture to better handle a specific task. The fine-tune model 1558 may train the model on a curated dataset of high-quality data by optimizing the hyperparameters to improve model performance. The distill model 1560 may simplify the model architecture to reduce computational cost by maintaining and improving model performance. The system may implement safety, privacy, bias and IP safeguards 1562 to prevent bias and discrimination while predicting a threat incident. The system may ensure model outputs are fair and transparent while protecting the sensitive data as well.

Maturity Level 1: Prompt (e.g., using engineering prompts 1542), In-Context Learning, and Chaining: At this stage, a model is selected from the model registry 1576 using the choose model/domain 1546 and prompted (e.g., input data prompt 1510 in-context learning of the data pipeline 1504) to perform a task, according to one embodiment. The responses are assessed and the model is re-prompted using the select/gen/test prompt and iterate 1544 if necessary. In-context learning (ICL) may allow the model to learn from examples without changing its weights (e.g., using the prompt user comment and past analysis learning database 1548 in-context learning of the data pipeline 1504). In GovGPT™ tactical gear 104, Prompt and In-Context Learning can involve prompting the AI with specific ambient and sensor data and learning from past analyses to enhance its predictive capabilities, according to one embodiment.

Chain it: This involves a sequence of tasks starting from data extraction, running predictive models 1570, and then using the results to prompt a generative AI model 1574 to produce an output. In GovGPT™ tactical gear 104, Chain it can mean applying predictive analytics to ambient signal data to inform civic engagement and policy decisions, according to one embodiment.

Tune it: Refers to fine-tuning the model 1558 to improve its responses. This includes parameter-efficient techniques and domain-specific tuning (e.g., using the prepare domain specific data 1525 and select downstream tasks 1530). In GovGPT™ tactical gear 104, tune it may involve fine-tuning the AI using the fine-tune model 1558 with the latest ambient data captured from tactical gears deployed, according to one embodiment.

Deploy, Monitor, Manage 1508: After a model is validated (e.g., using the validate model 1564), it is deployed (e.g., using the deploy and serve model 1566), and then its performance is continuously monitored using the continuous monitoring model 1568, according to one embodiment. Deployment in GovGPT™ tactical gear's case may see the AI being integrated into municipal platforms, where it can be monitored and managed as users interact with it for tactical gear 104 ambient data analysis, according to one embodiment.

Maturity Level 3: RAG it & Ground it: Retrieval Augmented Generation (RAG) is used to provide context for the model by retrieving relevant information from a knowledge base, according to one embodiment. Grounding ensures the model's outputs are factually accurate. In GovGPT™ tactical gear 104, RAG and Grounding may be utilized to provide contextually relevant information from civic databases to ensure recommendations (e.g., generated using the recommendation engine 1572 of the data pipeline 1504) are grounded in factual, up-to-date ambient signal and policy data, according to one embodiment.

FLARE it: A proactive variation of RAG that anticipates future content and retrieves relevant information accordingly. In GovGPT tactical gear 104, FLARE it can predict future trends in opinion or emerging community concerns that can affect policy-making, according to one embodiment.

CoT it or ToT it. GOT it: These are frameworks for guiding the reasoning process of language models, either through a Chain of Thought, Tree of Thought, or Graph of Thought, allowing for non-linear and interconnected reasoning. In GovGPT™ tactical gear 104, CoT, ToT, GOT frameworks may guide the AI's reasoning process as it considers complex opinion patterns, ensuring it can explore multiple outcomes and provide well-reasoned, data-driven insights, according to one embodiment.

FIG. 16 illustrates the innovative application of "Generative AI in Personal protective equipment 100 Management using an Integrated AI-Powered Ambient Threat Detection Model 108," as conceptualized in one embodiment of the GovGPT™ tactical gear 104 system. It highlights how artificial intelligence, particularly generative AI, may revolutionize the way ambient data are processed, analyzed, and utilized in governmental, military, law enforcement, fire and civic uses, according to one embodiment. The image is divided into three sections:

Types of AI Enablement Tailored for Analyzing and Managing Ambient Data 1602: This section showcases generative AI foundation models specifically tailored for analyzing and managing ambient data 1604. It emphasizes the system's capability to understand global and ambient opinion trends 1606 and to extract meaningful insights from a vast array of ambient sensors. This process may particularly involve generative info collection such as ambient sensor data and situational awareness trends 1642, generative research 1644 and meaningful insights for ambient threat detection 1646, generative automation 1648, generative innovation 1652 in personal protective equipment 100, and making generative data-driven decisions 1610, according to one embodiment.

AI-Enabled Knowledge Integration for Public Safety Administration 1608: This part emphasizes the AI's capabilities in transforming the way government officials and agencies engage with their constituents. It highlights how the AI aids in making data-driven decisions, ensuring law enforcement and security personnel safety 1622, ethics 1624, and compliance 1626 within the realms of public safety administration and policy-making.

Transforming Ambient Environment Engagement and Policy-making 1612: The final section is divided into strategic tasks 1620 such as identifying emerging ambient sensor-captured concerns and trends 1614 that can influence policy decisions, and tactical tasks 1628 like streamlining the processing of ambient sensors 1618, optimizing data integration 1638, and enhancing the responsiveness 1616 of military, law enforcement, and first responder bodies, according to one embodiment. The strategic tasks may further include pursuing mission parameters and visual surveillance data 1640, providing accurate analysis of crowd dynamics to enhance decision making process 1634, creating and using unique knowledge 1636, communicating and collaborating 1630 for making better decisions faster 1632 by gathering needed information 1654. The visualization serves as a powerful explanation of GovGPT™ tactical gear's role in pioneering the future of ambient personal protective equipment 100 computing, according to one embodiment.

FIG. 16 demonstrates the transformative impact of AI on governance and security personnel safety management, particularly through the analysis of ambient signals, according to one embodiment. Strategically, the AI identifies emerging issues and trends 1614 in ambient signals, informing policymakers (e.g., communicating+collaborating 1630) about the pressing concerns of their constituents. This insight can be crucial in addressing societal challenges and improving community relations. It also enhances the decision-making process (e.g., by making better decisions faster 1632) by providing accurate analysis of crowd dynamics to enhance the decision making process 1634, using unique knowledge 1636, optimizing data integration 1638, and pursuing mission parameters and visual surveillance data 1640, according to one embodiment. This integration of AI in public administration represents a significant advancement in enhancing democratic engagement, making the public consultation process more accessible and impactful, according to one embodiment.

Figure 17:
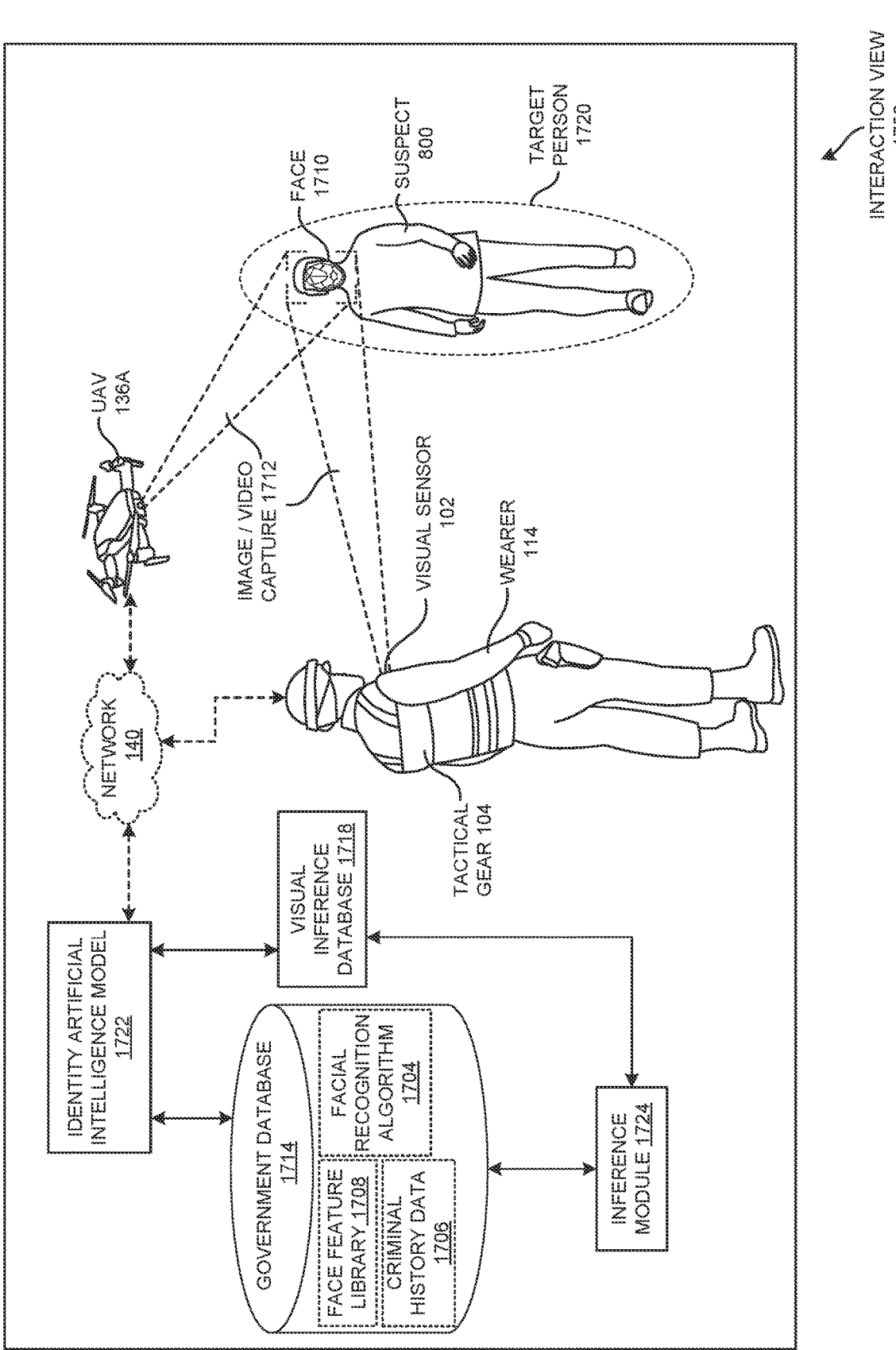
FIG. 17 is an interaction view that depicts a suspect as a target person with a face that is detected by a visual sensor, and wherein the face is associated with a visual inference database and/or a government database, according to one embodiment.

FIG. 17 is an interaction view 1750 that depicts a suspect 800 as a target person 1720 with a face 1710, according to one embodiment. FIG. 17 illustrates a wearer 114 who sees a face 1710 (or a gait movement) of the suspect 800 in a field of view of the visual sensor 102 on the tactical gear 104 of the wearer 114. When that happens, the image/video captured 1712 (which may also be captured by the UAV 136A which sees the face 1710 of the suspect 800 from the sky) uses the identity artificial intelligence model 1722 to determine that the suspect 800 is associated with a target person 1720, according to one embodiment. The tactical gear 104 and the UAV 136A may access the identity artificial intelligence model 1722 through the network 140, according to one embodiment. When forming an opinion, the identity artificial intelligence model 1722 may consult a database 1714, which may include a facial recognition technology (algorithm and/or e.g., facial recognition algorithm 1704), a criminal history data 1706, and a face feature library 1708, according to one embodiment.

Facial recognition technology (e.g., using the facial recognition algorithm 1704 of the government database 1714) may work by identifying and verifying a person's face from a digital image (e.g., using photograph 1808) or video frame (e.g., using video data 1804), according to one embodiment as follows: The first step may be to detect a face 1710 in the image or video capture 1712 using the visual sensor 102 of the tactical gear 104. This may involve identifying the presence of any faces in a given digital frame. Modern facial recognition systems may detect faces in various positions (e.g., front, side), with different facial expressions, and under a variety of lighting conditions, according to one embodiment. Once a face is detected, the next step may be to analyze the facial features using the facial recognition algorithm 1704 of the government database 1714. The software may read the geometry of the face, including key points and contours of the eyes, nose, checks, mouth, and jawline. The advanced algorithms may map out the facial geometry to create a facial signature, a unique numerical code for that face 1710, according to one embodiment.

The analysis results in a digital representation of the face 1710, may be called a facial signature and/or template, according to one embodiment. This template may be a mathematical formula that describes the key features of the face in a way that can be easily compared with other faces in the face feature library 1708 of the government database 1714, according to one embodiment.

The facial signature may then be compared with a database of known faces in the face feature library 1708 to find a match. In verification systems (like unlocking a smartphone), the software compares the captured facial signature to the owner's facial signature. In identification systems (such as surveillance), the captured facial signature may be compared against a database (e.g., criminal history data 1706 in conjunction with the face feature library 1708 of the government database 1714) to find out if there's a match with any entries, according to one embodiment.

The system may then decide whether there is a match based on a threshold. If the similarity between the facial signatures exceeds a certain threshold, it may be considered a match; otherwise, it's not, according to one embodiment. Facial recognition technology may use machine learning algorithms (e.g., identity artificial intelligence model 1722 and facial recognition algorithm 1704 of the government database 1714) and, especially deep learning, to improve accuracy and efficiency. The more the system is used, the better it gets at recognizing faces, even with variations in lighting, facial expressions, and angles, according to one embodiment.

The Identity Artificial Intelligence (AI) Model 1722 may be a comprehensive AI system designed to analyze visual data in real-time to identify individuals based on facial features, gait patterns, and other biometric markers, according to one embodiment. It may utilize deep learning algorithms to improve accuracy and adapt to various environmental conditions, such as lighting and angles, according to one embodiment. This identity AI model 1722 may be accessible via a secure network, enabling both wearable devices like tactical vests and UAV 136 to query the identity AI model 1722 for identity verification tasks, according to one embodiment. It processes incoming visual data and cross-references it with integrated databases to confirm (e.g., using the inference module 1724) the identity of suspect 800 within its field of view, according to one embodiment.

The facial recognition technology (e.g., using the facial recognition algorithm 1704 of the government database 1714) may form a core component of the Identity AI Model 1722, specializing in the analysis of facial data, according to one embodiment. It may compare captured images against a face feature library 1708 to find matches, using sophisticated pattern recognition and machine learning techniques to handle variations in expression, orientation, and partial obstructions, according to one embodiment. To maintain high accuracy levels, the algorithm may be subjected to continuous learning processes, where it is periodically updated with new data to enhance its recognition capabilities and adapt to evolving facial recognition technologies, according to one embodiment.

The criminal history data 1706 may contain detailed records of individuals with criminal histories, providing a comprehensive background that includes mugshots, physical descriptions, and known aliases, according to one embodiment. It may serve as a critical reference point for the identity AI model 1722 when identifying suspects and assessing potential threats, according to one embodiment. Access to criminal history data 1706 may be tightly controlled, with encryption and authentication measures in place to ensure that sensitive information is protected and only accessible to authorized personnel and systems, according to one embodiment. The face feature library 1708 may be an extensive collection of facial feature data used by the facial recognition algorithm 1704 to identify individuals, according to one embodiment. It may include geometric data, texture patterns, and other distinguishing features that may be used to accurately match faces from visual inputs, according to one embodiment. To ensure the effectiveness of facial recognition across diverse populations, the library may include a wide range of demographic data, according to one embodiment. Efforts may be made to continually expand and diversify the library to minimize bias and improve recognition accuracy across all ethnicities and genders, according to one embodiment.

When a wearer 114 of the tactical gear 104 or a UAV captures an image or video of a suspect 800, the data may be transmitted to the Identity AI Model 1722 via a secure network 140, according to one embodiment. The Identity AI Model 1722 may then consult the government database 1714, utilizing the Facial Recognition Algorithm 1704 to parse the Criminal History Data 1706 and reference the Face Feature Library 1708, according to one embodiment. Through this process, the identity AI model 1722 may determine whether the suspect 800 matches a target person 1720 of interest, according to one embodiment. If a match is confirmed (e.g., using inference module 1724), the system may alert the wearer 114, enabling law enforcement to take appropriate action based on real-time, accurate identification, according to one embodiment.

The suspect 800 may be an individual identified as a potential source of threat or interest during law enforcement, security, or surveillance operations. The face 1710 may be detected by a visual sensor 102 on a tactical gear 104 of a wearer 114, according to one embodiment. The face 1710 may be a front part of a person's head, extending from the forehead to the chin and including the mouth, nose, eyes, and checks, according to one embodiment. It's a distinctive feature used for recognizing individuals and is crucial for human identity and communication, according to one embodiment. Faces are expressive, capable of displaying a wide range of emotions through various muscle movements. In addition to its role in personal identification and emotional expression, the human face also plays a vital role in social interactions, including speech, nonverbal communication, and sensory functions like sight and smell, according to one embodiment. Facial recognition, whether by humans or technology, may be a complex process that involves interpreting the unique combination of features and expressions to identify or understand the emotional state of an individual, according to one embodiment.

The face 1710 may be associated with a visual inference database 1718 and/or a government database 1714, according to one embodiment. The visual inference database 1718 may be used to fine tune an identity artificial intelligence model 1722, according to one embodiment. The identity artificial intelligence model 1722 may also utilize government data 1714, and may be periodically built and updated from the government database 1714, according to one embodiment.

Figure 18:
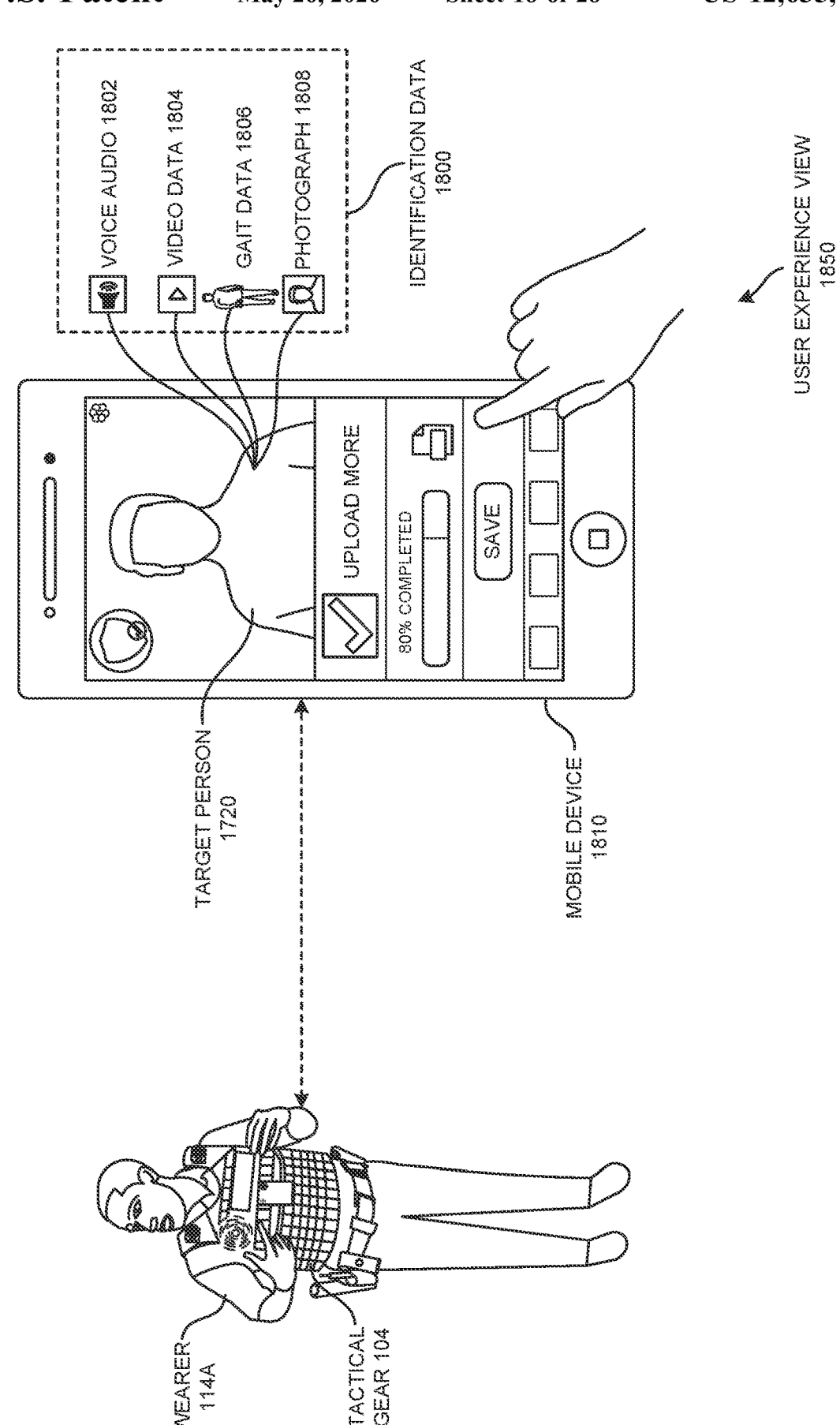
FIG. 18 is a user experience view depicting that identifying data of the target person is uploaded to a mobile application paired with the tactical vest, according to one embodiment.

FIG. 18 is a user experience view 1850 depicting that identifying data of the target person 1720 is uploaded to a mobile device 1810 paired with the tactical gear 104, according to one embodiment. In FIG. 18, a mobile device 1810 may be paired with the tactical gear 104. The function of the application on the mobile device 1810 is to take an identification data 1800 associated with a target person 1720 and fine tune the identity artificial intelligence model 1722 so that the tactical gear 104 detects the target person's face, gait, or other identifying information and causes a notification (e.g., haptic, auditory, visual) to the wearer 114 using the responsive device 106. The identification data 1800 may include voice audio 1802 associated with the target person 1720, a video data 1804 associated with the target person 1720, a gait data 1806 associated with the target person, and a photographic data 1808 associated with the target person 1720.

The wearer 114 may have a voice audio 1802, a video data 1804, a gait data 1806, and or a photograph 1808 of the target individual 1720, according to one embodiment. This photo may be shown to a visual sensor 102 integrated into the tactical gear 104 or uploaded through a mobile app on the mobile device 1810 that's wirelessly paired with the tactical gear 104, according to one embodiment. This process may be quick and can be done in the field with minimal setup time, according to one embodiment.

Image Processing and Database Matching: Upon receiving the identification data 1800, the system may use advanced image recognition algorithms to analyze the identification data 1800 and extract key features and/or characteristics of the target person's 1720 appearance, according to one embodiment. This may create a digital signature or profile that can be used for immediate recognition, according to one embodiment.

If available and necessary, the system may cross-reference this digital signature with the government database 1714 to retrieve additional information or confirm the identity of the target person 1720, according to one embodiment. However, this step is optional and depends on the operation's requirements, according to one embodiment. With the target person's 1720 digital signature now loaded into the system, the tactical gear 104 integrated visual sensors 102 may continuously scan the environment for a match, according to one embodiment. This scanning process may be discreet and does not interfere with the wearer 114's mobility or other functions, according to one embodiment. Once the system identifies the target person 1720 based on the uploaded identification data 1800, it may immediately alert the wearer 114, according to one embodiment. This alert may be delivered through various means tailored to the operation's needs and the wearer 114's preference, according to one embodiment. A vibration alert on the tactical gear 104 may indicate a match, with different patterns specifying details like the target's proximity, according to one embodiment. Earpiece communication may provide a verbal alert that the target has been spotted, possibly including direction or distance, according to one embodiment.

For systems equipped with HUDs or connected mobile devices, a visual alert may pop up, showing the target person's 1720 location relative to the wearer 114 or even a live feed highlight, according to one embodiment. Upon receiving the alert, the wearer 114 may take appropriate action, which can range from approaching the target for confrontation, surveillance, or capturing, depending on the mission parameters, according to one embodiment. The system may allow the wearer 114 to remain discrete and adaptable, enabling a response that's calibrated to the fluid dynamics of field operations, according to one embodiment. By simplifying the input process to showing an identification data 1800 and uploading it via an app, the system may be made user-friendly and accessible, even under stressful conditions, according to one embodiment. The ability to quickly identify target person 1720 in real-time without manual searches or extensive pre-operation setups may significantly enhance operational efficiency, according to one embodiment.

Identifying a target person 1720 using AI and computer vision technologies may involve analyzing various forms of data, including voice audio 1802, video data 1804, and gait data 1806, to fine-tune identity artificial intelligence model 1722, according to one embodiment. These technologies may significantly enhance the ability of personal protective equipment 100, such as the tactical gear 104, to recognize a target person 1720 and alert the wearer 114 through different types of notifications, according to one embodiment. Voice audio data 1802 may be utilized by the identity artificial intelligence model 1722 to recognize a target person's 1720 unique vocal characteristics. Each person's voice has distinct features such as pitch, tone, and rhythm, which may be captured in voice audio samples. By analyzing these features, the identity artificial intelligence model 1722 may be trained to identify the target person 1720 based on their voice, even in noisy environments. This may be particularly useful in situations where visual identification is not possible, according to one embodiment Video data 1804 may provide a rich source of information for identity artificial intelligence model 1722 to identify a target person 1720. These models may analyze facial features, body shape, and movements to recognize individuals. Video data 1804 may allow for the extraction of dynamic facial expressions and subtle body movements, enabling a more accurate and robust identification process compared to static images, according to one embodiment. The identity artificial intelligence model 1722 may be trained on video data to learn the distinctive attributes of a target person's 1720 appearance and behavior, improving the accuracy of real-time identification in various environments, according to one embodiment.

Gait data 1806 may refer to the pattern of movement of an individual while walking or moving, according to one embodiment. Each person has a unique gait, which can be analyzed to identify them from a distance or when their face is not visible, according to one embodiment. Gait analysis may involve training the identity artificial intelligence model 1722 on body mechanics, including stride length, speed, and limb movement patterns, according to one embodiment. The identity artificial intelligence model 1722 may use gait data to create a signature profile for a target person 1720, allowing for their identification based on how they walk or move.

Integrating voice, video, and gait data into an AI-enhanced visual identity model may enable a comprehensive approach to identifying a target person 1720, according to one embodiment. The application on a mobile device 1810 may take this identification data 1800 associated with a target person 1720 and fine-tune the AI model (e.g., using AI model 1574 of the data pipeline 1504), according to one embodiment. This refined model may then be integrated into personal protective equipment 100 including the tactical gear 104, according to one embodiment.

Figure 19:
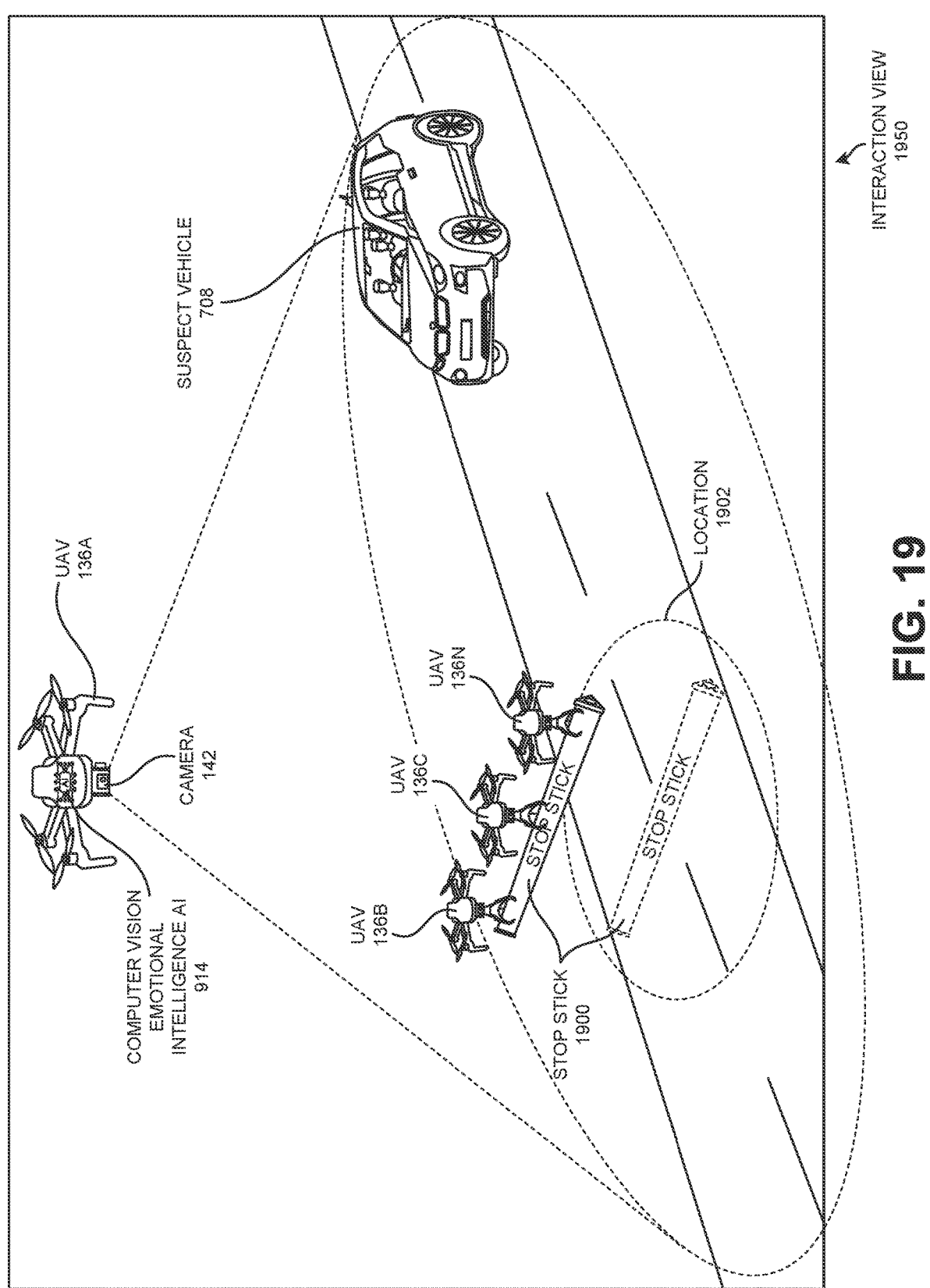
FIG. 19 is an interaction view depicting unmanned aerial vehicles placing stop sticks ahead of a suspect vehicle arriving at a location, according to one embodiment.

FIG. 19 is an interaction view 1950 depicting unmanned aerial vehicles 136A-N placing a stop stick 1900 ahead of a suspect vehicle 708 arriving at a location 1902, according to one embodiment. Multiple unmanned aerial vehicles 136A-N might be needed to place the stop stick 1900 well in advance of a suspect vehicle 708 arriving at a location where the stop stick 1900 is placed, according to one embodiment.

In the innovative approach to safely concluding high-speed pursuits, a novel embodiment of FIG. 19 incorporates the use of a deployable stop stick 1900 that may be remotely activated and positioned by unmanned aerial vehicle 136B-N or integrated systems within tactical gear 104, according to one embodiment. In one embodiment, as illustrated in FIG. 19, UAV 136A may keep a watchful eye on the suspect vehicle 708 from the air and suggest course correction is needed to a location 1902 where the stop stick 1900 is to be placed, according to one embodiment. This system may be designed to minimize the risks associated with vehicle pursuits, protecting both law enforcement personnel and the general public, according to one embodiment. Utilizing drones carrying a deployable stop stick 1900, law enforcement may end suspect vehicle 708 pursuits by strategically placing stop sticks 1900 in the path of the fleeing suspect vehicle 708, according to one embodiment. These unmanned aerial vehicles 136B-N may be remotely controlled from a command center 302 and/or by officers using tactical gear 104, allowing for precise placement without putting officers in harm's way, according to one embodiment.

The UAVs 136 may be equipped with advanced navigation and real-time video transmission capabilities, enabling operators to identify the optimal location for deploying the deployable stop stick 1900 based on the suspect vehicle 708 trajectory and traffic conditions, according to one embodiment. Officers equipped with a patrol vehicle 700 touchscreen display 604 may remotely activate the deployable stop stick 1900 that are pre-positioned along potential pursuit routes, according to one embodiment. This system may rely on a network of concealed unmanned aerial vehicle 136 that can be activated individually or in groups, depending on the situation, according to one embodiment. The display in the patrol vehicle 700 and/or command headquarters 302 may include a control interface that allows officers to select the most appropriate deployment site based on real-time data, including GPS tracking of the fleeing vehicle, traffic patterns, and road conditions, according to one embodiment.

By allowing law enforcement to deploy the deployable stop stick 1900 remotely, either through drones or a networked system, the risks associated with manually placing stop sticks in the path of high-speed vehicles may be significantly reduced, according to one embodiment. The ability to precisely place or activate the deployable stop stick 1900 in real-time may increase the likelihood of safely ending pursuits quickly, minimizing the potential for accidents or collateral damage, according to one embodiment. The system may offer multiple deployment options, catering to different operational scenarios and requirements, according to one embodiment. It may be adapted to urban environments, highways, or rural settings, according to one embodiment.

Effective use of this technology may require comprehensive training for operators, focusing on operational safety, decision-making, and familiarity with the control systems, according to one embodiment. Clear protocols must be established to guide the deployment of the deployable stop stick 1900 in various pursuit scenarios, according to one embodiment. The deployment of the deployable stop stick 1900, especially via unmanned aerial vehicle 136, must comply with aviation and public safety regulations, according to one embodiment. Coordination with regulatory bodies may be essential to ensure the lawful and safe use of this technology, according to one embodiment. Public awareness campaigns may be necessary to inform the community about the use of this technology, emphasizing its role in enhancing public safety and reducing the risks associated with high-speed pursuits, according to one embodiment.

By integrating deployable stop stick 1900 into law enforcement operations through unmanned aerial vehicle 136 and tactical gear 104, this embodiment represents a significant advancement in pursuit management tactics, according to one embodiment. It combines innovation with practicality, offering a safer, more controlled method of ending vehicle pursuits and protecting both officers and civilians, according to one embodiment. An embodiment designed to enhance operational control and safety during critical incidents may incorporate a system for the denial of communications, specifically targeting the ability to jam cell phone or radio signals, according to one embodiment. This technology may be crucial for preventing suspect 800 from communicating with accomplices or remotely detonating explosive devices, according to one embodiment. The system may be integrated into tactical operations through wearable gear or deployable units, offering flexibility and precision in usage, according to one embodiment.

In addition to saving video footage, the personal protective equipment 100 may also store a descriptive AI log file 1110 detailing the events leading up to the triggered response, according to one embodiment. This log file 1110 may provide valuable context for understanding why the alert was activated, according to one embodiment. Furthermore, this embodiment may permit live streaming from one or more visual sensors 102 on the tactical gear 104, according to one embodiment. The live streaming functionality may be implemented using a secure streaming protocol to ensure the privacy and integrity of the transmitted data. Encryption techniques may be employed to protect the video feed from unauthorized access or interception, according to one embodiment. In addition, it will be appreciated that the various operations, processes and methods disclosed herein may be embodied in a non-transitory machine-readable medium and/or a machine-accessible medium compatible with a data processing system.

In the context of enhancing officer wellness, an innovative embodiment may integrate both drone technology and advanced wearable sensors into a system designed to operate within educational environments, according to one embodiment. This system aims to address the dual concerns of proactive threat management and the physical and mental well-being of security personnel, according to one embodiment.

Haptic Vest Integration: Building on the idea of the tactical vest (e.g., tactical gear 104), the embodiment may consider integrating the technology into an undershirt worn directly against the body. This undershirt can be made from a durable, washable material that houses sensors capable of monitoring vital signs such as heart rate, blood pressure, and indicators of dehydration, according to one embodiment.

Wellness Alerts: The sensors (e.g., biometric sensors 160) may continuously analyze the wearer's physiological data, sending alerts through haptic feedback directly to the officer and, optionally, to their supervisors, according to one embodiment. These alerts may indicate signs of extreme stress, potential health issues, or the onset of critical incident stress responses like "tunnel vision," according to one embodiment System Design Considerations Durability and Maintenance: The undershirt design may incorporate materials and electronics that are resilient to water and may withstand regular washing, ensuring the technology remains functional and hygienic for daily use, according to one embodiment.

Integration with Existing Systems: The system may be designed to work seamlessly with existing safety platforms, such as Fusus for live operational coordination and Prepared 911 for emergency communications. Integration may ensure that all components of the safety ecosystem work in concert, according to one embodiment.

Data Privacy and Security: Given the sensitive nature of the data collected, especially personal health information, the system may be engineered with robust data protection measures. This may include encrypted communications and strict access controls to ensure information is only available to authorized personnel, according to one embodiment.

Officer Wellness as a Core Component

Emphasizing officer wellness, this system acknowledges the high stress and potential health risks associated with security roles, according to one embodiment. By providing real-time monitoring and alerts for health metrics, the system may aid in preventing medical emergencies and enhancing the overall well-being of officers, according to one embodiment The technology may allow for feedback on an officer's physical condition (e.g., haptic alert based on biometric sensor 160 data), enabling adaptations to their workload or immediate interventions, such as hydration reminders or stress management techniques, to mitigate health risks, according to one embodiment. Accordingly, the specification and drawings are to be regarded in an illustrative rather than a restrictive sense.

Figure 20:
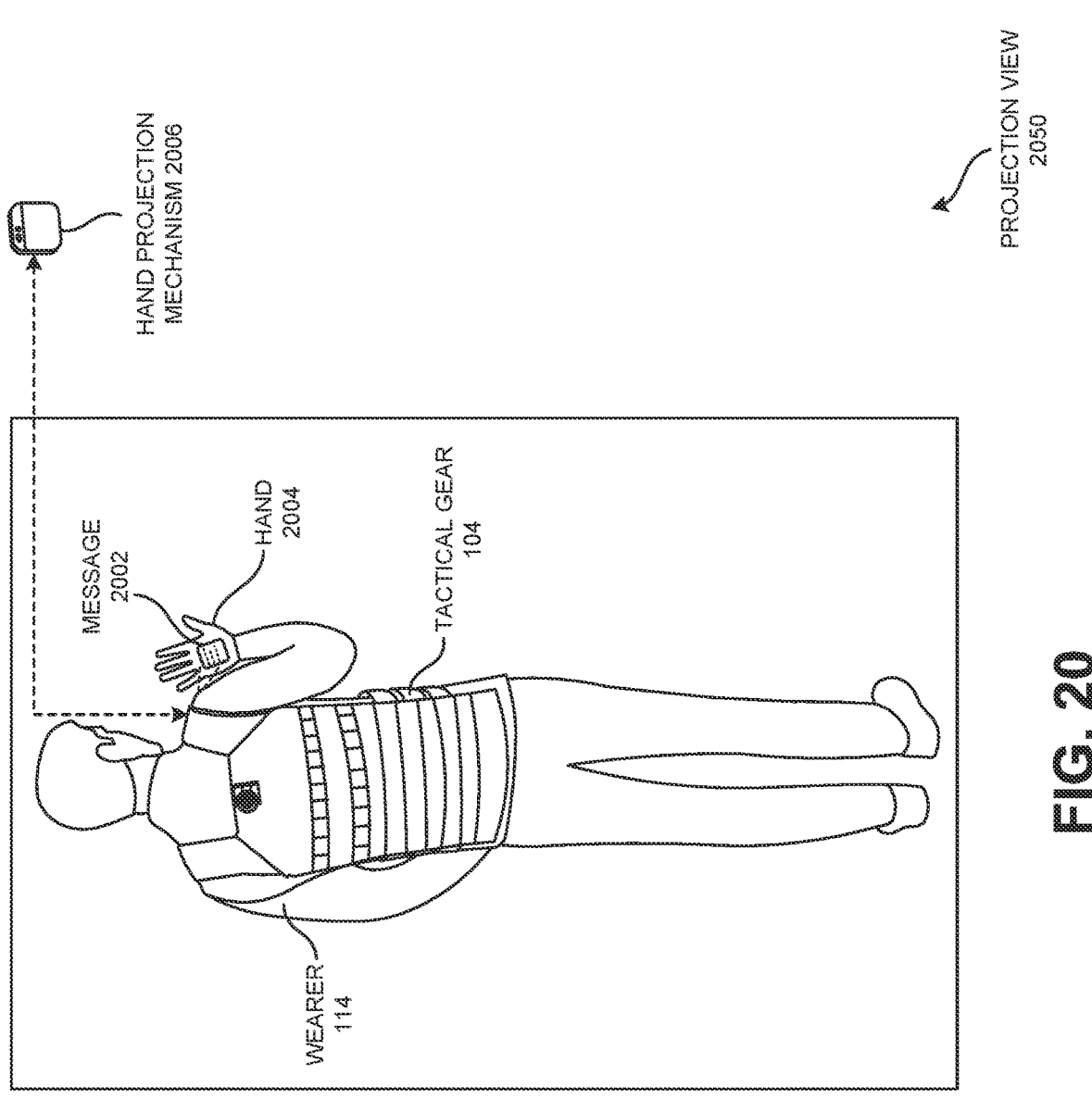
FIG. 20 is a projection view of the personal protective equipment of FIG. 1, according to one embodiment.

FIG. 20 is a projection view 2050 of the personal protective equipment 100 of FIG. 1, according to one embodiment. The personal protective equipment 100 may include a hand projection mechanism 2006 to display a message 2002 to the wearer 114. This hand projection mechanism 2006 may be a separate module on the tactical gear 104 adjacent to the drone control apparatus 124 or the language translation module 144, or integrated within these modules.

The hand projection mechanism 2006 may help the wearer 114 interact with configuration options of the tactical gear 104, convey biometric information, provide situational information, provide navigational directions, and/or reasons why the responsive device 106 was triggered without needing a monitor/display. For example, the hand projection mechanism 200 may project the wearer 114's health statistics from the biometric sensor(s) 160, like heart rate or stress levels, helping them stay aware of their physical condition during critical situations. The hand projection mechanism 2006 may project maps or directional arrows directly on the hand 2004 to guide the wearer 114 through unknown or hazardous environments. For a wearer 114 in international missions, the hand projection mechanism 2006 may project real-time translations of foreign text or speech, making communication easier.

The hand projection mechanism 2006 may be a small device that the wearer 114 may clip on the tactical gear 104. This innovative approach may allow for dynamic interaction with the compute module 118 without necessitating a conventional screen. Such a design choice may streamline user interaction and also may reduce the cognitive load on the wearer 114, allowing for seamless access to critical information and controls. The hand projection mechanism 2006 may be a wearable projection device that projects a message 2002 (e.g., reasons why a haptic response 400 occurred, navigational directions etc.) onto the hand 2004 of the wearer 114. This method of information delivery may enable the wearer 114 to quickly receive and interpret data from the tactical gear 104, including detailed explanations regarding the activation of responsive device(s) 106. The hand projection mechanism 2006 may include a vision feature that may use a camera to scan an area where the projection is made, to enable the wearer 114 to submit commands to the tactical gear 104 through gesture navigation capabilities, according to one embodiment. This feature may integrate a camera designed to monitor the projection area on the wearer's hand 2004, thereby enabling a method of input through gesture navigation. The wearer 114 can interact with their tactical gear 104, issuing commands and navigating system interfaces through simple hand gestures. This capability not only enhances the tactical gear 104's functionality but also may introduce a new level of interactivity, making the tactical gear 104 more intuitive and responsive to the wearer 114's needs.

The hand projection mechanism 2006 may incorporate a training feature that projects instructional guides or tutorials onto the hand 2004, helping new wearers 114 learn new skills or equipment functionalities on the go. The hand projection mechanism 2006 may project QR codes or digital IDs for secure access to restricted areas, ensuring only authorized personnel can enter certain locations. These enhancements can make the personal protective equipment 100 not just a tool for protection but a multifunctional device that supports the wearer in diverse scenarios, from health and navigation to learning and secure access.

Figure 21:
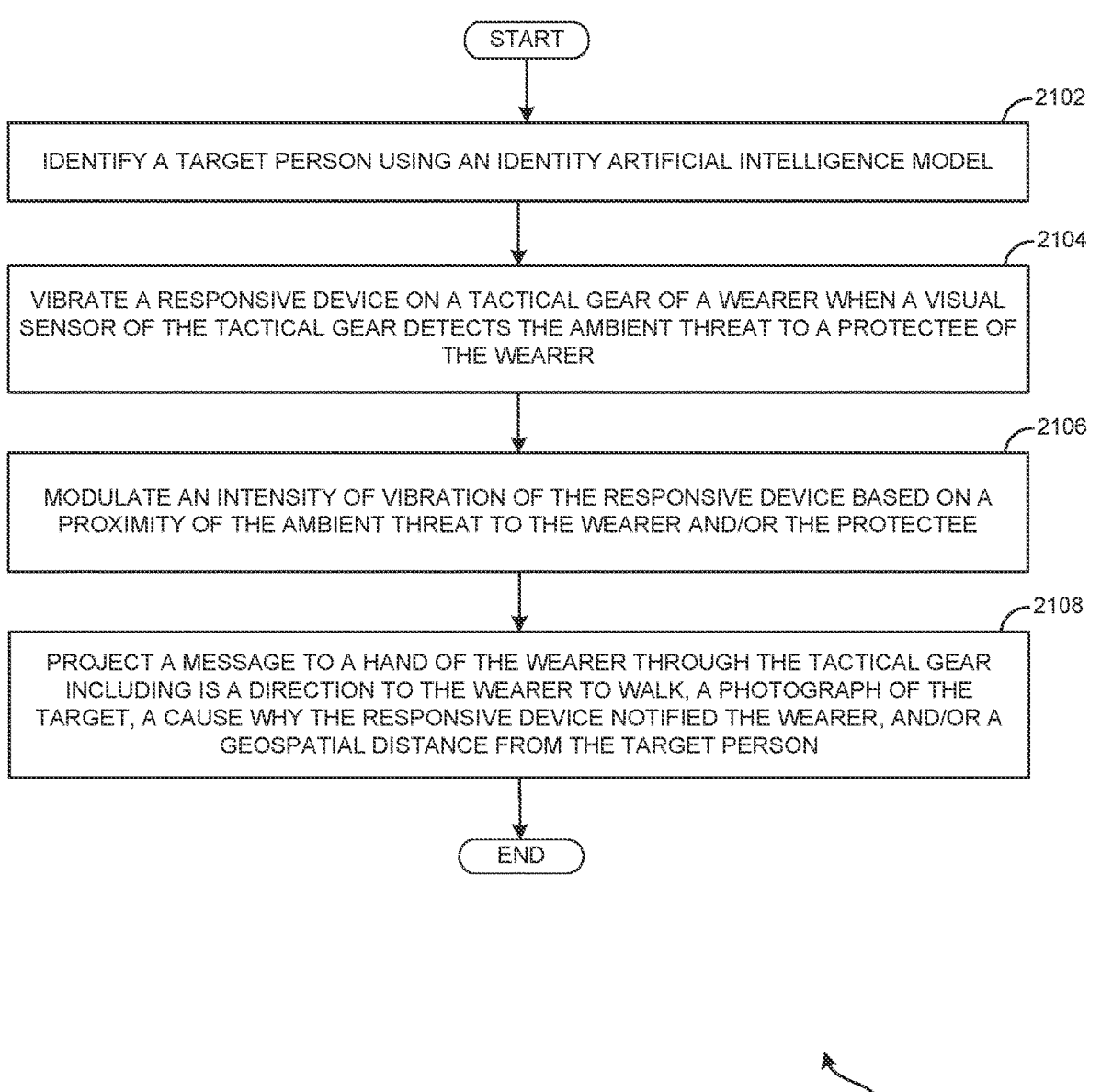
FIG. 21 is a process flow describing a series of operations of the personal protective equipment of FIG. 1 to project a message onto the hand of the wearer, according to one embodiment.

FIG. 21 is a process flow 2150 describing a series of operations of the personal protective equipment 100 of FIG. 1 to project a message 2002 onto the hand 2004 of the wearer 114, according to one embodiment. In operation 2102, the personal protective equipment 100 may identify a target person 1720 using an identity artificial intelligence model 1722.

In operation 2104, the array of haptic sensors 210 on the personal protective equipment 100 may vibrate a responsive device 106 on a tactical gear 104 of a wearer 114 when a visual sensor 102 of the tactical gear 104 detects the ambient threat 132 to a protectee 310 of the wearer 114. In operation 2106, the threat detection model 108 of the personal protective equipment 100 may modulate an intensity of vibration of the responsive device 106 based on a proximity of the ambient threat 132 to the wearer 114 and/or the protectee 310, according to one embodiment. In operation 2108, a hand projection mechanism 2006 of the personal protective equipment 100 may project a message 2002 onto a hand 2004 of the wearer 114 through the tactical gear 104. The message 2002 may include a direction to the wearer 114 to walk, a photograph 1808 of the target, a cause why the responsive device 106 notified the wearer 114, and/or a geospatial distance from the target person 1720, according to one embodiment.

FIG. 22 is a translation view 2250 illustrating a process flow of bi-directional communication with a group of individual(s) 2206 by the wearer 114 of the personal protective equipment 100 of FIG. 1. Particularly, FIG. 22 illustrates the communication with a group of individuals 2206 in an ambient environment 2200 using any other language 2202 other than a primary language 2208 spoken by the wearer 114 when the language translator module 144 is activated by the wearer 114. As shown in circle "1", two individual(s) 2206 may speak in other languages 2202 with the wearer 114 in an ambient environment 2200. As the other language 2202 is not understood by the wearer 114, it may activate the language translator module 144 using the activate button 2204 on the tactical gear 104 he or she is wearing. In circle "2" of FIG. 22, upon activation, the language translator module 144 may listen to the other language 2202 spoken by the individual(s) 2206 and translates it to the primary language 2208 of the wearer 114. In circle "3", the language translator module 144 may listen to the primary language 2208 and translate it to the other language 2202 enabling a bidirectional communication between the wearer 114 and the individual(s) 2206 in the ambient environment 2200. In circle "4", while the wearer 114 is speaking with the individual(s) 2206 in mitigating the hostile situation, the object recognition module 122 of the tactical gear 104 may detect an ambient threat 132 from behind and trigger the responsive device 106 to send a haptic alert 2210 to the wearer 114 to make him/her aware of a threat approaching from its back, according to one embodiment.

FIG. 23 is a medical emergency view 2350 illustrating a biometric sensor 160 on a back side of the language translator module 144, and touching the skin of the wearer 114, and wherein the entire assembly is detachable and attachable to a wrist of an injured person 2300 through a hidden armband 2304 to communicate biometric information 2306 to a hospital 2308, according to one embodiment.

FIG. 23 depicts a multifunctional device that serves both as a language translator module 144 and a biometric sensor 160, used in medical emergencies. This device is illustrated in three sequential use-case scenarios. In circle "1", the device may be a biometric sensor 160 integrated with a language translator module 144 worn by a medical professional and/or a first responder. The biometric sensor 160 may be located on the backside of the language translator module 144, allowing it to make contact with the skin of the wearer 114 and monitor vital signs and/or other biometric data, according to one embodiment. This device may be a wrist-worn gadget in an alternative embodiment.

The device may have a detachable and reconfigurable design. The device may be detachable from the wearer 114. Once removed, it may reveal hidden straps that allow it to be transformed into a standalone biometric reader. This reader may then be attached to the wrist of an injured person 2300 using the armband 2304, as shown in circle "2", according to one embodiment.

After attaching the device to the injured person's wrist, the biometric sensor 160 may start collecting health data of the injured person 2300. This biometric information 2306 may then be wirelessly communicated to a hospital 2308 and/or other medical facility, as shown in circle "3". The hospital 2308, upon receiving this data, may get alerts and may monitor the injured person's condition en route to the facility, according to one embodiment.

This system may be designed to provide real-time health monitoring of the injured person 2300 from the point of injury to the hospital 2308, improving the ability to begin assessment and preparation for treatment before the patient arrives. The dual functionality as a language translator may also be used to communicate with the injured person 2300 and/or responders who speak different languages, further aiding in the emergency response process, according to one embodiment.

Figure 24:
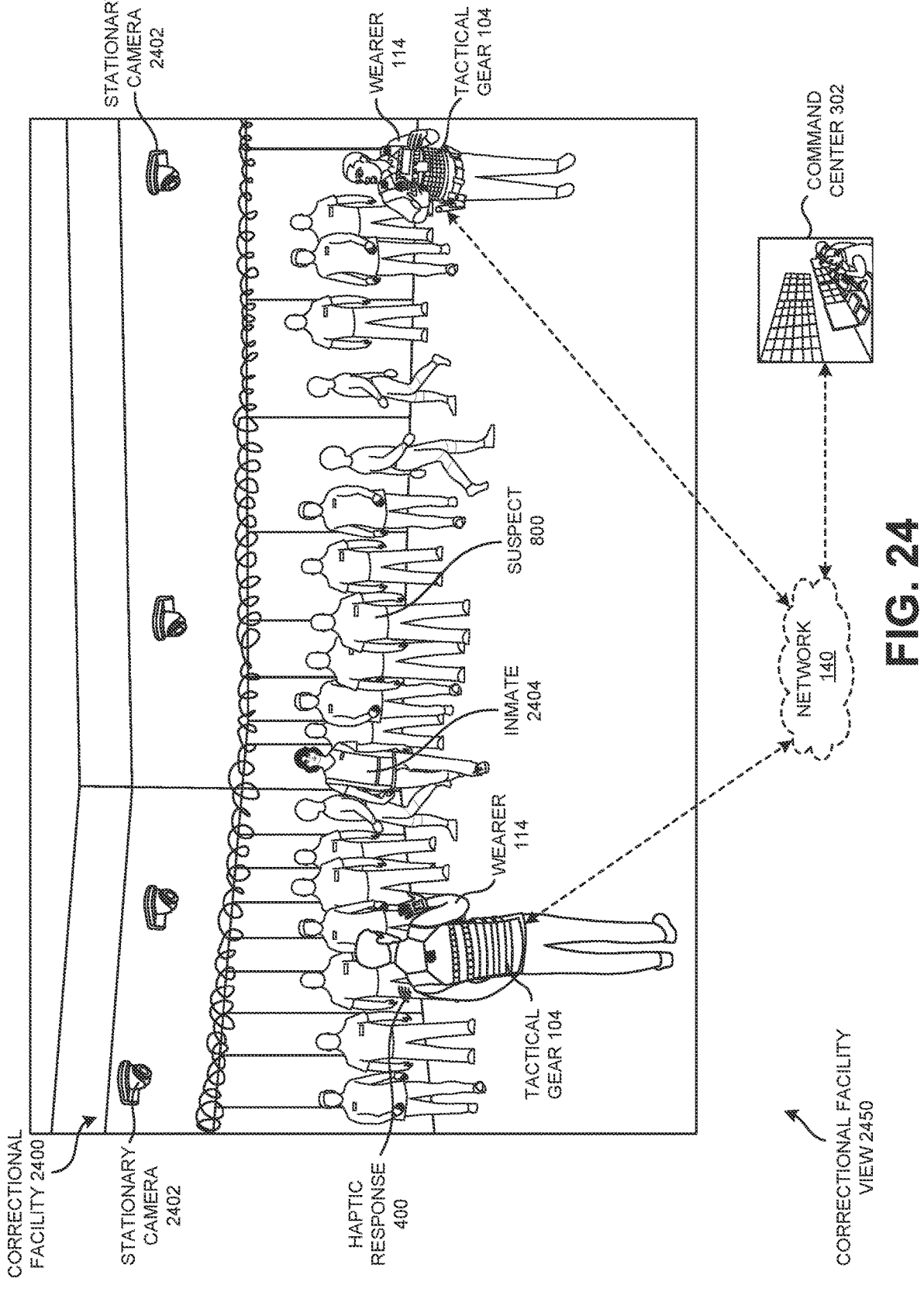
FIG. 24 is a correctional facility view illustrating a responsive device of the personal protective equipment of FIG. 1 to notify a wearer of the tactical gear when the visual sensor identifies an ambient threat to the wearer and/or the inmate of the correctional facility, according to one embodiment.

FIG. 24 is a correctional facility view 2450 illustrating a responsive device 106 of the personal protective equipment 100 of FIG. 1 to notify a wearer 114 of the tactical gear 104 when the visual sensor 102 identifies an ambient threat 132 to the wearer 114 and/or the inmate 2404 of the correctional facility 2400, according to one embodiment.

The advanced security system of the personal protective equipment 100 described in FIG. 24 may operate through a combination of hardware (e.g., the tactical gear 104 with integrated visual sensors 102) and software (the inmate artificial intelligence model). The tactical gear 104 equipped with visual sensors 102 such as stationary cameras 2402 and/or other image-capturing devices may be capable of continuous environmental monitoring. The system may include an identity artificial intelligence model 1722 trained specifically to recognize the inmates 2404. This model may be trained on a database of inmate images and/or movement patterns and may differentiate between inmates and other individuals within the correctional facility 2400. The identity artificial intelligence model 1722 may process the input from the visual sensors 102 in real time. The identity artificial intelligence model 1722 may constantly scan the environment for anomalies or behavior that deviates from a predefined norm, which may indicate potential ambient threat(s) 132. These threats may range from unauthorized individuals (e.g., suspect 800) entering a restricted area, to unexpected gatherings of inmates 2404 that may precede a conflict, to detecting prohibited items in the possession of an inmate 2404 or others, according to one embodiment.

Upon detecting a potential ambient threat 132 and/or recognizing an inmate 2404 acting suspiciously (e.g., as defined by the AI model's parameters), the system may trigger a haptic response 400. This alert is sent to the tactical gear's wearer 114 via the integrated communication network 140. The tactical gear 104 may use haptic feedback systems (e.g., vibrations) to notify the wearer 114 without relying on visual or audio cues, which might not be effective in a loud or visually obstructive environment. Upon receiving the notification, the wearer 114 (e.g., a security officer) may assess the situation and decide on the best course of action. The prompt notification may allow for a rapid response, potentially defusing a situation before it escalates. The system may also record the detected incident for future review, both for legal purposes and to train the AI model to improve its accuracy over time. In essence, the described system may create an integrated security network that enhances situational awareness and response capabilities within a correctional facility 2400 by combining AI-driven analysis with responsive tactical gear 104, according to one embodiment.

GovGPT™ Zebra, a cutting-edge Real-Time Corrections Management Platform designed specifically for the operational needs of jails and prisons (e.g., correctional facility 2400 using the personal protective equipment 100). At the heart of GovGPT™ Zebra is Cluster, a cloud-based solution that may integrate seamlessly with the correctional facility 2400, providing a unified, real-time monitoring and management interface (e.g., using real time data 1112 of the user interface view 1150). This platform may revolutionize the way correctional officers (e.g., wearer 114 of the tactical gear 104), supervisors, and administrators oversee facilities, enhancing security, efficiency, and decision-making capabilities, according to one embodiment.

GovGPT™ Zebra Cluster may transform the approach to surveillance within correctional facilities 2400 by offering real-time monitoring of every internal and external video camera (e.g., using the stationary camera 2402). This feature may ensure that legacy systems and the latest camera technologies are all viewable under a single digital roof (e.g., command center display 604B of the command center 302). Video feeds may be organized on a digital floor plan, allowing for immediate visual access (e.g., using the real-time data 1112 and the AI video analysis 1130 in the display 604 of the user interface view 1150) to any area within the correctional facility 2400. Moreover, the real-time tracking of correctional personnel through these digital maps (e.g., threat maps 1134) using the maps and GPS data 1108 may enhance the safety and operational efficiency of staff as they navigate through various sectors of the correctional facility 2400, according to one embodiment.

GovGPT™ Zebra Cluster's alerting system may be designed to keep supervisors (e.g., wearer 114 of the tactical gear 104) informed of critical incidents instantly, no matter their location. This may include panic alerts (e.g., haptic alert 2210), unauthorized drone activities, fire alarms, and/or access control breaches. The platform may also integrate the geolocations of response teams (e.g., patrol vehicle 700, armored carrier 134, command center 302, wearer 114, different wearer 114B, UAV 136, and drone system 150, etc.), enabling a swift and coordinated response to any situation, thereby significantly reducing reaction times and increasing the effectiveness of emergency protocols, according to one embodiment.

Embedded within GovGPT™ Zebra Cluster may be a powerful AI assistant that serves as a force multiplier for the correctional staff (e.g., wearer 114 of the tactical gear 104). This technology may provide automatic real-time detection of contraband distribution, preemptive threat identification (e.g., using the threat detection model 108 of the personal protective equipment 100), and the pinpointing of safety risks before they escalate into incidents. As described in various embodiments of FIGS. 1-28, the AI capabilities may be backed by a customizable rules-based engine, allowing facilities to tailor the system to meet their specific operational requirements and/or security protocols, according to one embodiment.

As described in various embodiments, GovGPT™ Zebra Cluster may facilitate improved communication and coordination among staff by providing a comprehensive overview of staff locations (e.g., using GPS module 116 of the personal protective equipment 100) and incident alerts in real-time. This may help ensure that communication gaps are minimized. This feature may be crucial for the effective management of inmate populations (e.g., inmate 2404) and the quick mobilization of response teams during emergencies, according to one embodiment.

GovGPT™ Zebra Cluster may offer a single view for the comprehensive monitoring and management of all surveillance and operational data (e.g., using the realtime data 1112 captured by the UAV 136A and visual sensor 102 of the tactical gear 104), according to one embodiment. In another embodiment, instant access to live video feeds (e.g., using the video data 1804 captured by the UAV 136A and visual sensor 102 of the tactical gear 104), and personnel locations (e.g., GPS data) may allow for informed decision-making in critical situations, according to one embodiment.

AI-driven insights and real-time alerts (e.g., using generative meaningful insights for ambient threat detection 1646 of the personal protective equipment 100 with an integrated AI-powered ambient threat detection model 108) may significantly improve the correctional facility's ability to preempt and respond to security threats, according to one embodiment. With its cloud-based architecture, Cluster may be scalable to accommodate the growing needs of facilities without requiring significant additional investment in hardware, according to one embodiment.

GovGPT™ Zebra may work with the tactical gear 104 system to enhance the safety and operational efficiency of correctional facilities 2400. This integrated solution may address the challenges faced by jails and prisons, including physical assaults, the smuggling of contraband, gang dominance, radicalization, drug trafficking, and health crises, among others, according to one embodiment.

GovGPT™ Zebra's AI-driven platform may process live video feeds from stationary cameras 2402 installed throughout the correctional facility 2400, including sensors integrated on the tactical gear 104 of correctional officers (e.g., wearer 114). This system may use advanced algorithms (e.g., identity artificial intelligence model 1722, facial recognition algorithm 1704, etc. of the government database 1714) to detect unusual activities, potential threats, or suspicious behavior among inmates 2404, according to one embodiment.

Upon detecting a potential threat, the system may communicate in real-time with the wearable tactical gear 104 of nearby correctional officers (e.g., wearer 114). The gear, equipped with haptic technology (e.g., haptic alert 2210), may vibrate to alert other correctional officers to the nature and direction of the threat. This immediate, tactile feedback may enable correctional officers to respond swiftly, even if they are not looking at a monitor, according to one embodiment. For example, the AI may analyze patterns of movement and behavior to identify situations that can escalate into confrontations, fights, or other forms of violence. It may take into account factors like group formations that may indicate gang activity, rapid movements typical of physical altercations, or the hand-off movements associated with contraband smuggling, according to one embodiment.

Recognizing that new inmates 2404 or those under significant stress may be likely to be involved in incidents, the tactical gear 104 in a correctional facility 2400 may monitor signs of agitation or distress. This may include pacing, erratic movements, or aggressive interactions with others thereby allowing for early intervention, according to one embodiment. Specialized algorithms and sensors on the tactical gear 104 in a correctional facility 2400 may be trained to detect the smuggling of drugs and other contraband, whether through personal interactions, deliveries, and/or drones. The personal protective equipment 100 system may alert officers (e.g., wearer 114) to suspicious exchanges or unauthorized drone activity near the facility, according to one embodiment.

Beyond security threats, the system may also monitor indicators of health crises (e.g., using biometric sensor 160 of the personal protective equipment 100), such as an inmate 2404 collapsing, which may signify an overdose, a mental health episode, or a chronic health condition worsening, as described in various embodiments of FIGS. 1-28, according to one embodiment. Quick, haptic alerts 2210 may enable officers to intervene before confrontations escalates, reducing the incidence of serious fights and lethal violence, according to one embodiment.

By identifying and monitoring (e.g., using the stationary camera 2402 of the correctional facility 2400) known gang members or individuals (e.g., suspect 800 or inmate 2404) showing signs of radicalization, the system may allow for targeted interventions and monitoring, potentially preventing the exertion of undue influence over the general inmate population, according to one embodiment. Real-time alerts (e.g., haptic alerts 2210), to suspicious behavior may help in intercepting contraband before it circulates within the correctional facility 2400, tackling issues from drug trafficking to the spread of diseases through shared needles, according to one embodiment. The system may enhance perimeter security by detecting attempts to breach security, alerting (e.g., using haptic alerts 2210) officers wearing tactical gear 104 immediately to potential escape efforts, according to one embodiment. By detecting behaviors indicative of mental health crises, the system may enable timely intervention by trained professionals, addressing the urgent need for psychiatric care and preventing self-harm or harm to others, according to one embodiment. The haptic feedback system (e.g., haptic response 400 to the wearer 114) may enhance officer safety by providing immediate alerts to threats, reducing the reliance on constant visual monitoring and potentially lowering stress levels by offering tangible (e.g., as described in haptic table 1050 of FIG. 10), actionable intelligence, according to one embodiment.

This integrated approach, combining GovGPT™ Zebra's AI capabilities with Cluster's real-time communication and the use of wearable haptic technology of the tactical gear 104, represents a significant leap forward in maintaining safety, security, and health within correctional facilities 2400. It may provide a proactive, rather than reactive, framework for managing the complex challenges inherent in the correctional environment, according to one embodiment.

GovGPT™ Zebra's AI algorithms may be trained to recognize the distinct shapes and packaging of tobacco products. When cameras (e.g., body worn camera 216 of the tactical gear 104, stationary camera 2402) capture images or movements (e.g., image/video capture 1712) suggesting the exchange of such items, the system may alert officers via haptic feedback (e.g., haptic response 400 to the wearer 114), according to one embodiment. Advanced sensors (e.g., array of visual sensors 200, responsive device 106, etc.) may detect the unique chemical signature of tobacco smoke, triggering alerts for unauthorized smoking areas, according to one embodiment.

The tactical gear 104 may incorporate chemical sensors (e.g., using responsive device 106) into the facility's infrastructure and officers' tactical gear 104 to detect the specific odors or vapors of various drugs and homemade alcohol, according to one embodiment. GovGPT™ Zebra's AI model (e.g., using object recognition module 122, compute module 118, etc.) of the tactical gear 104 may monitor for behaviors consistent with drug use or intoxication, such as unusual coordination, agitation, or drowsiness, and alerts staff to investigate, according to one embodiment. The tactical gear 104 may employ technology (e.g., thermal sensor 916) to detect unauthorized cell signals. When a mobile phone is used, the system may triangulate its location and send a direct alert to nearby officers (e.g., wearer 114), according to one embodiment. The system may train AI (e.g., identity artificial intelligence model 1722) to recognize the visual signatures (e.g., using thermal sensor 916, thermal scanner 312, etc.) of mobile phones, even when partially obscured, according to one embodiment. The system may integrate portable metal detectors with the tactical gear 104, allowing officers to receive immediate haptic alerts 2210 when in proximity to metal objects that may be weapons, according to one embodiment.

GovGPT™ Zebra's AI may be trained to identify objects (e.g., using object recognition module 122 of the tactical gear 104) with shapes characteristic of knives, shivs, or other improvised weapons (e.g., using ambient threat 132), according to one embodiment. Embedding RFID tags (e.g., using the identity artificial intelligence model 1722) in permissible currency or items used as currency within the prison may help track their movement inside the correctional facility 2400. Unusual aggregations of these items may signal potential contraband activity, according to one embodiment.

GovGPT™ Zebra's AI analysis of social interactions and transactions among inmates 2404, may identify patterns that suggest the exchange of valuable items, according to one embodiment. The system may deploy natural language processing (NLP) algorithms (e.g., using the language translator module 144) to monitor and analyze inmate 2404 communications for exchanges of sensitive information, within legal and ethical boundaries, according to one embodiment. GovGPT™ Zebra's AI system of the personal protective equipment 100 system may detect and flag unusual meetings or interactions that may indicate the transfer of information, according to one embodiment.

The personal protective equipment 100 system may utilize AI to recognize specific shapes, colors, and markings of prescription pills (e.g., using the object recognition module 122), alerting staff (e.g., wearer 114) when these are identified outside of controlled distribution points, according to one embodiment. The personal protective equipment 100 system may utilize AI to monitor and analyze medication dispensing patterns for irregularities that suggest diversion or hoarding, according to one embodiment. The AI system within the personal protective equipment 100 may use electronic inventory tags on clothing and bedding items. Anomalies in their location or quantity may trigger alerts (e.g., haptic alert 2210), according to one embodiment.

The AI system within the personal protective equipment 100 may catalog and recognize issued clothing and bedding. Any item not matching the catalog may alert officers (e.g., wearer 114) of potential contraband, according to one embodiment. In addition, the AI system within the personal protective equipment 100 may employ spectral imaging to identify food items based on their unique spectral signatures, distinguishing between allowed and contraband items, according to one embodiment.

The personal protective equipment 100 system may train AI to recognize the packaging of outside food items, which are often distinct from prison-issued provisions, according to one embodiment. Also, the AI system within the personal protective equipment 100 may implement to ensure that all permissible entertainment items are logged. The AI system may monitor for any unregistered items through visual recognition, according to one embodiment. The AI system within the personal protective equipment 100 may deploy audio monitoring to detect the sounds of unauthorized electronic devices, guiding officers (e.g., wearer 114) to their locations, according to one embodiment. Each of these approaches leverages the synergy between AI-driven surveillance and the tactile immediacy of haptic feedback, enabling correctional officers (e.g., wearer 114 of the personal protective equipment 100) to respond swiftly and accurately to contraband-related threats. This multifaceted strategy may not only enhance the security and safety of the correctional facility 2400 but also significantly reduce the influx and circulation of contraband items, according to one embodiment.

FIG. 25 is a table view 2550 illustrating haptic response 400 associated with the array of haptic sensors 210 on the tactical gear 104 of FIG. 1 generating a different haptic feedback pattern 2604 for each type of detected contraband 2500 in a correctional facility 2400, according to one embodiment.

A chart of different haptic responses 400 for each type of detected contraband may help correctional officers (e.g., wearer 114 of the personal protective equipment 100) quickly discern the nature of the alert without needing to refer to a visual display 604, according to one embodiment.

Detection of tobacco and cigarettes 2502 contraband may generate a corresponding haptic feedback pattern 2604 of a single long vibration which may be a single, sustained vibration signals the detection of tobacco products, distinguishing it from more immediate threats, according to one embodiment.

Detection of drugs and alcohol 2504 contraband may generate a corresponding haptic feedback pattern 2604 of a rapid, short bursts which may be a series of quick vibrations indicates the potential presence of drugs or alcohol, requiring immediate attention due to their high contraband value and danger, according to one embodiment.

Detection of mobile phones 2506 contraband may generate a corresponding haptic feedback pattern 2604 of two long vibrations which may be two consecutive long vibrations alert to the detection of an unauthorized mobile phone, suggesting covert communication attempts, according to one embodiment.

Detection of weapons 2508 contraband may generate a corresponding haptic feedback pattern 2604 of a continuous rapid pulsing which may be a fast, pulsating vibration warns of the most immediate physical threat, suggesting the presence of a weapon, according to one embodiment.

Detection of money and currency 2510 contraband may generate a corresponding haptic feedback pattern 2604 of a triple short vibration which may take form as three short vibrations indicate the movement or exchange of money or items used as currency, potentially for contraband transactions, according to one embodiment.

Detection of information 2512 contraband may generate a corresponding haptic feedback pattern 2604 of single vibration followed by two short bursts which make take form as a unique pattern that signifies the potential exchange of information, necessitating further investigation for context, according to one embodiment.

Detection of medications 2514 contraband may generate a corresponding haptic feedback pattern 2604 of four short vibrations which may take form as four quick vibrations alert officers to the unauthorized handling or distribution of medications, which may indicate misuse or trading, according to one embodiment.

Detection of clothing and bedding 2516 contraband may generate a corresponding haptic feedback pattern 2604 of long vibration followed by a short burst which may take form as a pattern indicating non-standard clothing or bedding, which may signal unauthorized possession or status symbols within the inmate population, according to one embodiment.

Detection of food and snacks 2518 contraband may generate a corresponding haptic feedback pattern 2604 of two vibrations followed by a long burst. In addition, the system may alert to the smuggling or unauthorized exchange of food items, potentially indicating trade or reward systems among inmates, according to one embodiment.

Detection of entertainment 2520 contraband may generate a corresponding haptic feedback pattern 2604 of five short vibrations which may be a series of five short vibrations signals the presence of unauthorized entertainment items, which can be used for as weapons, as a communication mode, or for unauthorized leisure activities for inmates who are there to serve a sentence and time in restitution for their crimes, according to one embodiment.

FIG. 25 chart may provide a standardized system where each pattern of haptic feedback may correspond to a specific category of contraband. By familiarizing themselves with these patterns, officers may quickly and intuitively understand the nature of the alert without diverting their attention from their surroundings, thus enhancing their ability to respond effectively and maintain safety within the correctional facility 2400, according to one embodiment.

FIG. 26 is a haptic table view 2650 associated with the array of haptic sensors on the tactical gear 100 of FIG. 1 to generate different haptic patterns 2604, for each type of behaviors displayed by gang members 2602 detected, on the wearer 114, according to one embodiment. A system of haptic responses 400 that may differentiate between various types of threats and conditions in a correctional facility 2400 may allow corrections officers (e.g., wearer 114) to react swiftly and appropriately. Here is how different haptic feedback patterns 2604 maybe assigned to the types of detected threats and conditions listed, according to one embodiment:

Communication through symbols 2606 behaviors displayed by gang members 2602 may generate a series of short, quick vibrations to alert officers to covert communications, according to one embodiment. Formation of cliques 2608 behaviors displayed by gang members 2602 may generate two long vibrations, indicating the gathering of groups, according to one embodiment. Recruitment 2610 behaviors displayed by gang members 2602 may generate a pattern of one long vibration followed by two short ones, signaling recruitment efforts, according to one embodiment. Territoriality 2612 behaviors displayed by gang members 2602 may generate a continuous vibration for a few seconds, denoting territorial disputes, according to one embodiment.

Engagement in contraband trade 2614 behaviors displayed by gang members 2602 may generate a rapid, intermittent bursts of vibrations signaling illegal trade activities, according to one embodiment. Violence or threats 2616 behaviors displayed by gang members 2602 may generate a very fast, pulsating vibration indicating immediate attention is needed for violent behavior, according to one embodiment. Protection rackets 2618 behaviors displayed by gang members 2602 may generate three short vibrations followed by one long vibration, suggesting exploitation situations, according to one embodiment. Rituals 2620 behaviors displayed by gang members 2602 may generate a unique pattern of alternating long and short vibrations to signal ritualistic behavior, according to one embodiment.

Visual Cues Indicating Physical Injury:

Unexplained injuries 2622 behaviors displayed by gang members 2602 may generate a single, prolonged vibration to indicate potential hidden injuries, according to one embodiment.

Limping or difficulty moving 2624 behaviors displayed by gang members 2602 may generate two short vibrations followed by a long one, suggesting mobility issues, according to one embodiment.

Signs of self-harm 2626 behaviors displayed by gang members 2602 may generate a series of gentle, yet rapid vibrations to signal self-harm detection, according to one embodiment.

Changes in physical appearance 2628 behaviors displayed by gang members 2602 may generate an alternating patterns of short vibrations to indicate a need for health check-ups due to noticeable physical changes, according to one embodiment.

Visual and Behavioral Cues Indicating Mental Injury:

Withdrawal 2630 behaviors displayed by gang members 2602 may generate a slow, fading vibrations mimicking the act of withdrawing, signaling isolation behaviors, according to one embodiment.

Changes in behavior 2632 behaviors displayed by gang members 2602 may generate erratic vibration patterns, symbolizing unpredictable behavior changes, according to one embodiment.

Self-harm 2634 behaviors displayed by gang members 2602 may generate a distinct pattern of short, sharp vibrations indicating urgent attention to self-harming actions, according to one embodiment.

Substance abuse 2636 behaviors displayed by gang members 2602 may generate a continuous, low-intensity vibrations alerting to potential substance abuse, according to one embodiment.

Changes in communication 2638 behaviors displayed by gang members 2602 may generate a pattern of vibrations starting high and tapering off to signal shifts in communication habits, according to one embodiment.

Physical symptoms of stress 2640 behaviors displayed by gang members 2602 may generate a medium-intensity, steady pulsing vibration to indicate possible stress-related symptoms, according to one embodiment.

Each haptic feedback pattern 2604 may be designed to communicate specific information quickly and intuitively, allowing corrections officers (e.g., wearer 114) to understand the nature of the alert without needing to check a screen or device visually. This may enable them to remain attentive to their surroundings and respond more effectively to the needs of the facility and its inhabitants, according to one embodiment.

To detect the issues related to gang activities, physical injuries, and mental health concerns in correctional facilities 2400, GovGPT™ Zebra's system, along with haptic sensors integrated into correctional officers' tactical gear 104, may be utilized in the following ways, according to one embodiment:

Behaviors Displayed by Gang Members:

Communication Through Symbols 2606: AI-powered stationary cameras 2402 may be trained to recognize specific symbols, hand signs, graffiti, tattoos, or clothing patterns associated with gang affiliations. Upon detection, the system may send a haptic alert pattern 2604 to the tactical gear 104, signaling the presence of gang communication, according to one embodiment.

Formation of Cliques 2608: Behavioral analysis algorithms may identify the formation of cliques or groups, monitoring their interactions and movements closely. Unusual congregation in certain areas may trigger a distinct haptic alert, according to one embodiment.

Recruitment 2610: Machine learning models may detect patterns of interaction that are common during recruitment attempts, especially targeting isolated or vulnerable individuals, and alert officers via unique vibration patterns, according to one embodiment.

Territoriality 2612: AI may monitor and flag specific behaviors that indicate territorial claims over parts of the facility. Recognition of such patterns may be followed by an alert with a specific haptic signal, according to one embodiment.

Engagement in Contraband Trade 2614: The system may detect the exchange of items between inmates, using object recognition to identify potential contraband. A specific haptic pattern may alert officers to these exchanges, according to one embodiment.

Violence or Threats 2616: The system may identify aggressive behaviors or physical altercations and send an urgent haptic signal to officers' tactical gear, prompting an immediate response, according to one embodiment.

Protection Rackets 2618: By analyzing interactions and tracking the flow of goods and services between inmates, AI may identify patterns suggestive of protection rackets and alert staff through designated haptic feedback, according to one embodiment.

Rituals 2620: Surveillance systems may be trained to recognize the preparation or execution of gang rituals, triggering alerts to ensure timely intervention by correctional officers, according to one embodiment.

Visual Cues Indicating Physical Injury:

Unexplained Injuries 2622: Visual recognition software may identify signs of injury. When an officer is near an inmate with visible injuries, their gear may vibrate in a pattern indicating potential harm, according to one embodiment.

Limping or Difficulty Moving 2624: Motion detection algorithms may flag abnormal movements or difficulties in walking, signaling officers to check on the inmate's well-being, according to one embodiment.

Signs of Self-Harm 2626: AI may be trained to recognize signs of self-harm, especially in less visible body areas, and alert staff via a specific vibration pattern for immediate care, according to one embodiment.

Changes in Physical Appearance 2628: Significant changes detected by the system in an inmate's appearance may trigger a haptic alert for further investigation, according to one embodiment.

Visual and Behavioral Cues Indicating Mental Injury:

Withdrawal 2630: Monitoring the amount of time an inmate spends alone versus in social spaces may help identify withdrawal, triggering a haptic alert for officers to intervene, according to one embodiment.

Changes in Behavior 2632: Sudden changes in behavior patterns detected by AI may result in an alert, indicating the need for a psychological evaluation or intervention, according to one embodiment.

Self-Harm 2634 and Substance Abuse 2636: Detection of self-harm behaviors or unauthorized substance use may trigger specific haptic signals for urgent care, according to one embodiment.

Changes in Communication 2638: Analyzing changes in communication patterns, whether an increase or decrease in interaction, can alert staff to potential mental health issues, according to one embodiment.

Physical Symptoms of Stress 2640: AI may monitor complaints or signs of physical distress that might be related to stress or psychological issues, prompting a health check, according to one embodiment.

By utilizing a combination of AI-driven surveillance (e.g., using drone system 150 and stationary camera 2402) and haptic feedback (e.g., haptic response 400), correctional officers may be more effectively informed about the vast array of potential issues within the facility, ranging from gang-related activities to individual health concerns. This approach may enhance the ability to provide timely interventions, ultimately contributing to a safer and more secure environment for both inmates 2404 and staff (e.g., wearer 114), according to one embodiment.

Integrating haptic technology into the daily operations of correctional facilities 2400 may offer innovative ways to enhance security, improve officer response times, and ensure the well-being of both staff and inmates. Haptic feedback (e.g., haptic response 400 to the wearer 114 of the tactical gear 104) the of the AI system within the personal protective equipment 100 may guide officers to specific locations within the facility where incidents are occurring, using vibrations to indicate directions (left, right, forward), according to one embodiment.

In the event of an emergency requiring evacuation, haptic signals of the AI system within the personal protective equipment 100 may direct staff along the safest routes out of the facility (e.g., using the GPS module 116), adjusting in real-time based on the situation, according to one embodiment.

AI system within the personal protective equipment 100 may monitor physiological signs of stress (e.g., heart rate) and provide calming haptic feedback, such as rhythmic pulses that encourage deep breathing (e.g., as described in haptic table 1050 of the personal protective equipment 100), according to one embodiment.

Gentle, soothing vibration patterns during breaks within the personal protective equipment 100 may help reduce anxiety and improve mood, promoting mental health among staff, according to one embodiment. For situations requiring stealth, such as a surprise cell inspection or handling sensitive incidents, haptic signals generated by AI system within the personal protective equipment 100 may silently alert officers to commence operations simultaneously without alerting inmates, according to one embodiment.

Different vibration patterns generated by the AI system within the personal protective equipment 100 may indicate specific roles or actions during a coordinated response, ensuring each team member knows their immediate task without verbal communication, according to one embodiment.

The AI system within the personal protective equipment 100 may use haptic feedback in training sessions to simulate real-life scenarios, such as feeling the impact of physical confrontation (in a controlled manner) or the adrenaline rush of an emergency response, enhancing preparedness, according to one embodiment Immediate haptic feedback generated by the AI system within the personal protective equipment 100 during training exercises may reinforce correct actions or signal mistakes, speeding up the learning process, according to one embodiment.

Haptic signals may be used to non-verbally communicate with inmates 2404 when verbal communication might escalate a situation, such as vibrating wristbands to signal meal times or lockdowns, according to one embodiment. Officers equipped with haptic feedback devices within the personal protective equipment 100 may receive immediate tips or reminders about de-escalation techniques specific to the inmate they are interacting with, based on historical data, according to one embodiment.

Officers entering areas with potential chemical, biological, or radiological hazards may receive haptic warnings generated by the AI system within the personal protective equipment 100 if dangerous levels are detected by their wearables, according to one embodiment.

The AI system within the personal protective equipment 100 may track physical health metrics to alert officers to take a break, hydrate, or seek medical attention for signs of overheating, exhaustion, or other health concerns, according to one embodiment.

Haptic feedback generated by the personal protective equipment 100 may confirm when an officer has reached all required checkpoints during a security patrol, ensuring comprehensive coverage of the facility, according to one embodiment. If motion sensors detect unexpected movement in a supposedly unoccupied area, officers (e.g., wearer 114 of the personal protective equipment 100) nearby may receive immediate haptic alerts to investigate, according to one embodiment Further innovative applications of haptic technology in correctional facilities 2400 may lead to groundbreaking improvements in operational efficiency, safety protocols, and inmate management. For example, corrections officers may receive immediate haptic feedback (e.g., generated by the AI system within the personal protective equipment 100) when their communication devices, security scanners, or other critical equipment show signs of malfunction, ensuring they are always operational, according to one embodiment.

Haptic alerts 2210 may notify officers when they move too far away from essential equipment, like radios or keys, helping prevent loss or theft, according to one embodiment. Wearables (e.g., personal protective equipment 100) may monitor the density of people in specific areas, providing haptic alerts 2210 to officers (e.g., wearer 114) when areas become dangerously overcrowded, allowing for timely interventions, according to one embodiment.

Integrating sensors within the facility that detect structural weaknesses (like cracks in walls, ceiling issues) may send haptic alerts 2210 for preemptive maintenance, enhancing overall safety, according to one embodiment. In medical emergencies, officers equipped with haptic wearables (e.g., tactical gear 104) may receive prioritized alerts, guiding them to the exact location of the incident for a swift response, according to one embodiment.

For officers administering CPR or other emergency medical aid, haptic feedback may help maintain the correct rhythm and pressure, potentially saving lives, according to one embodiment. AI algorithms analyzing surveillance footage may identify unusual inmate behaviors that precede violent incidents or health crises, sending preemptive haptic alerts 2210 to officers (e.g., wearer 114), according to one embodiment.

For inmates 2404 with known health issues, haptic monitoring may alert staff if an inmate's movements suggest a possible sleep disorder or distress during the night, according to one embodiment. Haptic feedback (e.g., haptic response 400) may be used in training scenarios to simulate the sensation of an attack from different directions, improving defensive response times and awareness, according to one embodiment.

If an officer is in a compromised position or under attack, their wearable (e.g., personal protective equipment 100) may send distress signals through haptic feedback to other officers (e.g., wearer 114), ensuring rapid assistance, according to one embodiment. Haptic feedback may encourage energy-saving behaviors by alerting officers (e.g., wearer 114) when lights, water, or other resources are being used in excess, aligning with sustainability goals, according to one embodiment. Officers (e.g., wearer 114) may receive haptic reminders (e.g., haptic response 400) for routine tasks and checks, customizable to their shift patterns, ensuring no task is overlooked due to distraction or workload, according to one embodiment.

Use haptic feedback in educational programs for inmates 2404, such as vocational training, where tactile sensation may enhance learning, e.g., in woodworking or machinery operation, according to one embodiment. In facilities where direct physical contact is restricted, haptic devices (e.g., array of haptic sensors 210 of the personal protective equipment 100) may simulate the sensation of hand-holding or pats on the back during virtual visits, enhancing emotional connections, according to one embodiment.

Figure 27:
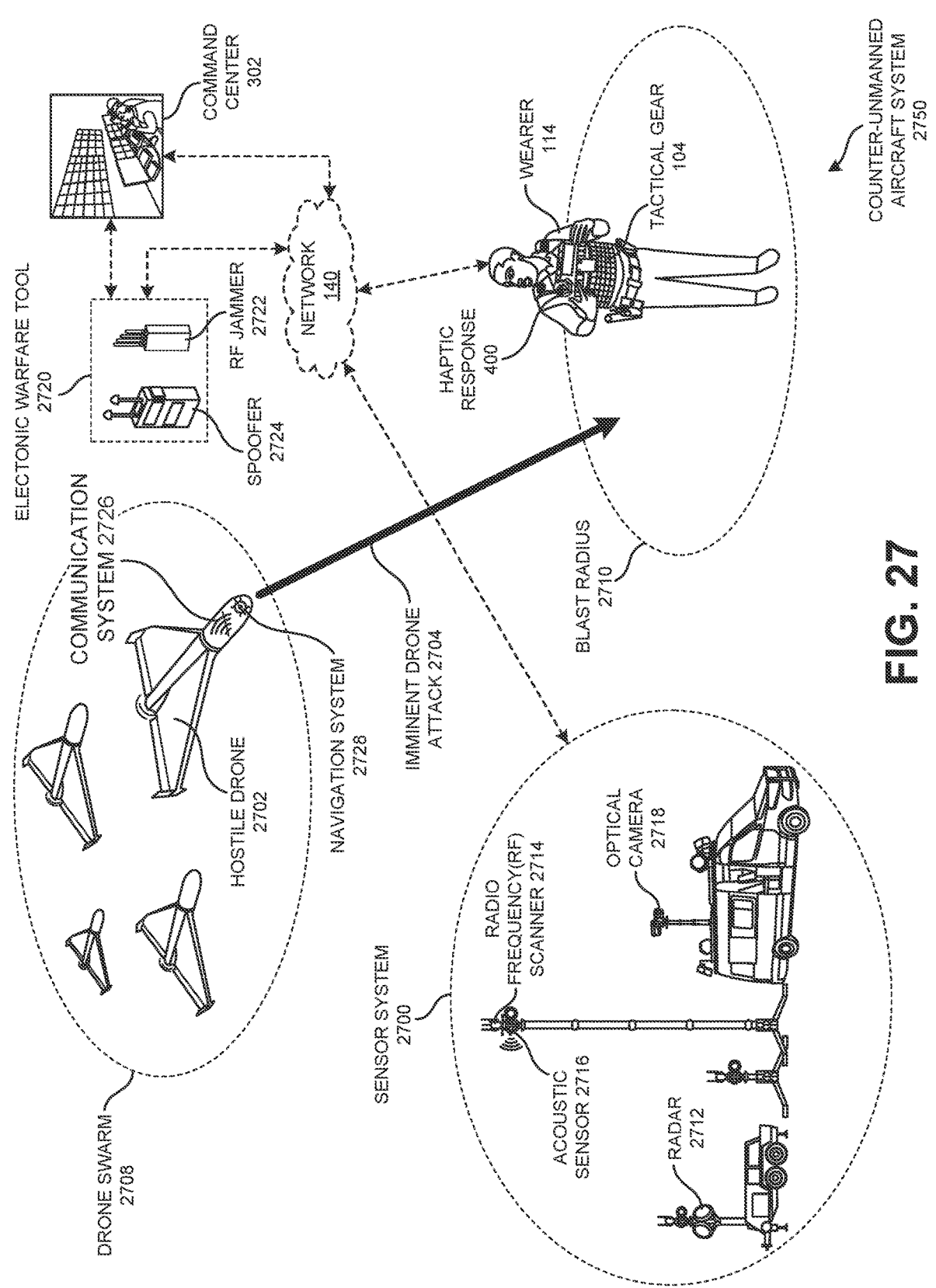
FIG. 27 is a counter unmanned aircraft system of the personal protective equipment of FIG. 1 to detect a presence of a hostile drone in the imminent drone attack and to control an electronic warfare tool to disrupt a communication and/or a navigation system of a hostile drone in the imminent attack, according to one embodiment.

FIG. 27 is a counter unmanned aircraft system 2750 of the personal protective equipment 100 of FIG. 1 to detect a presence of a hostile drone 2702 in the imminent drone attack 2704 and control an electronic warfare tool 2720 to disrupt a communication system and a navigation system of the hostile drone 2702 in the imminent drone attack 2704, according to one embodiment.

FIG. 27 depicts a multi-layered security system designed to protect against drone threats using an array of sensors and countermeasures integrated into both personal protective equipment 100 and the command center 302 by neutralizing drone threats, according to one embodiment.

The personal protective equipment 100 may be equipped with a comprehensive sensor system 2700 capable of detecting a hostile drone 2702. According to one embodiment, the sensor system 2700 may employ a suite of sensors in the form of counter unmanned aircraft system 2750 that may include:

The radar 2712 of the counter unmanned aircraft system 2750 may detect objects by bouncing radio waves off them and interpreting the reflected signals. The radar 2712 may detect drones based on their shape, speed, and trajectory, according to one embodiment. Ground-based radar systems may detect drones (e.g., hostile drone 2702) approaching a target by identifying objects moving through their coverage area. Advanced radar systems may be particularly adept at spotting small, low-flying drones (e.g., drone swarm 2708) by distinguishing them from other moving objects like birds or small aircraft. Short-range, high-resolution radar systems may be effective for this purpose, providing early warning of an approaching drone, according to one embodiment.

The Radio Frequency (RF) Scanner 2714 of the counter unmanned aircraft system 2750 may identify drones from the drone swarm 2708 by scanning for RF communications commonly used by drones to operate. The RF scanner 2714 may pick up communication and/or control signals between drones and their operators, according to one embodiment. These systems may detect the RF signals between drones and their operators. Since drones may communicate with their controllers using radio signals, RF detection systems may identify these communications, indicating the presence of a hostile drone 2702. These systems may be highly effective in detecting drones that are controlled remotely, potentially even before the hostile drone 2702 is physically near the wearer 114, according to one embodiment.

The acoustic sensor 2716 of the counter unmanned aircraft system 2750 may pick up sound signatures specific to hostile drone 2702, such as the whirring of rotors and/or unique sounds of drone propellers, according to one embodiment. Utilizing arrays of microphones, acoustic sensors can identify the unique sound signatures produced by drone propellers and motors. These systems 2716 may be particularly useful for detecting hostile drones 2702 that are attempting to approach a wearer 114 (and/or infrastructure, a vehicle) quietly and at low altitudes, where visual detection may be difficult, according to one embodiment.

The sensor system 2700 may be designed to detect imminent drone attacks near the sensor or a specific target leverage a combination of technologies to identify, track, and sometimes neutralize incoming unmanned aerial vehicles (UAVs). Each type of sensor may provide unique capabilities in identifying drone characteristics such as size, speed, altitude, and operational frequencies, according to one embodiment.

Optical cameras may visually detect hostile drones 2702 in the vicinity of the sensor system 2700 or target during daylight hours, while infrared cameras may detect the heat signatures produced by drones, making them effective for nighttime detection. These systems may be automated to alert operators to unusual movements or heat signatures that correspond with drone activity. However, their effectiveness may be diminished by poor weather conditions or obstructions in the line of sight, according to one embodiment.

Lidar (Light Detection and Ranging) systems may detect drones by emitting laser pulses and measuring the time it takes for the pulses to bounce back after hitting an object. This technology may generate detailed three-dimensional images of hostile drones 2702 approaching a target (e.g., a blast radius 2710). Lidar may be effective in various weather conditions and may detect hostile drones 2702 with a high degree of accuracy, although it may be expensive and has a relatively limited range compared to radar, according to one embodiment.

Electro-Optical (EO) Systems may use cameras to detect objects based on visible light. When combined with infrared (IR) sensors of the sensor system 2700 for thermal imaging, EO/IR systems may effectively identify hostile drones 2702 approaching a target by their shape during the day and by their heat signatures at night. These systems may also be equipped with tracking capabilities to follow a drone's movement once detected, according to one embodiment.

High-definition optical camera 2718 may offer visual confirmation. These cameras may capture detailed imagery, supporting identification and classification of the threat. When coupled with machine learning algorithms, the sensor system 2700 may automatically recognize and categorize different types of aerial threats, according to one embodiment.

UAV-Mounted Sensors on UAV 136 equipped with similar sensor technologies (radar, LIDAR, infrared, and cameras) may provide a bird's-eye view of the battlefield, extending the detection range far beyond the immediate vicinity of the vehicle. These UAVs 136 may relay crucial information back to the vehicle in real-time, according to one embodiment.

Ground-Based Sensor Arrays of the sensor system 2700 may be in strategic locations. These stationary sensors may form a network that offers wide-area surveillance, creating a perimeter of security. They may detect threats such as imminent drone attack 2704 approaching from different directions and altitudes, feeding data back to the patrol vehicle 700 and command centers 302, according to one embodiment.

Satellite Sensors may offer the broadest coverage, satellite sensors may monitor large swathes of territory from space. Equipped with advanced imaging, radar, and infrared technologies, satellites may detect missile launches or large drone formations (e.g., drone swarm 2708) early, providing vital strategic intelligence, according to one embodiment.

Communication and Data Links may enable off-vehicle sensors to be effective, where robust communication and data link systems are essential. These systems may ensure secure, low-latency transmission of sensor data to the vehicle, enabling the AI to process and respond to threats in real-time, according to one embodiment.

To ensure comprehensive coverage and mitigate the limitations of each sensor type, a multi-sensor approach may be employed. By integrating data from radar, RF detectors, acoustic sensors, and optical/IR cameras, ground-based systems can create a layered defense capable of detecting and assessing the threat of an imminent drone attack with high accuracy. This integrated approach enhances the ability to detect, track, and respond to drones before they can reach their intended targets, providing critical time for countermeasures to be enacted, according to one embodiment.

The optical camera 2718 of the counter unmanned aircraft system 2750 may visually identify drones, potentially using image recognition software to differentiate between friendly and hostile units of the drone swarm 2708, according to one embodiment.

The sensors of the sensor system 2700 may work in tandem to detect the presence of a hostile drone 2702, indicated by the imminent drone attack 2704. This multi-sensor approach may increase accuracy and reduce the chance of false positives, according to one embodiment.

Upon detecting a threat, the sensor system 2700 may calculate the potential blast radius 2710 of an attack, informing response measures and evacuation protocols. The potential blast radius 2710 may underscore the critical need for timely detection and response to mitigate the risk of damage from a drone attack, according to one embodiment.

When the sensor system 2700 detects a drone that poses a threat, it may send an alert through the network 140 to both the command center 302 and the tactical gear 104. A geo-location device of the system may identify a present location of the wearer 114 when the sensor system 2700 detects the imminent drone attack. The present location is communicated to the command center. The haptic response mechanism in the tactical gear 104 may be then activated, notifying the wearer 114 of the imminent threat. The command center 302 may direct a series of counter measures to neutralize the hostile drone 2702 in the imminent drone attack, according to one embodiment.

C-UAS (Counter-Unmanned Aerial Systems) of FIG. 27 may be a system that uses a variety of methods to detect, track, and neutralize hostile drones 2702. They can include electronic warfare methods to jam the communication and control signals of drones (e.g., navigation system 2728 and communication system 2726 of the hostile drone 2702), kinetic methods to physically intercept and destroy them (like nets or projectiles), and laser systems to damage or destroy drones, according to one embodiment.

Faraday Cages and EMP Defense: To protect sensitive equipment from the electromagnetic pulse (EMP) effects of some types of attacks (though more speculative in the context of drone warfare), Faraday cages can shield electronics by blocking external static and non-static electric fields, according to one embodiment.

The tactical gear 104 can be wirelessly connected to both the vehicle's GovGPT™ Pufferfish system and external sensor networks (e.g., sensor system 2700). This connection allows it to receive real-time updates about aerial threats. In addition to haptic alerts 2210, the tactical gear 104 can incorporate visual signals (LEDs) or auditory signals (earpiece connectivity) for comprehensive awareness. This may enhance situational awareness of the wearer 114 without relying solely on visual or auditory cues, which can be crucial in noisy, chaotic combat environments because it may permit the wearer 114 to react quickly to threats, especially when inside vehicles or buildings where visibility may be limited. In conflict zones, civilians equipped with the tactical gear 104 can receive early warnings about imminent drone attacks 2704, giving them crucial seconds to seek cover or evacuate the area. This may be particularly useful in humanitarian operations, providing aid workers with an additional layer of safety while operating in high-risk areas. The system may require a centralized control unit within the vehicle or command center 302 to process threat data and broadcast it to all connected vests in the vicinity. Regular updates and synchronization with the GovGPT™ Pufferfish system may ensure that the tactical vest's 104 alert protocols are always aligned with the latest threat detection capabilities, according to one embodiment.

This tactical gear 104 concept may combine modern wearable technology with advanced threat detection systems (e.g., using threat detection model 108 of the compute module 118), offering a proactive solution to enhance safety and situational awareness for both military personnel and civilians (e.g., wearer 114) in conflict zones, according to one embodiment. The tactical gear 104 designed for alerting wearers 114 of incoming drone threats through haptic, visual, and auditory signals may be crafted with the intent of providing both flexibility and comprehensive situational awareness. This detailed approach ensures that individuals can receive and understand alerts without being overwhelmed or distracted, which can be crucial in high-stress environments, according to one embodiment.

The tactical gear 104 may have a user interface, possibly a small, rugged, touch-screen panel or a mobile application, allowing the wearer 114 to personalize how they receive alerts. For instance, a wearer 114 might prefer strong vibrations for imminent threats but softer pulses for alerts about distant hostile drones 2702, according to one embodiment.

Before a mission, wearers 114 can program the tactical vest's 104 alert system to match specific operational requirements, according to one embodiment. For example, in stealth operations, visual or auditory alerts might be preferred over haptic ones to maintain silence, according to one embodiment. The system can include biometric sensors 160 to monitor the wearer's physical state (heart rate, for instance) and adjust alert intensities accordingly. If the wearer's heart rate indicates high stress, the system might reduce alert intensity to prevent additional stress, according to one embodiment.

Integrated actuators distributed throughout the tactical gear 104 may deliver vibrations or pulses directly to the wearer's body. These can vary in pattern and intensity, providing a nuanced and immediate sense of the threat's direction and urgency, according to one embodiment. For instance, escalating vibrations (e.g., haptic alert 2210) can indicate an approaching ambient threat 132, while a single strong pulse can signal an immediate need to take cover, according to one embodiment.

LED strips or patches integrated into the tactical vest's 104 fabric can light up or change color based on the threat level, according to one embodiment. For nighttime operations, these lights can be visible only through night-vision goggles to prevent giving away the wearer's position, according to one embodiment. A color-coded system might use green to indicate all-clear, yellow for caution, and red for immediate danger, according to one embodiment. For wearers 114 equipped with tactical earpieces, the tactical gear 104 can send auditory alerts directly to the earpiece. This can include synthesized voice warnings with details about the threat ("Drone incoming, 200 meters, northeast") or coded sounds designed to convey urgency and direction without the need for translation. The volume and nature of these sounds can be adjusted based on ambient noise levels and the wearer's hearing protection, according to one embodiment.

The integration of these haptic alert 2210 systems aims to create a multimodal awareness environment, ensuring that the wearer 114 can quickly and accurately assess ambient threats 132 without needing to rely on a single sense, according to one embodiment. This approach may be particularly valuable in combat or disaster-response scenarios, where sensory overload is common, and the ability to quickly interpret and act on information can be life-saving, according to one embodiment. The customizable nature of the alert system may ensure that it can be adapted not only to individual wearer preferences and needs but also to the specific operational context, enhancing both personal safety and mission effectiveness, according to one embodiment. This level of customization and integration of alerts represents a significant advancement in wearable defense technology, offering a new standard for personal situational awareness in high-risk environments, according to one embodiment. Creating a system where each individual (e.g., wearer 114) may be paired with a personal surveillance drone (e.g., using drone system 150) for counter-drone operations involves a sophisticated network of wearable technology, drone control systems, and AI-driven command and control protocols, according to one embodiment.

AI-Driven command and control system (e.g., using compute module 118 of the tactical gear 104) may be a centralized software that processes data from all deployed personal drones, analyzes threats, and coordinates counter-drone responses, according to one embodiment. This system can identify enemy drones, assess their threat level, and recommend or automate countermeasures, according to one embodiment. Upon detection of an enemy hostile drone 2702 or drone swarm 2708, the counter unmanned aircraft system 2750 alerts the wearer 114 through their wearable control unit, according to one embodiment. The wearer 114 can then deploy their personal surveillance drone (e.g., UAV 136) with a single command using the drone control apparatus 124, according to one embodiment. The deployed drones autonomously navigate to the threat location identified as blast radius 2710, using onboard sensors (e.g., thermal sensor 916) to gather intelligence, according to one embodiment. This data may be relayed back to the command and control system (e.g., database of the command center 302) for analysis, according to one embodiment.

Based on the threat analysis, the system may determine the best course of action. If a direct impact with the enemy's hostile drone 2702 is deemed the most effective response, the system can direct the personal surveillance drone (e.g., UAV 136) to intercept and neutralize the threat, according to one embodiment. The wearer 114 may have the option to manually control their drone at any time, using the wearable drone control apparatus 124 to direct the drone's movements, adjust surveillance parameters, or execute a counter-drone maneuver, according to one embodiment.

After the threat is neutralized, the drone (e.g., UAV 136) returns to the wearer 114, automatically docking with a charging station integrated into the wearable drone control apparatus 124 or the user's patrol vehicle 700 to prepare for the next deployment, according to one embodiment.

The counter unmanned aircraft system 2750 of the personal protective equipment and the command center may control an electronic warfare tool 2720, such as a RF jammer 2722 and a spoofer 2724, to disrupt the communication system 2726 and the navigation system 2728 of the hostile drone 2702 in the imminent attack 2704. The RF jammer 2722 may cut off the control of hostile drone 2702 from its operator and the spoofer 2724 may interfere with the drone's navigation system, forcing it to land or return to its point of origin. The command center 302, upon receiving the same information, may coordinate an appropriate defense strategy, which may include deploying countermeasures against the drones. The countermeasures may aim to neutralize the drone without engaging in kinetic or destructive action, minimizing the risk of collateral damage. FIG. 27 illustrates a comprehensive approach to drone defense, combining detection, communication, wearer notification, and electronic countermeasures to ensure a swift and effective response to aerial threats, according to one embodiment.

Figure 28:
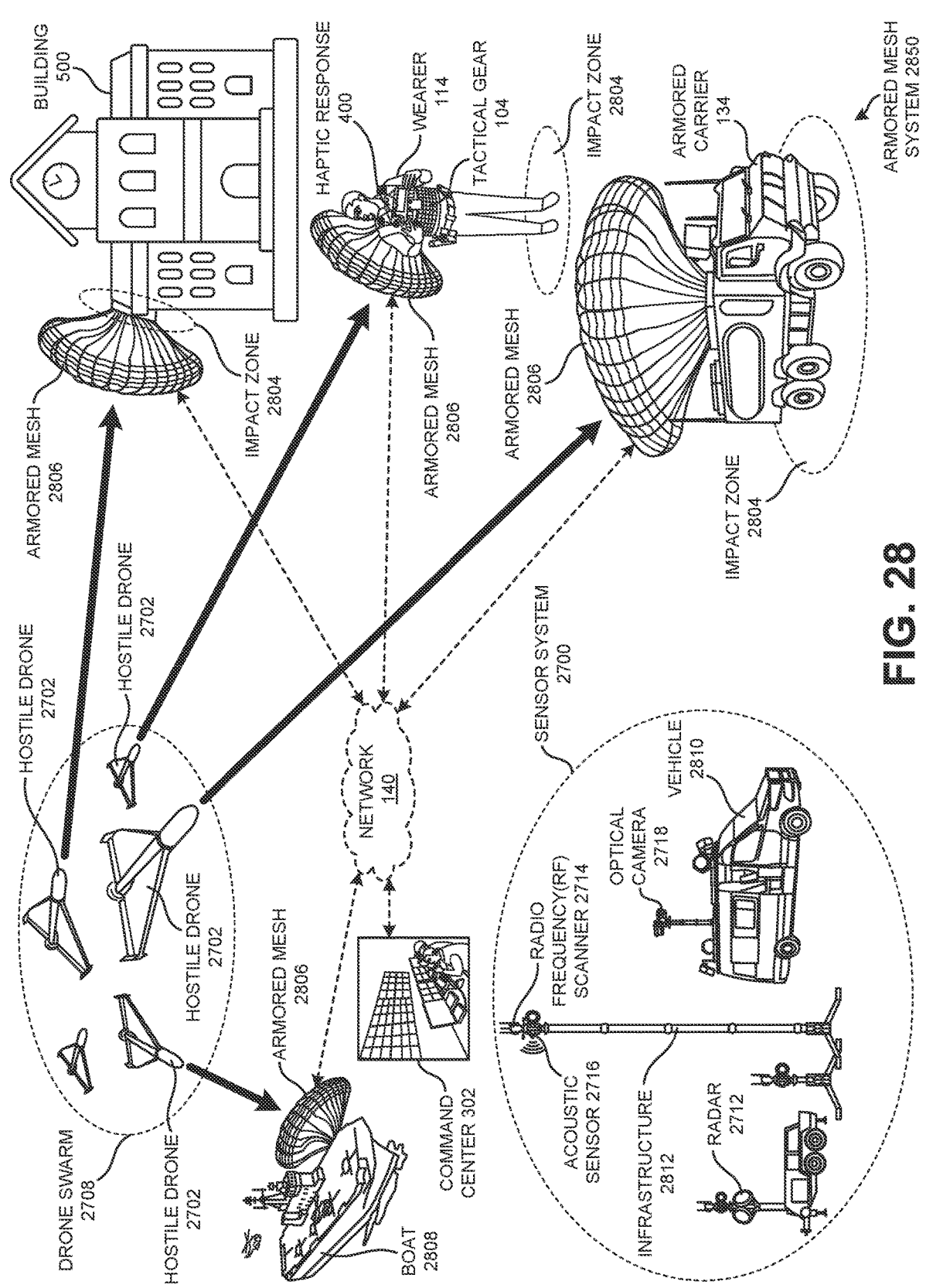
FIG. 28 is a system view of an armored mesh system that can automatically deploy, inflate, and deflate based on an imminent drone attack, according to one embodiment.

FIG. 28 is a system view of an armored mesh system 2850 that can automatically deploy, inflate, and deflate based on an imminent drone attack 2704. Specifically, the GovGPT™ Pufferfish is an innovative armored mesh system 2850 designed for safeguarding protected assets such as boat 2808, vehicle 2810, infrastructure 2812, armored carrier 134, building 500, and the wearer 114 by providing dynamic protection against aerial threats such as drones or loitering munitions. This advanced defensive mechanism is named for its rapid deployment capability, resembling a pufferfish's ability to quickly expand in the face of threats, according to one embodiment.

The sensor system 2700 of the advanced armored mesh system 2850 may detect the hostile drones 2702, part of the drone swarm 2708, which may imminently collide with the protected assets in the impact zones 2804. Upon detection of the hostile drone 2702, the system may calculate the drone's direction relative to the protected assets (e.g., as boat 2808, vehicle 2810, infrastructure 2812, armored carrier 134, building 500, and the wearer 114) and the estimated time until impact, sending this information to the tactical gear 104 and/or the command center 302. The sensor system 2700 of the advanced armored mesh system 2850 may precisely predict the location and intensity of the detected threat in the identified impact zone 2804 of the protected asset.

The responsive mechanism of the advanced armored mesh system 2850 may automatically trigger the deployment of the armored mesh 2806. The armored mesh 2806 may preserve the protected asset in the identified impact zone 2804 by rapidly expanding and intercepting the imminent attack to effectively neutralize the impact of the attack. The responsive mechanism of the advanced armored mesh system 2850 may use high-pressure gas and/or other rapid expansion technology to unfold the mesh barrier within milliseconds, intercepting the threat before its impact in the impact zone 2804, according to one embodiment.

The armored mesh 2806 may be made of high-strength, lightweight materials capable of withstanding high-speed impacts and potentially explosive forces to allow for quick expansion while maintaining a compact storage profile when not in use.

The system may provide real-time surveillance data directly to the wearer 114, allowing for immediate awareness of aerial threats (e.g., imminent drone attack 2704), according to one embodiment. By equipping each wearer 114 and the protected asset with a personal drone and armored mesh 2806, the system creates a distributed defense network, increasing redundancy and resilience against drone swarms 2708, according to one embodiment.

The balance between autonomous operation and manual control may ensure that the counter unmanned aircraft system 2750 and the armored mesh system 2850 can respond effectively under various conditions, while still allowing human decision-making where necessary, according to one embodiment. The armored mesh system 2850 may be scaled up for large units such as buildings 500 or scaled down for individual (e.g., wearer 114) operatives, making it versatile for different operational contexts, according to one embodiment. Equipped with cutting-edge sensors, the GovGPT™ Pufferfish system detects incoming threats from above. Upon detection, it activates a series of armored mesh system 2850 mounted on the vehicle's (e.g., armored carrier 134) exterior, specifically the roof and potentially vulnerable areas, according to one embodiment.

The armored mesh 2806 may be crafted from ultra-strong, blast-resistant fabrics capable of withstanding explosive forces and shrapnel, incorporating a web-like internal structure to catch and neutralize smaller projectiles and fragments, according to one embodiment. Emulating the rapid inflation of a pufferfish, this armored mesh system 2850 deploys within milliseconds, creating an instantaneous barrier against incoming attacks. Beyond merely blocking threats, the inflated armored mesh 2806 may disperse countermeasures, including nets or electromagnetic pulses, to further disable or destroy the incoming hostile drones 2702 or munitions (e.g. imminent drone attack 2704), according to one embodiment.

Unlike static armor, the GovGPT™ Pufferfish system (e.g., armored mesh system 2850) may offer comprehensive protection that activates only when needed, preserving the vehicle's (e.g., armored carrier's 134) speed and maneuverability until deployment, according to one embodiment. After deployment and threat neutralization, the armored mesh system 2850 quickly deflates and prepares for subsequent activations, ensuring continuous protection, according to one embodiment. This armored mesh system 2850 complements existing defense mechanisms, such as active protection systems (APS), by providing an additional layer of defense against threats that might bypass traditional countermeasures, according to one embodiment. The detection system (e.g., counter unmanned aircraft system 2750) may distinguish between actual threats and non-threatening objects to avoid unnecessary deployments, according to one embodiment.

The system's (e.g., armored mesh system 2850) materials may endure harsh environments and repeated deployments, requiring minimal maintenance for operational readiness, according to one embodiment. Incorporating the GovGPT™ Pufferfish into current military vehicles (e.g., armored carrier 134) may involve compatibility checks with existing armor and defense systems to ensure cohesive protection, according to one embodiment.

Ultra-High-Molecular-Weight Polyethylene (UHMWPE) may be material known for its high strength-to-density ratio, making it one of the preferred choices for ballistic protection for the armored mesh system 2850, according to one embodiment. It's used in personal body armor and may serve as the outer layer of the armored mesh 2806, providing significant resistance against high-speed projectiles and shrapnel, according to one embodiment. Materials like Kevlar, known for their heat resistance and strength, can be used in layers underneath the UHMWPE to absorb and dissipate the force of impacts, according to one embodiment. Aramid fibers are engineered to provide a high level of protection while maintaining flexibility, which may be crucial for rapid deployment and packing of the armored mesh system 2850, according to one embodiment.

Introducing graphene, one of the strongest known materials, into the fabric can significantly enhance the blast resistance for the armored mesh 2806, according to one embodiment. Graphene's incorporation can improve the material's ability to distribute the force of a blast across a wider area within the armored mesh 2806, reducing the impact at any single point, according to one embodiment.

The armored mesh 2806 may feature an intricate webbing or mesh structure internally, made from high-tensile materials such as carbon nanotubes or advanced metallic alloys, according to one embodiment. This design may be intended to catch and neutralize smaller projectiles that might penetrate the outer layers, according to one embodiment. The webbing can deform upon impact, absorbing energy and preventing the projectile from causing further damage, according to one embodiment. To ensure the armored mesh 2806 may provide protection exactly where it's needed, a segmented design can be employed, allowing for targeted inflation, according to one embodiment. This approach can enable specific sections of the armored mesh 2806 to deploy rapidly in response to the direction of the incoming threat, maximizing efficiency and minimizing unnecessary exposure, according to one embodiment.

Incorporating self-healing polymers that can repair minor tears or punctures can extend the armored mesh system 2850 operational life and maintain protective integrity over time, according to one embodiment. These materials may typically involve microcapsules that release a healing agent when breached, according to one embodiment. Advanced sensors, combined with artificial intelligence, may monitor the external environment for threats, controlling the deployment of the airbags with precision, according to one embodiment. The armored mesh system 2850 can predict the impact zone 2804 and deploy the armored mesh 2806 preemptively to provide an effective shield, according to one embodiment.

Incorporating materials that can absorb and convert kinetic energy into other forms, such as heat or light, can further enhance the protective capabilities of the armored mesh 2806, according to one embodiment. These materials would help to dissipate the energy of the blast or projectile, reducing the transmitted force, according to one embodiment. The GovGPT™ Pufferfish armored mesh system 2850 represents a cutting-edge approach to military vehicle (e.g., armored carrier 134) protection, leveraging advancements in material science and engineering to create a deployable defense mechanism against modern threats, according to one embodiment. The combination of ultra-strong fabrics, strategic design, and technological integration sets a new standard for protective systems in conflict zones, according to one embodiment.

The deployment mechanism of the GovGPT™ Pufferfish system, idealized for military vehicles (e.g., armored carrier 134) to protect against aerial threats (e.g., imminent drone attack 2704 from hostile drone 2702), may involve a complex yet highly efficient process, according to one embodiment. This mechanism may be designed to rapidly deploy airbags (e.g., armored mesh 2806) crafted from advanced materials upon detecting an incoming threat, according to one embodiment. The armored mesh system 2850 may be integrated with state-of-the-art technology to ensure quick response and maximum protection, according to one embodiment.

The initial stage may involve a network of sensors equipped around the vehicle (e.g., armored carrier 134), utilizing radar, lidar, and infrared technology to continuously monitor the surrounding airspace for potential threats such as drones or munitions, according to one embodiment. Data from the sensors feed into an onboard AI system that analyzes the trajectory, speed, and type of incoming threats in real-time, according to one embodiment. This system distinguishes between false alarms and genuine threats by comparing the object's behavior against known threat patterns (e.g., imminent drone attack 2704), according to one embodiment. Upon identifying a legitimate threat, the system may calculate the optimal deployment time and airbag sections (e.g., armored mesh 2806) needed to intercept the threat based on its trajectory and speed, according to one embodiment. A signal may then be sent to the airbag deployment system, specifying which airbag modules (e.g., armored mesh 2806) to activate, according to one embodiment. This targeted approach ensures that protection may be provided precisely where it may be needed, conserving resources and maintaining vehicle (e.g., armored carrier 134) maneuverability for as long as possible, according to one embodiment.

The armored mesh 2806 may be equipped with high-speed inflation systems, using compact, high-pressure gas canisters that can fully inflate the armored mesh 2806 within milliseconds, according to one embodiment. These canisters are activated electronically, ensuring a synchronized deployment around the vehicle (e.g., armored carrier 134), according to one embodiment. Given the segmented design of the armored mesh system 2850, only the modules directly in the path of the incoming threat will inflate, according to one embodiment. This precision deployment minimizes the system's impact on the vehicle's (e.g., armored carrier's 134) operational capabilities and visibility, according to one embodiment. As the armored mesh 2806 inflate, they unfold layers of ultra-strong, blast-resistant fabrics designed to absorb and dissipate the energy of impacts and explosions, significantly reducing the damage potential, according to one embodiment. Within the fabric layers, a web-like structure of high-tensile materials may expand to create a mesh barrier, capable of catching and neutralizing smaller fragments or projectiles that penetrate the outer layer, according to one embodiment.

After the threat has been neutralized, the system quickly deflates the deployed airbags, pulling them back into their compartments. The armored mesh 2806 of the armored mesh system 2850 then immediately resets, readying itself for the next threat detection and deployment cycle. Concurrently, the onboard AI conducts a rapid assessment of the system's integrity, ensuring all components are functional and ready for reactivation. Any detected damages or malfunctions trigger a maintenance alert to the vehicle's crew, according to one embodiment.

This deployment mechanism may be engineered to offer a blend of rapid response, precise threat interception, and minimal interference with the vehicle's functionality, according to one embodiment. By leveraging advanced materials, AI, and sensor technology (e.g., sensor system 2700), the GovGPT™ Pufferfish system (e.g., armored mesh system 2850) may provide an innovative solution to modern military challenges, enhancing vehicle survivability in complex threat environments, according to one embodiment. The Rapid Inflation Technology and Rapid Deflation and Reset mechanisms of the GovGPT™ Pufferfish system (e.g., armored mesh system 2850) are sophisticated components designed to offer immediate protection and quick recovery for military vehicles (e.g., armored carrier 134) under threat, according to one embodiment.

The core of the armored mesh system 2850 relies on compact canisters filled with a high-pressure gas, such as helium or nitrogen, according to one embodiment. These gases are chosen for their ability to expand rapidly and their inert nature, reducing the risk of combustion upon deployment, according to one embodiment. Each canister of the armored mesh system 2850 may be linked to an electronic trigger that activates upon receiving a signal from the vehicle's threat detection system, according to one embodiment. This ensures precise timing, crucial for the armored mesh 2806 to be effective against fast-approaching threats, according to one embodiment. To provide comprehensive protection, the system may be designed to deploy armored mesh 2806 in a synchronized manner around the vehicle. This can be achieved through a control unit that coordinates the activation signals, ensuring that all relevant armored mesh 2806 inflate simultaneously, within milliseconds of detection, according to one embodiment.

Upon activation, the gas may be released from the canisters through a specially designed valve system that controls the flow rate, ensuring the armored mesh 2806 inflate at an optimal speed to meet the incoming threat, according to one embodiment. The design of the armored mesh 2806 fabric and the internal pressure created by the gas expansion are calibrated to achieve full inflation in the shortest possible time, usually within milliseconds, according to one embodiment. After the threat is neutralized, the advanced armored mesh system 2850 initiates a rapid deflation process. This involves the release of the gas from the armored mesh 2806 through controlled venting mechanisms, according to one embodiment. These vents are designed to quickly expel the gas in a safe and controlled manner, deflating the armored mesh 2806 without endangering the vehicle or its occupants, according to one embodiment. Concurrent with deflation, mechanical systems-such as retractors or rollers-activate to pull the deflated armored mesh 2806 back into their storage compartments, according to one embodiment. This process may be automated and optimized to be completed quickly to minimize downtime between threats, according to one embodiment.

Once the armored mesh 2806 are fully retracted and stored, the armored mesh system 2850 automatically checks for readiness for the next deployment, according to one embodiment. This includes a diagnostic check of the armored mesh 2806 integrity, gas canister pressure levels, sensor functionality, and electronic components, according to one embodiment. If any issues are detected, the armored mesh system 2850 alerts the vehicle's crew (e.g., wearer 114) for maintenance, according to one embodiment. Otherwise, it re-arms itself, ready to deploy again at a moment's notice, according to one embodiment. The design allows for quick replacement of gas canisters and inspection of armored mesh 2806 and mechanical components, ensuring the system can be rapidly returned to operational status even after deployment, according to one embodiment. This sophisticated inflation and deflation mechanism provides the GovGPT™ Pufferfish system (e.g., armored mesh system 2850) with a unique capability to offer instant protection against threats while ensuring the vehicle remains ready to respond to subsequent threats with minimal delay, according to one embodiment. The use of advanced materials and engineering ensures that this armored mesh system 2850 can withstand the rigors of combat environments, offering both immediate and sustained protection, according to one embodiment.

The GovGPT™ Pufferfish system (e.g., armored mesh system 2850) may be a conceptual advanced defense mechanism tailored specifically for military vehicles, designed to offer rapid and effective protection against aerial threats such as hostile drones 2702, guided missiles, and other airborne projectiles, according to one embodiment. This armored mesh system 2850 integrates state-of-the-art material technology and artificial intelligence to detect threats and deploy protective measures (e.g., armored mesh 2806) instantly, ensuring the safety of the armored carrier 134 and its occupants in high-threat environments, according to one embodiment.

Immediately after the threat has been neutralized, the armored mesh system 2850 activates controlled venting valves within the airbag modules, allowing the high-pressure gas to escape quickly and safely, initiating the deflation process, according to one embodiment. As the armored mesh 2806 deflate, specialized retraction mechanisms, such as rollers or compactors within the module, engage to assist in the orderly and rapid retraction of the airbag fabric back into its storage compartment, according to one embodiment. Integrated sensors continuously monitor the status and integrity of each component during and after deployment, according to one embodiment. This includes checks for potential damage to the armored mesh 2806, the gas canisters' remaining pressure, and the operational status of the electronic control unit (ECU) and sensors, according to one embodiment. Any issues detected, such as leaks, tears, or depleted gas canisters, are automatically reported to the vehicle's central computer system, according to one embodiment. This step may ensure that crew members are immediately aware of the armored mesh system 2850 status and any maintenance requirements, according to one embodiment.

In systems designed with onboard gas generation or refill capabilities, the canisters may be automatically re-pressurized in preparation for the next deployment, according to one embodiment. For systems relying on replaceable gas canisters, the diagnostic system flags depleted units for manual replacement, guiding maintenance personnel with precise location and replacement instructions, according to one embodiment. Once the armored mesh 2806 are fully retracted and any identified issues addressed, the ECU may initiate a reset command, restoring the armored mesh system

2850 to its default state, ready for immediate re-deployment, according to one embodiment.

The armored mesh system 2850 may then perform a final check to confirm all armored mesh 2806 are correctly stored, and all components are fully functional, according to one embodiment. The armored mesh system 2850 may then be officially re-armed, with the ECU ready to respond to new threats, according to one embodiment. The GovGPT™ Pufferfish system (e.g., armored mesh system 2850) may transition to a standby mode, where it continues to monitor the environment for threats but with minimized energy consumption, ensuring readiness without undue drain on vehicle resources, according to one embodiment.

This automatic reset process can be critical for maintaining the efficacy and readiness of the GovGPT™ Pufferfish system (e.g., armored mesh system 2850), ensuring military vehicles are continuously protected with minimal downtime, according to one embodiment. Advanced algorithms, robust mechanical designs, and smart material choices are key to achieving such rapid recovery and reset capabilities, ensuring that vehicles can maintain high operational tempo even in environments with frequent aerial threats, according to one embodiment.

Enhancing the GovGPT™ Pufferfish system (e.g., armored mesh system 2850) with sensors external to the vehicle can significantly improve its AI-driven threat detection capabilities, according to one embodiment. By utilizing a network of external sensors (e.g., sensor system 2700), deployed in strategic locations around the operational area or mounted on other assets such as unmanned aerial vehicles (UAVs), ground-based installations, or even satellites, the armored mesh system 2850 can achieve a more comprehensive situational awareness and earlier threat detection, according to one embodiment.

External sensors (e.g., sensor system 2700) may detect threats at greater distances, providing early warnings to the vehicle, allowing for more preparation time. Deploying sensors in a distributed manner can cover blind spots and provide a 360-degree surveillance radius around the vehicle, according to one embodiment. Information from external sensors (e.g., sensor system 2700) can be integrated with the vehicle's onboard sensors, enriching the data available for analysis, according to one embodiment. This fusion of data allows the AI to make more accurate predictions about the threat's nature, speed, and trajectory, according to one embodiment. With additional data points from external sources, the (e.g., armored mesh system 2850) can track multiple threats simultaneously with greater precision, improving the vehicle's defensive response, according to one embodiment. External sensors can be connected to the vehicle through secure, real-time communication networks, ensuring that the AI has up-to-the-second information, according to one embodiment.

By leveraging a decentralized approach to threat detection, where external sensors contribute to the overall situational awareness, the armored mesh system's 2850 resilience against jamming or spoofing attacks can be significantly enhanced, according to one embodiment. The AI can analyze patterns and predict potential threat zones by synthesizing data from both vehicle-mounted and external sensors (e.g., sensor system 2700), enabling proactive defensive maneuvers, according to one embodiment. Depending on the threat level and type, the AI can dynamically adjust the vehicle's speed, trajectory, and even suggest deployment of countermeasures, optimizing the chances of evading or mitigating the threat, according to one embodiment. Ensuring that external sensors (e.g., sensor system 2700) and the vehicle's onboard systems can communicate effectively may require standardized data formats and communication protocols, according to one embodiment.

The data links between external sensors (e.g., sensor system 2700) and the vehicle must be secured against interception and hacking to prevent false data feeds or disruption of the defensive system, according to one embodiment. By incorporating external sensors (e.g., sensor system 2700) into the GovGPT™ Pufferfish system (e.g., armored mesh system 2850), military vehicles can achieve a more layered and effective defense mechanism against aerial threats (e.g., imminent drone attack 2704), significantly improving situational awareness and operational effectiveness in contested environments, according to one embodiment. This multi-layered sensor approach using the sensor system 2700 of the counter unmanned aircraft system 2750 and armored mesh system 2850 combined with advanced AI analytics, may be the cutting edge in military defensive technologies, providing enhanced protection for assets in increasingly complex and threat-dense operational theaters, according to one embodiment.

A drone detection artificial intelligence model (e.g., analogous to the threat detection model 108) of the personal protective equipment 100 and a command center 302 may classify and/or identify the drone type, the model, and potentially of its payload of the hostile drone 2702 in the imminent drone attack 2704 by comparing sensor data against databases of known drone signatures to assess the level of threat and to decide on an appropriate response, according to one embodiment.

Many embodiments have been described. Nevertheless, it will be understood that various modifications may be made without departing from the spirit and scope of the claimed invention. For example, the personal protective equipment 100 may be the GovGPT™ tactical gear 104 in any form (e.g., including helmet form). Also, embodiments described for one use case, such as for law enforcement, may apply to any of the other use cases described herein in any form. In addition, the logic flows depicted in FIGS. 1-28 do not require the particular order shown, or sequential order, to achieve desirable results. In addition, other steps may be provided, or steps may be eliminated, from the described flows. Other components may be added or removed from the described systems. Accordingly, other embodiments are within the scope of the following claims. It may be appreciated that the various systems, methods, and apparatus disclosed herein may be embodied in a machine-readable medium and/or a machine-accessible medium compatible with a data processing system (e.g., a computer system), and/or may be performed in any order.

Although the present embodiments have been described with reference to specific example embodiments, it will be evident that various modifications and changes may be made to each of the embodiments in the FIGS. 1-28 without departing from the broader spirit and scope of the various embodiments. Features in one embodiment and use case may be applicable to other use cases as described, and one with skill in the art will appreciate this and those interchanges are incorporated as embodiments of each use case- fire, military, police, civilian, journalism, EMT etc. For example, the various devices and modules described herein may be enabled and operated using hardware circuitry (e.g., GPUs, CMOS based logic circuitry), firmware, software or any combination of hardware, firmware, and software (e.g., embodied in a non-transitory machine-readable medium). For example, the various electrical structures and methods may be embodied using transistors, logic gates, and electrical circuits (e.g., graphics processing units (GPUs), application-specific integrated (ASIC) circuitry and/or Digital Signal Processor (DSP) circuitry). In addition, it may be appreciated that the various systems, methods, and apparatus disclosed herein may be embodied in a machine-readable medium and/or a machine-accessible medium compatible with a data processing system (e.g., a computer system), and/or may be performed in any order. The structures and modules in FIGS. 1-28 may be shown as distinct and communicating with only a few specific structures and not others. The structures may be merged with each other, may perform overlapping functions, and may communicate with other structures not shown to be connected in the Figures.

Many embodiments have been described. Nevertheless, it will be understood that various modifications may be made without departing from the spirit and scope of the claimed invention. For example, the GovGPT™ Body-worn safety device may be the GovGPT™ tactical gear in any form (e.g., including helmet form). Also, embodiments described for one use case, such as for law enforcement, may apply to any of the other use cases described herein in any form. In addition, the logic flows depicted in the Figures do not require the particular order shown, or sequential order, to achieve desirable results. In addition, other steps may be provided, or steps may be eliminated, from the described flows. Other components may be added or removed from the described systems. Accordingly, other embodiments are within the scope of the following claims.

The invention claimed is:

1. A personal protective equipment, comprising:
a language translator module integrated in a tactical gear through which a wearer to bi-directionally communicate with an individual in an ambient environment using any language other than a primary language spoken by the wearer when the language translator module is activated;
a biometric sensor of the tactical gear to detect a health condition of the wearer; and
a responsive device integrated in the tactical gear,
wherein the responsive device to vibrate when the biometric sensor detects an elevated stress level of the wearer of the tactical gear.

2. The personal protective equipment of claim 1 wherein the elevated stress level is detected through a heart rate monitor which determines whether a heart rate of the wearer is beyond an acceptable range.

3. The personal protective equipment of claim 2 wherein the heart rate monitor to evaluate a heart rate variability (HRV), which is a variation in time between each heartbeat, and wherein a lower HRV is an indicator of the elevated stress level.

4. The personal protective equipment of claim 1 wherein the biometric sensor is a galvanic skin response (GSR) skin conductance sensor to measure an electrical conductance of a skin of the wearer, which increases with sweat gland activity, and wherein a higher electrical conductance to indicate the elevated stress level.

5. The personal protective equipment of claim 1 wherein the biometric sensor is a blood pressure sensor to detect a temporary spike in blood pressure that indicates the elevated stress level.

6. The personal protective equipment of claim 1 wherein the responsive device to detect the elevated stress level using an artificial intelligence-based threat detection model.

7. The personal protective equipment of claim 6:
wherein the artificial intelligence-based threat detection model to also detect and analyze human emotion of the individual in an ambient area to the wearer using computer vision and auditory sensing to detect a presence or absence of an ambient threat.

8. The personal protective equipment of claim 7 wherein the responsive device is part of an array of haptic sensors to vibrate at different locations of a body of the wearer depending on a directional location of the ambient threat.

9. The personal protective equipment of claim 8:
wherein an intensity of vibration of the array of haptic sensors is dependent on a proximity of the ambient threat to the wearer, and
wherein a pattern of vibration of the responsive device is dependent on a type of ambient threat to the wearer.

10. The personal protective equipment of claim 1 wherein the biometric sensor to automatically document a health condition of the wearer and communicate that information to at least one of a command center and a hospital.

11. The personal protective equipment of claim 1:
wherein the biometric sensor is detachable from the tactical gear and placeable on an injured person nearby to the wearer through an armband extendable from the biometric sensor when it is removed from the tactical gear, and
wherein the biometric sensor to automatically communicate a biometric information of at least one of the injured person and the wearer to the hospital when removed from the tactical gear and placed on an arm of the injured person, when the injured person is en route to the hospital.

12. The personal protective equipment of claim 1 wherein the personal protective equipment communicates without electronic signature through a non-radiative, human-body-centered communication network.

13. A personal protective equipment, comprising:
a biometric sensor of a tactical gear to detect a health condition of a wearer; and
a responsive device to vibrate when the biometric sensor detects an elevated stress level of the wearer of the tactical gear,
wherein the biometric sensor is detachable from the tactical gear and placeable on an injured person nearby to the wearer through an armband extendable from the biometric sensor when it is removed from the tactical gear, and
wherein the biometric sensor to automatically communicate a biometric information of at least one of the injured person and the wearer to a hospital when removed from the tactical gear and placed on an arm of the injured person, when the injured person is en route to the hospital.

14. The personal protective equipment of claim 13 wherein the elevated stress level is detected through a heart rate monitor which determines whether a heart rate of the wearer is beyond an acceptable range.

15. The personal protective equipment of claim 14 wherein the heart rate monitor to evaluate heart rate variability (HRV), which is a variation in time between each heartbeat, and wherein a lower HRV is an indicator of the elevated stress level.

16. The personal protective equipment of claim 13 wherein the biometric sensor is a galvanic skin response (GSR) skin conductance sensor to measure an electrical conductance of a skin of the wearer, which increases with sweat gland activity, and wherein a higher electrical conductance to indicate the elevated stress level.

* * * * *